US006432656B1

(12) United States Patent
Del Mar et al.

(10) Patent No.: US 6,432,656 B1
(45) Date of Patent: Aug. 13, 2002

(54) CALCILYTIC COMPOUNDS

(75) Inventors: Eric G. Del Mar; Robert M. Barmore; Derek Sheehan; Bradford C. Van Wagenen, all of Salt Lake City, UT (US); James F. Callahan, Philadelphia; Richard M. Keenan, Malvern, both of PA (US); Nikesh R. Kotecha, Thurmaston (GB); Maria Amparo Lago, Audobon; Linda Sue Southall, West Chester, both of PA (US); Mervyn Thompson, The Pinnacles (GB)

(73) Assignee: NPS Pharmaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 09/370,097

(22) Filed: Aug. 6, 1999

Related U.S. Application Data

(62) Division of application No. 08/832,984, filed on Apr. 4, 1997, now Pat. No. 6,022,894.
(60) Provisional application No. 60/032,263, filed on Dec. 3, 1996, and provisional application No. 60/042,949, filed on Apr. 7, 1997.

(51) Int. Cl.$^7$ ....................... G01N 33/554; A61K 49/00
(52) U.S. Cl. ..................... 435/7.21; 424/9.2; 424/9.6; 435/40.5; 435/960; 436/501; 436/519; 436/546; 436/811; 436/815
(58) Field of Search ................................. 436/501, 811, 436/815, 546, 519; 435/7.21, 40.5, 960; 424/9.2, 9.6

(56) References Cited

U.S. PATENT DOCUMENTS

| | | | |
|---|---|---|---|
| 4,067,904 A | | 1/1978 | Comer et al. |
| 4,235,919 A | | 11/1980 | Berthold |
| 4,289,883 A | | 9/1981 | Tominaga et al. |
| 4,302,588 A | | 11/1981 | Tominaga et al. |
| 4,332,787 A | | 6/1982 | Homcy et al. |
| 4,376,125 A | | 3/1983 | Brooker et al. |
| 5,763,569 A | | 6/1998 | Brown et al. |
| 5,786,356 A | * | 7/1998 | Bell et al. ................. 514/248 |

FOREIGN PATENT DOCUMENTS

| | | |
|---|---|---|
| CH | 63 6856 | 6/1983 |
| DE | 2 400 658 | 7/1974 |
| DE | 2 502 993 | 9/1975 |
| DE | 2 530 613 | 5/1976 |
| DE | 2 711 719 | 9/1977 |
| DE | 2 830 211 | 2/1979 |
| DE | 2 914 166 | 10/1980 |
| DE | 2 943 406 | 5/1981 |
| DE | 2 944 222 | 5/1981 |
| DE | 3 301 198 | 7/1984 |
| DE | 3 416 976 | 11/1984 |
| DE | 4 040 186 | 6/1991 |
| DE | 4 017 019 | 11/1991 |
| DE | 29 8506 | 2/1992 |
| EP | 0 002 792 | 7/1979 |
| EP | 0 009 075 | 4/1980 |
| EP | 0 095 454 | 11/1983 |
| EP | 0 188 361 | 7/1986 |
| EP | 0 355 583 | 2/1990 |
| ES | 42 1076 | 9/1975 |
| ES | 44 2062 | 10/1975 |
| ES | 48 0066 | 4/1979 |
| GB | 1 058 822 | 2/1967 |
| GB | 1 129 072 | 10/1968 |
| GB | 1 518 689 | 9/1975 |
| GB | 2 192 394 | 1/1988 |
| JP | 1 199 037 | 7/1970 |
| JP | 52 108 980 | 9/1977 |
| JP | 56 008 319 | 1/1981 |
| JP | 57 080 321 | 5/1982 |
| WO | 92/20642 | 11/1992 |
| WO | 93/04373 | 3/1993 |
| WO | 94/18959 | 9/1994 |
| WO | 95/00493 | 1/1995 |
| WO | 95/11221 | 4/1995 |

OTHER PUBLICATIONS

Abrahamsson et al., "The $\beta_1$– and $\beta_2$–Adrenoceptor Affinity of Atenolol and Metroprolol: A Receptor–Binding Study Performed With Different Radioligands in Tissues from the Rat, The Guniea Pig and Man," *Biochemical Pharmacology* 37(2):203–208 (1988).

Aggerbeck et al., "Characterization of the β–Adrenoreceptor of Rat Liver Plasma Membrane. Structure Affinity relationship and role of the aralkyl substituent on the amino group," *Recent Advances in the Pharmacology of Adrenoceptors: Proceedings of a Satellite Symposium of the 7$^{th}$ International Congress of Pharmacology* held at Owens Park, Manchester pp. 345–346 (1978).

Aggerbeck et al., "N–Aralkyl Substitution Increases the Affinity of Adrenergic Drugs for the –Adrenoceptor in Rat Liver," *Br. J. Pharmacol.* 65(1):155–159 (1979).

Auerbach et al., "Neonatal Rat Pinealocytes: Typical and Atypical Characteristics of [$^{125}$I]Iodohydroxybenzylpindolol Binding and Adenosine 3',5'–Monophosphate Accumulation," *Endocrinology* 108(2):559–567 (1981).

Aurbach et al., "β–Adrenergic Receptor: Stereospecific Interaction of Iodinated β–Blocking Agent with High Affintiy Site," *Science* 186:1223–1224 (1974).

Bakardjieva et al., "Modulation of the β–Receptor Adenylate Cyclase Interactions in Cultured Chang Liver Cells by Phospholipid Enrichment," *Biochemistry* 18(14):3016–3023 (1979).

(List continued on next page.)

Primary Examiner—Mary E. Ceperley
(74) Attorney, Agent, or Firm—Richard J. Warburg; Foley & Lardner

(57) ABSTRACT

The present invention features calcilytic compounds. "calcilytic compounds" refer to compounds able to inhibit calcium receptor activity. Also described are the use of calcilytic compounds to inhibit calcium receptor activity and/or achieve a beneficial effect in a patient; and techniques which can be used to obtain additional calcilytic compounds.

9 Claims, No Drawings

OTHER PUBLICATIONS

Baker et al., "The Synthesis of N–Alkylated p–Chlorophentermine Derivatives and Their Effects on Release of 5–Hydroxytryptamine From Rat Striatum in Vitro," *Canadian Journal of Pharmaceutical Sciences* 15(4):71–74 (1980).

Bearer et al., "Iodohydroxybenzylpindolol: Preparation, Purification, Localization of Its Iodine to the Indole Ring, and Characterization as a Partial Agonist," *Molecular Pharmacology* 17(3):328–338 (1980).

Bilezikian et al., "Structure–Binding Activity Analysis of Beta–Adrenergic Amines—II. Binding to the Beta Receptor and Inhibition of Adenylate Cyclase," *Biochemical Pharmacology* 27(10):1455–1461 (1978).

Braun et al., "The Interaction of $Mn^{2+}$ with Turkey Erythrocyte Adenylate Cyclase," *Biochimica et Biophysica Acta* 705(1):55–62 (1982).

Brown et al., "Cloning and characterization of an extracellular $Ca^{2+}$ –sensing receptor from bovine parathyroid," *Nature* 366:575–580 (1993).

Brown et al., "Direct Determination of Ligand Interactions with Beta–Adrenergic Receptors on Intact Turkey Erythrocytes: Correlation of Binding with Biological Activity," *Endocrinology* 99(5):1370–1376 (1976).

Brown et al., "Neomycin Mimics the Effects of High Extracellular Calcium Concentrations on Parathyroid Function in Dispersed Bovine Parathyroid Cells," *Endocrinology* 128:3047–3054 (1991).

Brown et al., "β–Adrenergic Receptor Interactions: Characterization of Iodohydroxybenzylpindolol As A Specific Ligand," *J. Biol. Chem.* 251(5):1232–1238 (1976).

Brown et al., "β–Adrenergic Receptor Interactions: Direct Comparison of Receptor Interaction and Biological Activity," *J. Biol. Chem.* 251(5):1239–1246 (1976).

Burgisser et al., "Anamalous Equilibrium Binding Properties of High–Affinity Racemic Radioligands," *Molecular Pharmacology* 19(2)A:205–216 (1981).

Bylund and Snyder, "Beta Adrenergic Receptor Binding in Membrane Preparations from Mammalian Brain," *Molecular Pharmacology* 12(4):568–580 (1976).

Bylund et al., Beta Adrenergic Receptor Labeling in Intact Animals with $^{125}$I–Hydroxybenzylpindolol, *The Journal of Pharmacology and Experimental Therapeutics* 201(3):644–653 (1977).

Castedo et al., "β–Adrenergic Blockers: Synthesis of R–1–[(1,1–dimethyl–2–phenylethyl) amino]–3–(3, 4–dichlorophenoxy)–2–propanol," *Anales De Quimica,* Ser. C, 80(3):291–294, (1984).

Chen and Brown, "The Diltiazem Analog TA–3090 Mimics the Actions of High Extracellular $Ca^{2+}$ on Parathyroid Function in Dispersed Bovine Parathyroid Cells," *Journal of Bone and Mineral Research* 5:581–587 (1990).

Condon et al., "Nondepressant—Adrenergic Blocking Agents. 1. Substituted 3–Amino–1–(5,6,7, 8–tetrahydro–1–naphthoxy)–2–propanols," *J. Med. Chem.* 21(9):913–922 (1978).

Crowther et al., "–Adrenergic Blocking Agents. 12. Heterocyclic Compounds Related to Propranolol," *J. Med. Chem.* 15(3):260–266 (1972).

Dax and Partilla, "Adrenergic Ligand Liposolubility in Membranes: Direct Assessment in a Beta–Adrenergic Binding System," *Molecular Pharmacology* 22(1):5–7 (1982).

Dax et al., "Quantitation of Beta Adrenergic Receptors in Rat Liver: Confounding Effect of Displaceable But Nonsterospecific Antogonist Binding," *Journal of Receptor Research* 2(3):267–283 (1981).

Dempster et al., "Anabolic Actions of Parathyroid Hormone on Bone," *Endocrine Reviews* 14(6):690–709 (1993).

Eckelman et al., "In vivo Competition Studies with Analogues of 3–Quinuclidinyl Benzilate," *Journal of Pharmaceutical Sciences* 73(4):529–534 (1984).

Eckelman et al., "Radiochemistry and Radiopharmaceuticals: In Vivo Receptor Binding of Iodinated Beta–Adrenoceptor Blockers," *Journal of Nuclear Medicine* 21(5):436–442 (1980).

Espinosa and Ibanez–Paniello, "Adrenergic—Blockers: Synthesis of 1–[(1,1–dimethyl–2–phenylethyl) amino]–3–aryloxy–2–propanols," *Anales De Quimica,* Ser. C, 77(3):361–365 (1981).

Espinosa and Ibanez–Paniello, "β Blocking Adrenergics: Synthesis and Resolution of 1–[(1, 1–dimethyl–2–phenylethyl) amino]–3–aryloxy–2–propanols," *Anales De Quimica,* Ser. C, 77(1):22–27 (1981).

Esplugues et al., "Experimental Evaluation of Antianginal Drugs," *Revista Espanola de Fisiologia* 34(1):15–20 (1978).

Ezrailson et al., "[$^{125}$I]Iodopindolol: A New β Adrenergic Receptor Probe," *Journal of Cyclic Nucleotide Research* 7(1):13–26 (1981).

Fleming and Ross, "Reconstitution of Beta–Adrenergic Receptors Into Phospholipid Vesicles: Restoration of [$^{125}$I] Iodohydroxybenzylpindolol Binding to Digitonin–Solubilized Receptors," *Journal of Cyclic Nucleotide Research* 6(6):407–419 (1980)

Gao Guoxian et al., "Radioiodination and Pharmacokinetics of Bivalent Analog of Practolol as Myocardial Imaging Agent," *Nuclear Science and Techniques* 6(4):238–240 (1995) (listed as Cao but referenced in application as Gao).

Garrett et al., "Calcitonin–Secreting Cells of the Thyroid Express an Extracellular Calcium Receptor Gene," *Endocrinology* 136(11):5202–5211 (1995).

Goretzki et al., "Absence of high–affinity binding sites for beta–adrenergic blockers and lack of adenyl cyclase stimulation to beta–adrenergic stimulators in most normal and adenomatous human thyroid tissues," *Surgery* 96(6):1001–1008 (1984).

Gregory et al., "Ch. 8—The Beta–Adrenergic Receptor and Adenyl Cyclase of Rabbit Ciliary Processes," in *New Directions in Ophthalmic Research,* edited by Sears, Yale University Press, New Haven and London, pp. 127–145 (1981).

Guellaen et al., "Characterization and Solubilization of the α–Adrenoreceptor or Rat Liver Plasma Membranes Labeled with [$^3$H]Phenoxybenzamine," *J. Biol. Chem.* 254(21):10761–10768 (1979).

Hanel et al., "New systemically active antimycotics from the beta–blocker category," *Mycoses* 38(7/8):251–264 (1995).

Harada et al., "Studies on Uricosuric Diuretics. I. 6,7–Dichloro–5–sulfamoyl–2, 3–dihydrobenzofuran–2–carboxylic Acids," *Chem. Pharm. Bull.* 35(8):3195–3214 (1987).

Harden et al., "Binding of Iodinated Beta Adrenergic Antagonists to Proteins Derived from Rat Heart," *Molecular Pharmacology* 12:1–15 (1976).

Heidenleich et al., "Characterization of Radiolabeled Agonist Binding to β–Adrenergic Receptors in Mammalian Tissues," *Journal of Cyclic Nucleotide Research* 6(3):217–230 (1980).

Heidenleich et al., "Effects of Magnesium and N–Ethylmaleimide on the Binding of $^3$H–Hydrozybenzylisoproterenol to βAdrenergic Receptors," *J. Biol. Chem.* 257(2):804–810 (1982).

Homcy et al., "Beta Receptor Occupancy: Assessment in the Intact Animal," *J. Clin. Invest.* 65(5):1111–1118 (1980).

Ibanez–Paniello, "Sintesis de Derivados N–Sustituidos del 1–Amino–3–(p–acetamido Fenoxi)–2–Propanol Con Potencial Actividad Bloqueante β–Adrenergica,"0 *Anales De Quimica* 72(9–10):814–819 (1976).

Innis et al., "A Simple, Sensitive and Specific Radioreceptor Assay for β–Adrenergic Antagonist Drugs," *Life Sciences* 23(20):2031–2037 (1978).

Insel and Stoolman, "Radioligand Binding to Beta Adrenergic Receptors of Intact Cultured S49 Cells," *Molecular Pharmacology* 14:549–561 (1978).

Insel et al., "Beta Adrenergic Receptors and Adenylate Cyclase: Products of Separate Genes?" *Molecular Pharmacology* 12(6):1062–1069 (1976).

Jones et al., "Synthesis and Binding to β–Adrenergic Receptors of p–Aminobenzyl Analogues of Practolol and Atenolol," *Journal of Pharmaceutical Sciences* 81(4):397–398 (1992).

Kaumann, "A proposal for 3 classes of agonists from relations between β–adrenoceptor occupancy and positive inotropic effects in cat heart," *Progress in Pharmacology* 4(1):1–4 (1980).

Kaumann, "In Kitten Ventricular Myocardium, the Inotropic Potency of an Agonist is Determined by Both Its Intrinsic Activity for the Adenylyl Cyclase and its Affinity for the β–Adrenoceptors," *Naunyn–Schmeideberg's Arch. Pharmacol.* 317(1):13–18 (1981).

Kleinstein et al., "Solubilization of a Mammalian β–Adrenergic Receptor," *Naunyn–Schmeideberg's Arch. Pharmacol.* 305(3):191–200 (1978).

Kobayashi et al., "Identification of β–Adrenergic Receptor Binding Sites in Rat Brain Microvessels, Using [$^{125}$I]Iododihydroxylbenzylpindolol," *Journal of Neurochemistry* 36(4):1338–1388 (1981).

Lau et al., "Subclassification of β–Adrenergic Receptors in Cultured Rat Cardiac Myoblasts and Fibroblasts," *Circulation Research* 47(1):41–48 (1980).

Lautens and Ruoho, "Photoaffinity labeling of the β–adrenergic receptor in synaptic membranes of rat cerebral cortex and cerebellum," *Brain Research* 426(2):401–406 (1987).

Law and Stafford, "The use of ultraviolet spectra and chromatographic retention data as an aid to metabolite identification," *Journal of Pharmaceutical & Biomedical Analysis* 11(8):729–736 (1993).

Lee et al., "Beta–Adrenergic Receptors of Human Polymorphonuclear Leukocytes," *Research Communications in Chemical Pathology and Pharmacology* 31(3):453–462 (1981).

Lewitus and Laor, "Asymmetry of Beta–Adrenoceptors in Rat Brain, Labeled by 125–I–Hydroxybenzylpindolol," *Nuclear Medicine Communications* 2(3):180–182 (1981).

Limbird and Lefkowitz, "Negative Cooperativity among β–Adrenerigc Receptors in Frog Erythrocyte Membranes," *J. Biol. Chem.* 251(16):5007–5014 (1976).

Linschoten et al., "Mapping the Turkey Erythrocyte β Receptor: A Distance Geometry Approach," *J. Med. Chem.* 29(2):278–286 (1986).

Lucas and Bockaert, "Use of (–)–[$^3$H]Dihydroalprenolol to Study Beta Adrenergic Receptor–Adenylate Cyclase Coupling in C6 Glioma Cells: Role of 5'–Guanylylimidodiphosphate," *Molecular Pharmacology* 13(2):314–329 (1977).

Maguire et al., "An Agonist–Specific Effect of Guanine Nucleotides on Binding to the Beta Adenergic Receptor," *Molecular Pharmacology* 12(2):335–339 (1976).

Marinetti et al., "Beta–Adrenergic Receptors of Human Leukocytes: Studies with Intact Mononuclear and Polymorphonuclear Cells and Membranes Comparing Two Radioligands in the Presence and Absence of Chloroquine," *Biochemical Pharmacology* 32(13):2033–2043 (1983).

McClure et al., "Antihypertensive β–Adrenergic Blocking Agents: N–Aralkyl Analogues of 2–[3–(tert–Butylamino)–2–hydroxyproxy]–3–cyanopyridine," *J. Med. Chem.* 26(5):649–657 (1983).

McDonald et al., "The Development of Beta–Adrenergic Receptors in the Visual Cortex of the Rat," *Neuroscience* 7(11):2649–2655 (1982).

Meunier and Labrie, "Specificity of the $\beta_2$–Adrenergic Receptor Stimulating Cyclic AMP Accumulation in the Intermediate Lobe of Rat Pituitary Gland," *European Journal of Pharmacology* 81(3):411–420 (1982).

Minneman et al., "A Comparison of the Beta–Adrenergic Receptor of the Turkey Erythrocyte with Mammalian $Beta_1$ and $Beta_2$ Receptors," *Molecular Pharmacology* 17(1)1–7 (1980).

Mithal et al., "Highly Purified Sheep C–Cells Express and Extracellular $Ca^{2+}$ Receptor Similar to that Present in Parathyroid," *Journal of Bone and Mineral Research* 9(1):S282 at abstract No. B209 (1994).

Mukherjee et al., "Structure–Activity Relationships of Adenylate Cyclase–Coupled Beta Adrenergic Receptors: Determination by Direct Binding Studies," *Molecular Pharmacology* 12(1):16–31 (1971).

Munnich et al., "Rat Liver β–Adrenergic Receptors: Identification and Characterization with (–)[$^3$H]Dihydroalprenolol," *Horm. Metab. Res.* 13(1):18–21 (1981).

Nemeth and Carafoli, "The role of extracellular calcium in the regulation of intracellular calcium and cell function," *Cell Calcium* 11:319–321 (1990).

Nemeth and Scarpa, "Spermine Evokes the Rapid Mobilization of Cellular $Ca^{2+}$ in Parathyroid Cells," in *Calcium–Binding Proteins in Health and Disease,* Norman et al. editors, Academic Press, Inc., San Diego, pp. 33–35 (1987).

Nemeth, "Regulation of cystolic calcium by extracellular divalent cations in C–cells an parathyroid cells," *Cell Calcium* 11:323–327 (1990).

Nero et al., "–Adrenoceptor agonists and antagonists: conformational analysis of the ethanolamine and propanolamine side–chain," *Journal of Molecular Structure (Theochem)* 285:251–272 (1993).

Neve et al., "Quantitative Analysis of the Selectivity of Radioligands for Subtypes of Beta Adrenergic Receptors," *The Journal of Pharmacology and Experimental Therapeutics* 238(1):46–53 (1986).

Oshiro et al., "Syntheses of 8–Acylamino–3,4–dihydrocarbostyril Derivatives with β–Adrenergic Blocking Action," *Yakugaku Zasshi* 104(1):28–36 (1984).

Paietta et al., "Non–Specific Uptake of the Radioligand [125]I–IHYP By Intact Human Lymphocytes: Reversal of the Uptake Process," *Molecular and Cellular Endocrinology* 25(3):267–276 (1982).

Riva and Creese, "Comparison of Two Putatively Selective Radioligands for Labeling Central Nervous System β–Adrenergic Receptors: Inadequacy of [$^3$H]Dihydroalprenolol," *Molecular Pharmacology* 36:201–210 (1989).

Roberts et al., "Identification of Beta–Adrenergic Binding Sites in Rabbit Myometrium," *Endocrinology* 101(6):1839–1843 (1997).

Rockson et al., "Anti–Alprenolol Antibodies in the Rabbit: A New Probe for the Study of β–Adrenergic Receptor Interaction," *Circulation Research* 46(6):808–813 (1980).

Rogers et al., "Calcium Receptor Messenger Ribonucleic Acid Levels in the Parathyroid Glands and Kidney of Vitamin D–Deficient Rats Are Not Regulated by Plamsa Calcium or 1,25–Dihydroxyvitamin $D_3$," *Endocrinology* 136(2):499–504 (1995).

Rogers et al.., "Localization of Calcium Receptor mRNA in Rat Thyroid and Parathyroid Glands Using In Situ Hybridization Histochemistry," *Journal of Bone and Mineral Research* 9(1):S409 at abstract No. C390 (1994).

Rogers et al., "Pharmacological Comparison of Bovine Parathyroid, Human Parathyroid and Rat Kidney Calcium Receptors Expressed in HEK 293 Cells," *Journal of Bone and Mineral Research* 10(1):S:483 (1995).

Ruoho et al., "[$^{125}$I]–Iodoazidobenzylpindolol–Photolabeling of the β–Adrenergic Receptor from Lymphoma Cells: Properties of the 65K and 55K Pollypeptides," in *Adrenergic Receptors: Molecular Properties and Therapeutic Implications,* Symposium St.–Paul–de–Vence, France, Oct. $21^{st}$–$24^{th}$, 1984, pp. 87–103 (1985).

Ruoho et al., "Use of photolabels to probe the Na, K–ATPase and the β–adrenergic receptor," *Federation Proc.* 42(11):2837–2841 (1983).

Sager et al., "Adrenergic ligand binding in human serum," *Biochemical Pharmacology* 34(15):2812–2815 (1985).

Sahyoun et al., "Topographic separation of adenylate cyclase and hormone receptors in the plasma membrane of toad erythrocyte ghosts," *Proc. Natl. Acad. Sci. USA* 74(7):2860–2864 (1977).

Schaeffer et al., "Inhibition of Synaptosomal Accumulation of I–Norepinerphrine II: N–Aryloxyalkylphentermines, Quaternary d–Amphetamines, and 3–Aryloxypropylamines," *Journal of Pharmaceutical Sciences* 65(1):122–126 (1976).

Smejkal et al., "Series of new adrenergic products," *Therapie* 22(6):1343–1347 (1967).

Terasaki and Brooker, "[$^{125}$I]Iodohydroxybenzylpindolol Binding Sites on Intact Rat Glioma Cells: Evidence for β–Adrenergic Receptors of High Coupling Efficiency," *J. Biol. Chem.* 253(15):5418–5425 (1978).

Terasaki et al., "Quantitatie relationship between β–adrenergic receptor number and physiologic responses as studied with a long–lasting β–adrenergic antagonist," *Proc. Natl. Acad. Sci. USA* 76(12):6401–6405 (1979).

Tolkovsky and Levitzki, "Collison Coupling of the β–Adrenergic Receptor with Adenylate Cyclase," *Hormones and Cell Regulation,* edited by Dumont and Nunez, North–Holland Biomedical Press, 2:89–105 (1978).

Tominaga et al., "Studies on Positive Inotropic Agents. IV. Synthesis of 5–(3–Amino–2–hydroxypropoxy)–3, 4–dihydro–8–hydroxy–2(1H)–quinolinone Derivatives," *Chem. Pharm. Bull.* 35(9):3699–3704 (1987).

Tominaga et al., "Syntheses and β–Adrenergic Blocking Activities of Carbostyril Derivatives," *Chem. Pharm. Bull.* 29(8):2166–2181 (1981).

Trope et al., "Identification of Beta–Adrenergic Receptors in the Pigmented Mammalian Iris–Ciliary Body Diaphragm," *Exp. Eye Res.* 34(1):153–157 (1982).

Tropea and Almon, "Definition of a Beta–Adrenergic Receptor Population in Skeletal Muscle: [$^{125}$I]Hydroxybenzylpindolol Binding," *Gen. Pharmacol.* 11(2):161–164 (1980).

U'Prichard et al., "(±)–[$^3$H]Epinephrine and (−)–[$^3$H]Dihydroalprenolol Binding to $\beta_1$– and $\beta_2$– Noradrenergic Receptors in Brain, Heart, and Lung Membranes," *J. Biol. Chem.* 253(14):5090–5102 (1978).

Weber and Petcher, "139. The Crystal and Molecular Structure of Hydroxybenzylpindolol," *Helvetica Chimica Acta* 60(4):1398–1402 (1977).

Willcocks and Nahorski, "Binding of $^{125}$Iodohydroxybenzylpindolol to Cerebral Membranes: Association with 5–Hydroxytryptamine Recognition Sites as Well as Beta–Adrenoceptors," *Biochemical Pharmacology* 32(22):3311–3319 (1983).

Wolfe and Harden, "Guanine Nucleotides Modulate the Affinity of Antagonists at β–Adrenergic Receptors," *Journal of Cyclic Nucleotide Research* 7(5):303–312 (1981).

Yamamura and Rodbell, "Hydroxybenzylpindolol: and Hydroxybenzylpropranolol: Partial Beta Adrenergic Agonists of Adenylate Cyclase in the Rat Adipocyte," *Molecular Pharmacology* 12(5):693–700 (1976).

Zaidi et al., "Intracellular calcium in the control of osteoclast function. II. Paradoxical elevation of cytosolic free calcium by verapamil," *Biochemical and Biophysical Research Communications* 167:807–812 (1990).

Zaidi, "'Calcium Receptors' on Eukaryotic Cells with Special Reference to Osteoclast," *Bioscience Reports* 10:493–507 (1990).

\* cited by examiner

CALCILYTIC COMPOUNDS

RELATED APPLICATIONS

This application is a divisional of application Ser. No. 08/832,984, filed Apr. 4, 1997, now U.S. Pat. No. 6,022,894 which is a continuation of application Ser. No. 60/042,949, filed Apr. 7, 1996. This application is also a continuation-in-part of U.S. Ser. No. 60/032,263, filed Dec. 3, 1996.

FIELD OF THE INVENTION

The present invention relates to compounds able to inhibit calcium receptor activity and the use of such compounds. Preferably, the compounds described herein are administered to patients to achieve a therapeutic effect.

BACKGROUND OF THE INVENTION

Certain cells in the body respond not only to chemical signals, but also to ions such as extracellular calcium ions ($Ca^{2+}$). Extracellular $Ca^{2+}$ is under tight homeostatic control and regulates various processes such as blood clotting, nerve and muscle excitability, and proper bone formation.

Calcium receptor proteins enable certain specialized cells to respond to changes in extracellular $Ca^{2+}$ concentration. For example, extracellular $Ca^{2+}$ inhibits the secretion of parathyroid hormone (PTH) from parathyroid cells, inhibits bone resorption by osteoclasts, and stimulates secretion of calcitonin from C-cells.

PTH is the principal endocrine factor regulating $Ca^{2+}$ homeostasis in the blood and extracellular fluids. PTH, by acting on bone and kidney cells, increases the level of $Ca^{2+}$ in the blood. This increase in extracellular $Ca^{2+}$ then acts as a negative feedback signal, depressing PTH secretion. The reciprocal relationship between extracellular $Ca^{2+}$ and PTH secretion forms an important mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in extracellular $Ca^{2+}$ has been confirmed. (Brown et al., *Nature* 366:574, 1993.) In parathyroid cells, this protein, the calcium receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ can exert effects on different cell functions, reviewed in Nemeth et al., *Cell Calcium* 11:319, 1990. The role of extracellular $Ca^{2+}$ in parafollicular (C-cells) and parathyroid cells is discussed in Nemeth, *Cell Calcium* 11:323, 1990. These cells were shown to express similar calcium receptors. (See, Brown et al., *Nature* 366:574, 1993; Mithal et al., *J. Bone Miner. Res.* 9, Suppl. 1, s282, 1994; Rogers et al., *J. Bone Miner. Res.* 9, Suppl, 1, s409, 1994; Garrett et al., *Endocrinology* 136:5202–5211, 1995.) The role of extracellular $Ca^{2+}$ on bone osteoclasts is discussed by Zaidi, *Bioscience Reports* 10:493, 1990.

The ability of various molecules to mimic extracellular $Ca^{2+}$ in vitro is discussed in references such as Nemeth et al., in "Calcium-Binding Proteins in Health and Disease," 1987, Academic Press, Inc., pp. 33–35; Brown et al., *Endocrinology* 128:3047, 1991; Chen et al., *J. Bone Miner. Res.* 5:581, 1990; and Zaidi et al., *Biochem. Biophys. Res. Commun.* 167:807, 1990.

Nemeth et al., PCT/US92/07175, International Publication Number WO 93/04373, Nemeth et al., PCT/US93/01642, International Publication Number WO 94/18959, and Nemeth et al., PCT/US94/12117, International Publication Number WO 95/11211, feature calcium receptor-active molecules and refer to calcilytics as compounds able to inhibit calcium receptor activity. For example, WO 94/18959 on page 8, lines 2–13 asserts:

Applicant is also the first to describe methods by which molecules active at these $Ca^{2+}$ receptors can be identified and used as lead molecules in the discovery, development, design, modification and/or construction of useful calcimimetics or calcilytics which are active at $Ca^{2+}$ receptors. Such calcimimetics or calcilytics are useful in the treatment of various disease states characterized by abnormal levels of one or more components, e.g., polypeptides such as hormones, enzymes or growth factors, the expresssion and/or secretion of which is regulated or affected by activity at one or more $Ca^{2+}$ receptors.

The references provided in the background are not admitted to be prior art to the pending claims.

SUMMARY OF THE INVENTION

The present invention features calcilytic compounds. "Calcilytic compounds" refer to compounds able to inhibit calcium receptor activity. The ability of a compound to "inhibit calcium receptor activity" means that the compound causes a decrease in one or more calcium receptor activities evoked by extracellular $Ca^{2+}$.

The use of calcilytic compounds to inhibit calcium receptor activity and/or achieve a beneficial effect in a patient are described below. Also described below are techniques which can be used to obtain additional calcilytic compounds.

An example of featured calcilytic compounds are Structure I α,α-disubstituted arylalkylamine derivatives having the chemical formula:

STRUCTURE I

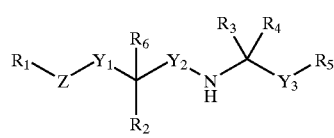

where $R_1$ is selected from the group consisting of: aryl, longer-length alk, and cycloalk;

$R_2$ is selected from the group consisting of: lower alk, cycloalk, alkoxy, H, OH, =O, C(O)OH, C(O)O-lower alk, C(O)NH-lower alk, C(O)N(lower alk)$_2$, SH, S-lower alk, NH$_2$, NH-lower alk, and N(lower alk)$_2$;

$R_3$ and $R_4$ is each independently lower alk or together cyclopropyl;

R5 is aryl;

$R_6$ if present is either hydrogen, lower alkyl or lower alkenyl, wherein $R_6$ is not present if $R_2$ is =O;

$Y_1$ is either covalent bond, alkylene, or alkenylene;

$Y_2$ is alkylene;

$Y_3$ is alkylene; and

Z is selected from the group consisting of: covalent bond, O, S, NH, N-lower alk, alkylene, alkenylene, and alkynylene, provided that if Z is either O, S, NH, or N-lower alk, then $Y_1$ is not a covalent bond, further provided that $Y_1$ and Z may together be a covalent bond;

and pharmaceutically acceptable salts and complexes thereof.

The terms aryl, longer-length alk, lower alk, cycloalk, alkoxy, alkylene, alkenylene, and alkynylene, along with possible substituents are defined in Section II, infra. Section II, infra, also provides definitions for other chemical groups described in the present application.

Preferred calcilytic compounds have an $IC_{50} \leq 50$ μM, more preferably an $IC_{50} < 10$ μM, and even more preferably an $IC_{50} < 1$ μM, as measured using the "Calcium Receptor Inhibitor Assay" described in Example 1, infra.

Thus, a first aspect of the present invention features a method of treating a patient by administering to the patient a therapeutically effective amount of a Structure I α,α-disubstituted arylalkylamine derivative. Treatment can be carried out, for example, to retard the disease in a patient having a disease or to prophylactically retard or prevent the onset of a disease.

A therapeutically effective amount is the amount of compound which achieves a therapeutic effect by retarding a disease in a patient having a disease or prophylactically retarding or preventing the onset of a disease. Preferably, it is an amount which relieves to some extent one or more symptoms of a disease or disorder in a patient; returns to normal either partially or completely one or more physiological or biochemical parameters associated with or causative of the disease or disorder; and/or reduces the likelihood of the onset of the disease of disorder.

A "patient" refers to a mammal in which compounds characterized by their ability to inhibit calcium receptor activity, in vivo or in vitro, will have a beneficial effect. Preferably, the patient is a human being.

Patients benefiting from the administration of a therapeutic amount of a calcilytic compound can be identified using standard techniques known to those in the medical profession. Diseases or disorders which can be treated by inhibiting one or more calcium receptor activities include one or more of the following types: (1) those characterized by an abnormal bone and mineral homeostasis; (2) those characterized by an abnormal amount of an extracellular or intracellular messenger whose production can be affected by one or more calcium receptor activities; (3) those characterized by an abnormal effect (e.g., a different effect in kind or magnitude) of an intracellular or extracellular messenger which can itself be ameliorated by one or more calcium receptor activities; and (4) other diseases or disorders where inhibition of one or more calcium receptor activities exerts a beneficial effect, for example, in diseases or disorders where the production of an intracellular or extracellular messenger stimulated by receptor activity compensates for an abnormal amount of a different messenger. Examples of extracellular messengers whose secretion and/or effect can be affected by inhibiting calcium receptor activity are believed to include inorganic ions, hormones, neurotransmitters, growth factors, and chemokines. Examples of intracellular messengers include cAMP, cGMP, $IP_3$, calcium, magnesium, and diacylglycerol.

Preferably, a patient is a human having a disease or disorder characterized by one or more of the following: (1) an abnormal bone or mineral homeostasis; (2) an abnormal amount of an extracellular or intracellular messenger which is ameliorated by a compound able to effect one or more calcium receptor activities; and (3) an abnormal effect of an intracellular or extracellular messenger which is ameliorated by a compound able to effect one or more calcium receptor activities.

Preferably, the disease or disorder is characterized by an abnormal bone and mineral homeostasis, more preferably calcium homeostasis. Abnormal calcium homeostasis is characterized by one or more of the following activities: (1) an abnormal increase or decrease in serum calcium; (2) an abnormal increase or decrease in urinary excretion of calcium; (3) an abnormal increase or decrease in bone calcium levels, for example, as assessed by bone mineral density measurements; (4) an abnormal absorption of dietary calcium; (5) an abnormal increase or decrease in the production and/or release of messengers which affect serum calcium levels such as PTH and calcitonin; and (6) an abnormal change in the response elicited by messengers which affect serum calcium levels. The abnormal increase or decrease in these different aspects of calcium homeostasis is relative to that occurring in the general population and is generally associated with a disease or disorder.

Preferably, the calcilytic compounds are used to treat diseases or disorders selected from the group consisting of: hypoparathyroidism, osteosarcoma, periodontal disease, fracture healing, osteoarthritis, rheumatoid arthritis, Paget's disease, humoral hypercalcemia malignancy, and osteoporosis.

Another aspect of the present invention describes a method of treating a patient comprising the step of administering to the patient an amount of a calcilytic compound sufficient to increase serum PTH level. Preferably, the method is carried out by administering an amount of the compound effective to cause an increase in duration and/or quantity of serum PTH level sufficient to have a therapeutic effect.

Increasing serum PTH may be used to achieve a therapeutic effect by retarding a disease in a patient having the disease or prophylactically retarding or preventing the onset of a disease. Prophylactic treatment can be performed, for example, on a person with an abnormally low serum PTH; or on a person without a low serum PTH, but where increasing PTH has a beneficial effect. An abnormally low serum PTH is a serum PTH level lower than that occurring in the general population, and is preferably an amount associated with a disease or the onset of a disease.

Increasing serum PTH levels can be used to treat different types of diseases including bone and mineral related diseases.

In different embodiments, the compound administered to a patient causes an increase in serum PTH having a duration up to one hour, about one to about twenty-four hours, about one to about twelve hours, about one to about six hours, about one to about five hours, about one to about four hours, about two to about five hours, about two to about four hours, or about three to about six hours.

In additional different embodiments, the compound administered to a patient causes an increase in serum PTH up to 0.5 fold, 0.5 to 5 fold, 5 fold to 10 ten fold, and at least 10 fold, greater than peak serum PTH in the patient. The peak serum level is measured with respect to the patient not undergoing treatment.

Another aspect of the present invention features Structure I calcilytic compounds.

Another aspect of the present invention features a pharmaceutical composition comprising a pharmaceutically acceptable carrier and a calcilytic compound decscribed herein. The pharmaceutical composition contains the calcilytic compouind in a form suitable for administration into a mammal, preferably, a human being. Preferably, the pharmaceutical comosition contains an amount of a calcilytic compound in a proper pharmaceutical dosage form sufficient to exert a therapeutic effect on a human being. However, multiple doses of pharmaceutical compositions may be used to treat a patient.

Considerations and factors concerning dosage forms suitable for administration are known in the art and include potential toxic effects, solubility, route of administration, and maintaining activity. For example, pharmaceutical compositions injected into the bloodstream should be soluble.

Another aspect of the present invention features a method of screening for Structure I α,α-disubstituted arylalkylamine derivatives able to inhibit calcium receptor activity. The method involves the steps of contacting a cell having a calcium receptor with a Structure I α,α-disubstituted arylalkylamine arylalkylamine derivative and measuring the ability of the compound to inhibit calcium receptor activity.

The screening method can be carried out in vivo or in vitro and is particularly useful to identify those Structure I α,α-disubstituted arylalkylamine derivatives most able to act as calcilytic compounds. In vivo assays include measuring a physiological parameter related to calcium receptor activity, such as serum hormone levels or serum calcium ion concentration. In vitro assays include measuring the ability of the calcilytic compound to affect intracellular calcium concentration, or cellular hormone secretion. Examples of hormones levels which can be affected by calcilytic compounds include PTH and calcitonin.

The calcilytic compounds described herein can be used as part of in vivo or in vitro methods. Preferably, the compounds are used in vivo to achieve a beneficial effect in a patient. Examples of in vitro uses, and other in vivo uses, include use in a method to identify other calcilytic compounds and use as a tool to investigate calcium receptor activity or the physiological effects of inhibiting calcium receptor activity in different organisms.

Other features and advantages of the invention will be apparent from the following detailed description of the invention, examples, and the claims.

DETAILED DESCRIPTION OF THE INVENTION

The present application demonstrates the ability of calcilytic compounds to exert a physiologically relevant effect on a cell by illustrating the ability of such compounds to increase PTH secretion and also identifies a target site for calcilytic compounds. The present application is believed to be the first to demonstrate that calcilytic compounds can increase PTH secretion.

Calcium receptors are present on different cell types and can regulate different responses in different cell types. While the calcilytic compounds described herein are believed to act at a calcium receptor through a calcium receptor-activity modulating site, unless otherwise explicitly stated in the claims that a compound exerts an effect by acting at a calcium receptor through such a site, there is no intention to limit the claimed methods or compound to requiring inhibition of calcium receptor activity or any particular mode of action. Rather, the present application demonstrates that compounds able to inhibit calcium receptor activity, whose calcilytic activity can be measured in vivo or in vitro, exert significant physiological effects. For example, the present application demonstrates the ability of different calcilytic compounds to prevent $Ca^{2+}$ inhibition of PTH and, thereby, result in an increase in PTH release.

Compounds binding at the calcium receptor-activity modulating site can be identified using a labeled compound binding to the site in a competition-binding assay format.

Preferred calcilytic compounds described herein are Structure I α,α-disubstituted arylalkylamine derivatives able to inhibit calcium receptor activity. Other aspects of the present invention include assays which can be used to identify those Structure I α,α-disubstituted arylalkylamine derivatives expected to be effective in inhibiting calcium receptor activity, and/or exerting a therapeutic effect in a patient; preferred groups of Structure I α,α-disubstituted arylalkylamine derivatives; and the use of the compounds described herein to treat different diseases or disorders.

I. CALCIUM RECEPTOR ACTIVITY

Calcium receptors respond to changes in extracellular calcium levels. The exact changes resulting from calcium receptor activity depend on the particular receptor and the cell containing the receptor. For example, the in vitro effect of calcium on the calcium receptor in a parathyroid cell includes the following:

1. An increase in internal calcium $[Ca^{2+}]_i$. The increase is due to the influx of external calcium and/or to the mobilization of internal calcium. Characteristics of the increase in internal calcium include the following:
    (a) A rapid (time to peak<5 seconds) and transient increase in $[Ca^{2+}]_i$ that is refractory to inhibition by 1 μM $La^{3+}$ or 1 μM $Gd^{3+}$ and is abolished by pretreatment with ionomycin (in the absence of extracellular $Ca^{2+}$);
    (b) The increase is not inhibited by dihydropyridines;
    (c) The transient increase is abolished by pretreatment for 10 minutes with 10 mM sodium fluoride;
    (d) The transient increase is diminished by pretreatment with an activator of protein kinase C (PKC), such as phorbol myristate acetate (PMA), mezerein or (−)-indolactam V. The overall effect of the protein kinase C activator is to shift the concentration-response curve of calcium to the right without affecting the maximal response; and
    (e) Pretreatment with pertussis toxin (100 ng/ml for >4 hours) does not affect the increase.
2. A rapid (<30 seconds) increase in the formation of inositol-1,4,5-triphosphate and/or diacylglycerol. Pretreatment with pertussis toxin (100 ng/ml for >4 hours) does not affect this increase;
3. The inhibition of dopamine- and isoproterenol-stimulated cyclic AMP formation. This effect is blocked by pretreatment with pertussis toxin (100 ng/ml for >4 hours); and
4. The inhibition of PTH secretion. Pretreatment with pertussis toxin (100 ng/ml for >4 hours) does not affect the inhibition of PTH secretion.

Calcilytic activity of a compound can be determined using techniques such as those described in the examples below and those described in publications such as Nemeth et al., PCT/US92/07175, International Publication Number WO 93/04373, Nemeth et al., PCT/US93/01642, International Publication Number WO 94/18959, and Nemeth et al., PCT/US94/12117, International Publication Number WO 95/11211 (each of which are hereby incorporated by reference herein).

Calcilytic activity varies depending upon the cell type in which the activity is measured. For example, calcilytic compounds possess one or more, and preferably all, of the following characteristics when tested on parathyroid cells in vitro:

1. The compound blocks, either partially or completely, the ability of increased concentrations of extracellular $Ca^{2+}$ to:
    (a) increase $[Ca^{2+}]_i$,
    (b) mobilize intracellular $Ca^{2+}$, (c) increase the formation of inositol-1,4,5-triphosphate,
(d) decrease dopamine- or isoproterenol-stimulated cyclic AMP formation, and
(e) inhibit PTH secretion;

2. The compound blocks increases in Cl⁻ current in Xenopus oocytes injected with poly(A)$^+$-mRNA from bovine or human parathyroid cells elicited by extracellular $Ca^{2+}$ but not in Xenopus oocytes injected with water; and 3. Similarly, the compound blocks a response in Xenopus oocytes, injected with cloned nucleic acid expressing the calcium receptor, elicited by extracellular $Ca^{2+}$ or a calcimimetic compound (i.e., a compound able to mimic the effect of extracellular $Ca^{2+}$, including compounds potentiating the effect of extracellular $Ca^{2+}$).

Calcium receptors are present in different cells. The pharmacological effects of the following cells, in response to extracellular $Ca^{2+}$, is consistent with the presence of a calcium receptor: parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, endocrine and exocrine cells in the pancreas, fat/adipose cell, immune cell, GI tract cell, skin cell, adrenal cell, pituitary cell, hypothalamic cell and cell of the subfornical organ.

The presence of a calcium receptor on the following cells have been confirmed using physical data, such as hybridization with nucleic acid encoding a calcium receptor: parathyroid cell, central nervous system cell, peripheral nervous system cell, cell of the thick ascending limb of Henle's loop and/or collecting duct in the kidney, parafollicular cell in the thyroid (C-cell), intestinal cell, GI tract cell, pituitary cell, hypothalamic cell, cell of the subfornical organ, and endocrine and exocrine cells in the pancreas.

II. α,α-DISUBSTITUTED ARYLALKYLAMINE DERIVATIVES

Structure I α,α-disubstituted arylalkylamine derivatives have the following chemical formula:

STRUCTURE I

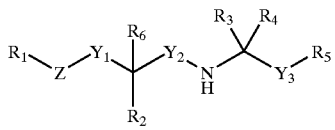

where $R_1$ is selected from the group consisting of: aryl, longer-length alk, and cycloalk. Preferably, $R_1$ is either optionally substituted phenyl, optionally substituted pyridyl, optionally substituted benzothiopyranyl, optionally substituted carbazole, optionally substituted naphthyl, optionally substituted tetrahydronaphthyl, optionally substituted longer-length alkyl, optionally substituted longer-length alkenyl or optionally substituted cycloalk.

More preferably, $R_1$ is either an optionally substituted phenyl; an optionally substituted naphthyl; an optionally substituted pyridyl; an optionally substituted benzothiopyranyl; an optionally substituted carbazole; unsubstituted longer-length alkyl; unsubstituted longer-length alkenyl; or monosubstituted longer-length alkyl or alkenyl, where the monosubstituent is either an optionally substituted phenyl or an optionally substituted cycloalkyl provided that the optionally substituted phenyl or optionally substituted cycloalkyl can have one to four substituents each independently selected from the group consisting of: alkoxy, lower-haloalkyl, S-unsubstituted alkyl, lower-haloalkoxy, unsubstituted alkyl, unsubstituted alkenyl, halogen, SH, CN, $NO_2$, $NH_2$ and OH;

$R_2$ is selected from the group consisting of: lower alk, cycloalk, alkoxy, H, OH, =O, C(O)OH, C(O)O-lower alk, C(O)NH-lower alk, C(O)N(lower alk)$_2$, SH, S-lower alk, $NH_2$, NH-lower alk, and N(lower alk)$_2$. More preferably, $R_2$ is OH or alkoxy, even more preferably, $R_2$ is OH or methoxy;

$R_3$ and $R_4$ is each independently lower alk or together cyclopropyl. Preferably, $R_3$ and $R_4$ are each independently a lower alkyl, more preferably, $R_3$ and $R_4$ are each independently methyl or ethyl;

$R_5$ is aryl. Preferably, $R_5$ is either optionally substituted naphthyl or optionally substituted phenyl. More preferably, $R_5$ is substituted phenyl having a substituent in the meta or para position and optionally containing additional substituents;

$R_6$ if present is either hydrogen, lower alkyl or lower alkenyl, wherein $R_6$ is not present if $R_2$ is =O. Preferably $R_6$ is either hydrogen or lower alkyl, more preferably $R_6$ is hydrogen.

$Y_1$ is either covalent bond, alkylene, or alkenylene. Preferably, $Y_1$ is either covalent bond or lower alkylene. More preferably, $Y_1$ is methylene;

$Y_2$ is alkylene. Preferably, $Y_2$ is lower alkylene. More preferably, $Y_2$ is methylene;

$Y_3$ is alkylene. Preferably, $Y_3$ is lower alkylene. More preferably, $Y_3$ is methylene;

Z is selected from the group consisting of: covalent bond, O, S, NH, N-lower alk, alkylene, alkenylene, and alkynylene, provided that if Z is either O, S, NH, or N-lower alk, then $Y_1$ is not a covalent bond, further provided that $Y_1$ and Z may together be a covalent bond. Preferably, Z is selected from the group consisting of: covalent bond, O, S, NH, N-lower alk, and alkylene. More preferably, Z is either O, S, lower alkylene, even more preferably, Z is O;

and pharmaceutically acceptable salts and complexes thereof.

"Alk" refers to either alkyl, alkenyl, or alkynyl. "Lower alk" refers to either lower alkyl, lower alkenyl, or lower alkynyl, preferably, lower alkyl. "Alkenyl" refers to an optionally substituted hydrocarbon group containing at least one carbon-carbon double bond between the carbon atoms and containing 2–15 carbon atoms joined together. The alkenyl hydrocarbon group may be straight-chain or contain one or more branches. Branched- and straight-chain alkenyl preferably have 2 to 7 carbons, each of which may be optionally substituted. Alkenyl substituents are each independently selected from the group consisting of: lower alkyl, lower alkenyl, halogen, alkoxy, lower haloalkyl, lower haloalkoxy, methylene dioxy, unsubstituted aryl, unsubstituted cycloalkyl, OH, SH, CN, NO, $NO_2$, $NH_2$, CH=NNHC(O)$NH_2$, CH=NNHC(S)$NH_2$, $CH_2$O-lower alkyl, C(O) lower alkyl, C(O)$NH_2$, C(O)NH-lower alkyl, C(O)N(lower alkyl)$_2$, C(O)OH, C(O)O-lower alkyl, NH-lower alkyl, N(lower alkyl)$_2$, NHC(O)unsubstituted aryl, NHC(O)lower alkyl, N=N-unsubstituted aryl, NHC(O)$NH_2$, N(lower alkyl)C(O)lower alkyl, NHC(S)lower alkyl, N(lower alkyl)C(S)lower alkyl, NHS(O)lower alkyl, N(lower alkyl)S(O) lower alkyl, OC(O)lower alkyl, OCH$_2$C(O)OH, OC(S)lower alkyl, S(O)lower alkyl, SC(O)lower alkyl, S-lower alkyl, S-lower haloalkyl, SO$_2$-lower alkyl, SO$_2$-lower haloalkyl, S(O)$_2$NH$_2$, S(O)$_2$NH-lower alkyl, and S(O)$_2$N(lower alkyl)$_2$. Preferably, no more than three substituents are present. Even more preferably, the alkenyl is a lower alkenyl, which is an unsubstituted branched- or straight-chain alkenyl having 2 to 4 carbons.

"Alkyl" refers to an optionally substituted hydrocarbon group joined by single carbon-carbon bonds and having 1–15 carbon atoms joined together. The alkyl hydrocarbon group may be straight-chain or contain one or more branches. Branched- and straight-chain alkyl preferably have 1 to 7 carbons, each of which may be optionally substituted. Alkyl substituents are each independently selected from the substituents described above for alkenyl. Preferably, no more than three substituents are present. More preferably, the alkyl is a lower alkyl, which is an unsubstituted branched- or straight-chain alkyl 1 to 4 carbons in length.

"Alkynyl" refers to an optionally substituted hydrocarbon group containing at least one carbon-carbon triple bond between the carbon atoms and containing 2–15 carbon atoms joined together. The alkynyl hydrocarbon group may be straight-chain or contain one or more branches. Branched- and straight-chain alkynyl preferably have 2 to 7 carbons, each of which may be optionally substituted. Alkynyl substituents are each independently selected from the substituents described above for alkenyl. Preferably, no more than three substituents are present. More preferably, the alkynyl is a lower alkynyl, which is an unsubstituted branched- or straight-chain alkynyl having 2 to 4 carbons.

"Alkenylene" refers to an optionally substituted hydrocarbon chain containing at least one carbon-carbon double bond between the carbon atoms. The alkenylene chain has 2 to 6 carbons and is attached at two locations to other functional groups or structural moieties. The alkenylene substituents are each independently selected from the substituents described above for alkenyl. Preferably, no more than three substituents are present. More preferably, the alkenylene is a "lower alkenylene," which is an unsubstituted branched- or straight-chain alkenylene having 2 to 3 carbons.

"Alkoxy" refers to oxygen joined to an unsubstituted alkyl 1 to 12 carbon atoms in length, preferably 1 to 2 carbons in length. More preferably, the alkoxy is methoxy.

"Alkylene" refers to an optionally substituted hydrocarbon chain containing only carbon-carbon single bonds between the carbon atoms. The alkylene chain has 1 to 6 carbons and is attached at two locations to other functional groups or structural moieties. The alkylene substituents are each independently selected from the substituents described above for alkenyl. Preferably, no more than three substituents are present. More preferably, the alkylene is a "lower alkylene," which is an unsubstituted branched- or straight-chain alkylene having 1 to 3 carbons.

"Alkynylene" refers to an optionally substituted hydrocarbon chain containing at least one carbon-carbon triple bond between the carbon atoms. The alkynylene chain has 2 to 6 carbons and is attached at two locations to other functional groups or structural moieties. The alkynylene substituents are each independently selected from the substituents described above for alkenyl. More preferably, the alkynylene is a "lower alkynylene," which is an unsubstituted branched- or straight-chain alkynylene having 2 to 3 carbons.

"Aryl" refers to an optionally substituted aromatic group with at least one ring having a conjugated pi-electron system, containing up to two conjugated or fused ring systems. Aryl includes carbocyclic aryl, heterocyclic aryl and biaryl groups, all of which may be optionally substituted. Preferably, the aryl is either optionally substituted phenyl, optionally substituted pyridyl, optionally substituted benzothiopyranyl, optionally substituted carbazole, optionally substituted naphthyl, optionally substituted tetrahydronaphthyl.

Different substituents are preferred for the Structure I left hand $R_1$ aryl and the Structure I $R_5$ right hand aryl. Preferably, the aryl has no more than five independently selected substituents.

Preferably, when $R_1$ is an aryl, the aryl is either optionally substituted phenyl, optionally substituted pyridyl, optionally substituted benzothiopyranyl, optionally substituted carbazole, optionally substituted naphthyl, or optionally substituted tetrahydronaphthyl. Preferred, $R_1$ substituents are each independently selected from the group consisting of: unsubstituted alkyl, unsubstituted alkenyl, halogen, alkoxy, lower haloalkyl, lower haloalkoxy, methylene dioxy, unsubstituted aryl, unsubstituted cycloalkyl, OH, SH, CN, NO, NO$_2$, NH$_2$, methylene dioxy, CH=NNHC(O)NH$_2$, CH=NNHC(S)NH$_2$, CH$_2$O-unsubstituted alkyl, C(O) unsubstituted alkyl, C(O)NH$_2$, C(O)NH-unsubstituted alkyl, C(O)N(unsubstituted alkyl)$_2$, C(O)OH, C(O)O-unsubstituted alkyl, NH-unsubstituted alkyl, N(unsubstituted alkyl)$_2$, NHC(O)unsubstituted aryl, NHC(O)unsubstituted alkyl, N=N-unsubstituted aryl, NHC(O)NH$_2$, N(unsubstituted alkyl)C(O)unsubstituted alkyl, NHC(S)unsubstituted alkyl, N(unsubstituted alkyl)C(S) unsubstituted alkyl, NHS(O)unsubstituted alkyl, N(unsubstituted alkyl)S(O)unsubstituted alkyl, NS(O)$_2$ aryl, OC(O)unsubstituted alkyl, OCH$_2$C(O)OH, OC(S) unsubstituted alkyl, S(O)unsubstituted alkyl, SC(O) unsubstituted alkyl, S-unsubstituted alkyl, S-unsubstituted haloalkyl, SO$_2$-unsubstituted alkyl, SO$_2$-unsubstituted haloalkyl, S(O)$_2$NH$_2$, S(O)$_2$NH-unsubstituted alkyl, and S(O)$_2$N(unsubstituted alkyl)$_2$.

Preferred $R_1$ aryl substituents are each independently selected from the group consisting of: alkoxy, methylene dioxy, N(CH$_3$)$_2$, C(O)OCH$_3$, phenyl, lower-haloalkyl, S-unsubstituted alkyl, lower-haloalkoxy, unsubstituted alkyl, unsubstituted alkenyl, halogen, SH, CN, NO$_2$, NH$_2$, OH and sulfamoyl. More preferably, each $R_1$ aryl substituent is independently selected from the group consisting of: unsubstituted C$_1$–C$_7$ alkyl, C$_1$–C$_7$ alkoxy, lower haloalkoxy, CF$_3$, F, Cl, Br, CN, NO$_2$ and sulfamoyl.

In another preferred embodiment, $R_1$ is either 2-CN-phenyl, 2,3-dichloro phenyl, 2-nitro-phenyl, 2-cyano-3-chloro-phenyl, or 2,3-dichloro-4-sulfamoyl-phenyl.

$R_5$ right hand aryl substituents are each independently selected from the substituents described above for alkenyl. In a preferred embodiment, the $R_5$ aryl substituents are each independently selected from the group consisting of: methoxy, lower alkyl, lower haloalkoxy, CFH$_2$, CHF$_2$, CF$_3$, OCH$_2$CF$_3$, F, Cl, Br, I, OH, SH, CN, NO$_2$, NH$_2$, methylene dioxy, NH-lower alkyl, N(lower alkyl)$_2$, C(O)lower alkyl, S-lower alkyl, S(O)lower alkyl, S(O)$_2$lower alkyl, OC(O) lower alkyl, SC(O)lower alkyl, OC(S)lower alkyl, NHC(O) lower alkyl, N(lower alkyl)C(O)lower alkyl, NHC(S)lower alkyl, N(lower alkyl)C(S)lower alkyl, NHS(O)lower alkyl, N(lower alkyl)S(O)lower alkyl, C(O)OH, C(O)O-lower alkyl, C(O)NH$_2$, C(O)NH-lower alkyl, C(O)N(lower alkyl)$_2$, S(O)$_2$NH$_2$, S(O)$_2$NH-lower alkyl, and S(O)$_2$N(lower alkyl)$_2$.

In another preferred embodiment, $R_5$ aryl substituents are each independently selected from the group consisting of: methylene dioxy, methoxy, lower-haloalkyl, S-lower alkyl, lower-haloalkoxy, lower alkyl, halogen, SH, CN, OH, Cl, F, and Br. Preferred halogens are Cl, F, and Br.

"Carbocyclic aryl" refers to an aromatic ring or ring system having all carbon atoms. The carbon atoms are optionally substituted.

"Cycloalk" refers to an optionally substituted cyclic alkyl or an optionally substituted non-aromatic cyclic alkenyl and includes monocyclic and multiple ring structures such as bicyclic and tricyclic. The cycloalk has 3 to 15 carbon atoms, preferably, 5 to 12 carbon atoms. Optional substituents for the cycloalk are each independently selected from the group described above for alkenyl. Preferably, no more than three substituents are present. More preferably, the cycloalk is unsubstituted, even more preferably it is an unsubstituted cyclic alkyl. Preferred cycloalkyl groups include cyclohexyl and adamantyl.

"Haloalk" refers to substituted alkyl or substituted alkenyl, having no more than 4 carbons, where the substituents are halogens and at least one halogen is present. Preferably, the haloalk is an alkyl 1 to 3 carbons in length and the halogens are each independently either Cl or F, more preferably the alkyl has 2 carbons, more preferably the haloalkyl is a lower haloalkyl which has 1 carbon.

"Heterocyclic aryl" refers to an aryl having 1 to 3 heteroatoms as ring atoms in the aromatic ring and the remainder of the ring atoms are carbon atoms. Suitable heteroatoms include oxygen, sulfur, and nitrogen. Examples of heterocyclic aryl include indolyl, pyridyl, quinolinyl, and isoquinolinyl.

"Longer-length alk" refers to either longer-length alkyl, longer-length alkenyl, or longer-length alkynyl; preferably, longer-length alkyl or longer-length alkenyl. More preferably a longer-length alk is 4 to 20 carbon atoms.

"Longer-length alkenyl" refers to an optionally substituted hydrocarbon group containing at least one carbon-carbon double bond between the carbon atoms, and which contains 2–20 carbon atoms joined together. Preferably, the longer-length alkenyl is 4 to 20 carbon atoms. The longer-length alkenyl hydrocarbon group may be straight-chain or contain one or more branches. Longer-length alkenyl substituents are each independently selected from the alkenyl substituent list described above. Preferably, the longer-length alkenyl is either unsubstituted or has one cycloalk or phenyl substituent. More preferably, the cycloalk substituent, if present, is unsubstituted, and more preferably the cycloalk substituent, if present, is either cyclohexyl or adamantyl.

"Longer-length alkyl" refers to an optionally substituted hydrocarbon group joined by single carbon-carbon bonds and which contains 1–20 carbon atoms joined together. Preferably, the longer-length alkyl is 4 to 20 carbon atoms. The longer-length alkyl hydrocarbon group may be straight-chain or contain one or more branches. Longer-length alkyl substituents are each independently selected from the alkenyl substituent list described above. Preferably, the longer-length alkyl is either unsubstituted or has one cycloalk or phenyl substituent. More preferably, the cycloalk substituent, if present, is unsubstituted, and more preferably the cycloalk substituent, if present, is either cyclohexyl or adamantyl.

"Longer-length alkynyl" refers to an optionally substituted hydrocarbon group containing at least one carbon-carbon triple bond between the carbon atoms, and which contains 2–20 carbon atoms joined together. Preferably, the longer-length alkynyl is 4 to 20 carbon atoms. The longer-length alkynyl hydrocarbon group may be straight-chain or contain one or more branches. Longer-length alkynyl substituents are each independently selected from the alkenyl substituent list described above. Preferably, the longer-length alkynyl is either unsubstituted or has one cycloalk or phenyl substituent substituent. More preferably, the cycloalk substituent, if present, is unsubstituted, and more preferably the cycloalk substituent, if present, is either cyclohexyl or adamantyl.

"Haloalkoxy" refers to oxygen joined to a "haloalk" Preferably, the haloalkoxy is a "lower-haloalkoxy," which is an oxygen joined to a lower-haloalkyl.

A. α,α-Disubstituted β-Phenethylamine Derivatives

More preferred calcilytic compounds are Structure I derivatives where $R_1$, $R_2$, $R_3$, $R_4$, $R_6$, Z, $Y_1$ and $Y_2$ are as described above for Structure I α,α-disubstituted arylalkylamine derivatives, including preferred groups (see, Section II, supra); and $R_5$ is either phenyl substituted with one to four independently selected substituents or an optionally substituted naphthyl having up to four independently selected substituents. $R_5$ substituents are provided in Section II, supra., including preferred embodiments. More preferably $R_5$ is either a substituted phenyl comprising a substituent in a meta or para position, more preferably, the substituent present in a meta or para position is either methyl, ethyl, isopropyl, methoxy, Cl, F, Br, or lower haloalkoxy.

The activity of different calcilytic compounds was measured using the Calcium Receptor Assay described below. Examples of compounds having an $IC_{50} \leq 50$ μM include compounds 1, 9, 17, 25, 29, 42, 56, 79, 90, 101 and 164; examples of preferred compounds having an $IC_{50} < 10$ μM include compounds 2, 3, 7, 8, 26, 27, 32, 33, 35, 37, 39, 41, 45, 48, 49, 59, 61, 66, 68, 71, 75, 93, 98, 103, 104, 110, 111, 114, 123, 124, 125, 128, 132, 144, 147, 152, 155, 158, 161, 162, 169 and 170; and examples of more preferred compounds having an $IC_{50} <$ than 1 μM include compounds 5, 6, 19, 20, 21, 28, 38, 40, 43, 44, 46, 47, 50, 51, 63, 64, 65, 67, 69, 72, 74, 96, 105, 106, 109, 112, 113, 115, 116, 117, 118, 119, 120, 121, 122, 126, 127, 129, 130, 131, 133, 134, 135, 136, 137, 138, 139, 140, 141, 142, 143, 145, 146, 148, 149, 150, 151, 153, 154, 156, 157, 159, 160, 163, 165, 166, 167, and 168.

B. Structure II Compounds

Structure II compounds have the following structure:

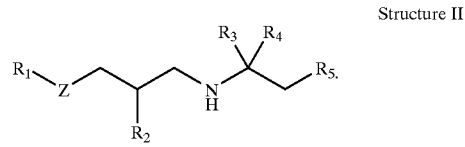

Structure II

In one embodiment $R_1$, $R_2$, $R_3$, and $R_4$ are as described above for Structure I α,α-disubstituted arylalkylamine derivatives, including preferred groups (see, Section II, supra); and $R_5$ is either an optionally substituted naphthyl having one to four substituents independently selected from the group consisting of methyl, ethyl, isopropyl, methoxy, Cl, F, Br, or lower haloalkoxy, preferably the naphthyl is unsubstituted; or a substituted phenyl having one to four substituent with at least one substituent in a meta or para position selected from the group consisting of: lower alkyl, methoxy, Cl, F, Br, and lower haloalkoxy, more preferably a methoxy is present in the para or meta position; even more preferably, the remaining $R_5$ substituents are independently selected from the group consisting of: methoxy, lower-haloalkyl, S-lower alkyl, lower-haloalkoxy, lower alkyl, halogen, SH, CN, OH, Cl, F, and Br.

provided that $R_1$ is not 6-CN-2-pyridyl; and further provided that if $R_5$ is 3,4 dimethoxy-phenyl, then $R_1$ is not $CH_3(CH_2)_5O$-phenyl; 2-cyclopentyl-phenyl; 2-Cl-phenyl; 2-CN-phenyl; 2-(3-furanyl)phenyl; or 4-(1,2,-benzisothiazol); preferably, $R_5$ is not 3,4 dimethoxy phenyl;

further provided that if $R_5$ is 4-methoxy-phenyl, then $R_1$ is not 2-cyclopentyl-phenyl; 2-$CH_3$-phenyl; 2-benzyl-phenyl; 3-$CH_3$, 4-$CH_3SO_2$-phenyl; or 4-(1,2,-benzisothiazol);

further provided that if $R_5$ s is 4-Cl-phenyl, then $R_1$ is not 2-$CH_3$-phenyl, 5-iso-propyl-phenyl; 2-$CH_3$-phenyl; 4-$CH_3$-phenyl; phenyl; 2-Cl-phenyl; 4-Cl-phenyl; 2-methoxy, 4-$CH_3CHCH$-phenyl; 3,4 $CH_3$-phenyl; 2,4 $CH_3$-phenyl; 2,3 $CH_3$-phenyl; 2-iso-propyl, 5-$CH_3$-phenyl; pridyl; or 1-imidazole; 4-(1,2,-benzisothiazol); preferably, $R_4$ is either not 4-Cl, or $R_4$ is 3,4 dichlorophenyl; and further provided that if $R_5$ s is 3,5, dimethyl, 4-methoxy-phenyl, then $R_1$ is not 4-$CH_3$, 6-CN-2-pyridyl; or thiophenecarboxamide; preferably, $R_5$ is not 3,5, dimethyl, 4-methoxy-phenyl.

In another embodiment, $R_2$, $R_3$, and $R_4$ are as described above for Structure I α,α-disubstituted arylalkylamine derivatives, including preferred groups (see, Section II, supra);

$R_5$ is either an optionally substituted naphthyl having one to four substituents independently selected from the group consisting of methyl, ethyl, isopropyl, methoxy, Cl, F, Br, and lower haloalkoxy, preferably the naphthyl is unsubstituted; or a substituted phenyl having one to four substituent with at least one substituent in a meta or para position selected from the group consisting of: methyl, ethyl, isopropyl, methoxy, Cl, F, Br, and lower haloalkoxy, more preferably a methoxy is present in the para or meta position; even more preferably, the remaining $R_5$ substituents are independently selected from the group consisting of: methoxy, lower-haloalkyl, S-lower alkyl, lower-haloalkoxy, lower alkyl, halogen, SH, CN, OH, Cl, F, and Br; and $R_1$ is either 2-CN-phenyl, 2,3-dichloro phenyl, 2-nitrophenyl, 2-cyano-3-chloro-phenyl, 2,3-dichloro-4-sulfamoyl-phenyl, an optionally substituted pyridyl, an optionally substituted benzothiopyranyl, or an optionally substituted carbazole, where the optionally present substituents for the pyridyl, benzothiopyranyl, and carbazole as described in Section II supra, for aryl $R_1$ substituents, including preferred substituents, and are even more preferably independently selected from the group consisting of: methoxy, lower-haloalkyl, S-lower alkyl, lower-haloalkoxy, lower alkyl, halogen, SH, CN, OH, Cl, F, Br and sulfamoyl.

C. $R_2$-group Stereochemistry

The different calcilytic compounds described herein can have different stereochemistry around different groups. In an embodiment of the present invention the Structure I compounds have the following absolute configuration structure with respect to $R_2$:

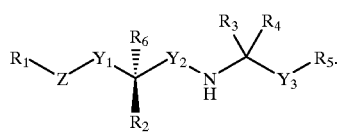

III. PHARMACEUTICAL COMPOSITION

The calcilytic compounds described herein can be formulated as a pharmaceutical composition to facilitate the administration of the compound to a patient. Preferred formulations contain a pharmaceutically acceptable carrier and a calcilytic compound as described in Section II, supra., including the different embodiments.

Examples of suitable carriers are provided below, in Section V, "Administration," and include calcium carbonate, calcium phosphate, lactose, glucose, sucrose, gelatin, vegetable oils, polyethylene glycols and physiologically compatible solvents.

IV. TREATMENT OF DISEASES OR DISORDERS

Compounds inhibiting calcium receptor activity can be used to confer beneficial effects to patients suffering from a variety of diseases or disorders. Diseases or disorders which can be treated using a calcilytic compound are known in the art and can be identified using the present application as a guide. For example, diseases or disorders can be identified based on the functional responses of cells regulated by calcium receptor activity.

Diseases and disorders which can be treated using the calcilytic compounds described herein include those due to different cellular defects related to calcium receptor activity in different cells, such as a defective calcium receptor or an abnormal number of calcium receptors, a defective intracellular protein acted on by a calcium receptor, or a defective protein or an abnormal number of proteins acting on a calcium receptor.

Functional responses of cells regulated by the calcium receptor are known in the art, including PTH secretion by parathyroid cells, calcitonin secretion by C-cells, bone resorption by osteoclasts, and $Ca^{2+}$ secretion by kidney cells. Such functional responses are associated with different diseases or disorders.

For example, isolated osteoclasts respond to increases in the concentration of extracellular $Ca^{2+}$ with corresponding increases in $[Ca^{2+}]_i$ arising partly from the mobilization of intracellular $Ca^{2+}$. Increases in $[Ca^{2+}]_i$ in osteoclasts are associated with the inhibition of bone resorption.

Renin secretion from juxtaglomerular cells in the kidney is depressed by increased concentrations of extracellular $Ca^{2+}$. Extracellular $Ca^{2+}$ causes the mobilization of intracellular $Ca^{2+}$ in these cells. Other kidney cells respond to extracellular $Ca^{2+}$ as follows: elevated $Ca^{2+}$ inhibits formation of 1,25(OH)$_2$-vitamin D by proximal tubule cells, stimulates production of calcium-binding protein in distal tubule cells, and inhibits tubular reabsorption of $Ca^{2+}$ and $Mg^{2+}$ in the thick ascending limb of Henle's loop (MTAL), and reduces vasopressin action in the cortical collecting duct.

Other examples of functional responses affected by extracellular $Ca^{2+}$ include promoting differentiation of intestinal goblet cells, mammary cells, and skin cells; inhibiting atrial natriuretic peptide secretion from cardiac atria; reducing cAMP accumulation in platelets; altering gastrin and glucagon secretion; acting on perivascular nerves to modify cell secretion of vasoactive factors; and affecting cells of the central nervous and peripheral nervous systems.

Diseases and disorders which might be treated or prevented, based upon the affected cells, include bone and mineral-related diseases or disorders; hypoparathyroidism; those of the central nervous system such as seizures, stroke, head trauma, spinal cord injury, hypoxia-induced nerve cell damage, such as occurs in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney, such as syndrome of inappropriate ADH secretion (SIADH), cirrhosis, congestive heart failure, and nephrosis; hypertension; preventing and/or decreasing renal toxicity from cationic antibiotics (e.g., aminoglycoside antibiotics); gut motility disorders such as diarrhea and spastic colon; GI ulcer diseases; GI diseases with excessive calcium absorption such as sarcoidosis; autoimmune diseases and organ transplant rejection; squamous cell carcinoma; and pancreatitis.

While calcilytic compounds of the present invention will typically be used to treat human patients, they may also be used to treat similar or identical diseases or disorders in other warm-blooded animal species, such as other primates, farm animals such as swine, cattle, and poultry; and sports animals and pets such as horses, dogs and cats.

Preferably, calcilytic compounds are used in the treatment of bone and mineral-related diseases or disorders. Bone and mineral-related diseases or disorders comprise a diverse class of disorders affecting nearly every major organ system in the body. Examples of bone and mineral-related diseases or disorders include osteosarcoma, periodontal disease, fracture healing, osteoarthritis, rheumatoid arthritis, Paget's disease, humoral hypercalcemia malignancy, and osteoporosis. More preferably, calcilytic compounds are used to treat osteoporosis, a disease characterized by reduced bone density and an increased susceptibility to fractures. Osteoporosis is associated with aging, especially in women.

One way of treating osteoporosis is by altering PTH secretion. PTH can have a catabolic or an anabolic effect on bone. Whether PTH causes a catabolic effect or an anabolic effect seems to depend on how plasma levels of PTH are altered. When plasma levels of PTH are chronically elevated, as in hyperparathyroid states, there is a net loss of bone. In contrast, intermittent increases in plasma PTH levels, as achieved by administration of exogenous hormone, result in new bone formation. Anabolic action of PTH on bone is described, for example, by Dempster et al., *Endocrin. Rev.* 14:690–709, 1993.

As demonstrated by the Examples provided below, calcilytic compounds stimulate secretion of PTH. Such calcilytic compounds can be used to increase bone formation in a patient, for example, by intermittent dosing, thus achieving intermittent increases in the circulating levels of PTH.

V. ADMINISTRATION

The calcilytic compounds described by the present invention can be formulated for a variety of modes of administration, including systemic and topical or localized administration. Techniques and formulations generally may be found in *Remington's Pharmaceutical Sciences*, $18^{th}$ ed., Mack Publishing Co., Easton, Pa, 1990 (hereby incorporated by reference herein).

Suitable dosage forms, in part, depend upon the use or the route of entry, for example, oral, transdermal, transmucosal, or by injection (parenteral). Such dosage forms should allow the compound to reach a target cell whether the target cell is present in a multicellular host or in culture. For example, pharmacological compounds or compositions injected into the blood stream should be soluble. Other factors are known in the art, and include considerations such as toxicity and dosage forms which retard the compound or composition from exerting its effect.

Compounds can also be formulated as pharmaceutically acceptable salts and complexes thereof. Pharmaceutically acceptable salts are non-toxic salts in the amounts and concentrations at which they are administered. The preparation of such salts can facilitate the pharmacological use by altering the physical characteristics of the compound without preventing it from exerting its physiological effect. Useful alterations in physical properties include lowering the melting point to facilitate transmucosal administration and increasing the solubility to facilitate administering higher concentrations of the drug.

The pharmaceutically acceptable salt of the different compounds may be present as a complex. Examples of complexes include an 8-chlorotheophylline complex (analogous to, e.g., dimenhydrinate:diphenhydramine 8-chlorotheophylline (1:1) complex; Dramamine) and various cyclodextrin inclusion complexes.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, $18^{th}$ ed., Mack Publishing Co., Easton, Pa, p. 1445, 1990. Such salts can be prepared using the appropriate corresponding bases.

Pharmaceutically acceptable salts can be prepared by standard techniques. For example, the free-base form of a compound is dissolved in a suitable solvent, such as an aqueous or aqueous-alcohol in solution containing the appropriate acid and then isolated by evaporating the solution. In another example, a salt is prepared by reacting the free base and acid in an organic solvent. (See, e.g., PCT/US92/03736, hereby incorporated by reference herein.)

Carriers or excipients can also be used to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution and dextrose.

The calcilytic compounds can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various calcilytic compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art. Generally, it is an amount between about 0.1 and 50 mg/kg, preferably 0.01 and 20 mg/kg of the animal to be treated.

VI. EXAMPLES

The examples provided below, like the other examples provided herein, are not intended to limit the claimed invention, but rather illustrate different aspects and embodiments of the present invention.

Example 1
Calcium Receptor Inhibitor Assay

This example illustrates the use of the Calcium Receptor Inhibitor Assay. Calcilytic activity was measured by determining the $IC_{50}$ of the test compound for blocking increases of intracellular $Ca^{2+}$ elicited by extracellular $Ca^{2+}$ in HEK 293 4.0–7 cells stably expressing the human calcium receptor. HEK 293 4.0–7 cells were constructed as described by Rogers et al., *J. Bone Miner. Res.* 10 Suppl. 1:S483, 1995 (hereby incorporated by reference herein). Intracellular $Ca^{2+}$ increases were elicited by increasing extracellular $Ca^{2+}$ from 1 to 1.75 mM. Intracellular $Ca^{2+}$ was measured using fluo-3, a fluorescent calcium indicator.

The procedure was as follows:

1. Cells were maintained in T-150 flasks in selection media (DMEM supplemented with 10% fetal bovine serum and 200:g/mL hygromycin B), under 5% $CO_2$:95% air at 37° C. and were grown up to 90% confluency.

2. The medium was decanted and the cell monolayer was washed twice with phosphate-buffered saline (PBS) kept at 37° C. After the second wash, 6 mL of 0.02% EDTA in PBS was added and incubated for 4 minutes at 37° C. Following the incubation, cells were dispersed by gentle agitation.

3. Cells from 2 or 3 flasks were pooled and pelleted (100×g). The cellular pellet was resuspended in 10–15 mL of SPF-PCB+ and pelleted again by centrifugation. This washing was done twice.

Sulfate- and phosphate-free parathyroid cell buffer (SPF-PCB) contains 20 mM Na-Hepes, pH 7.4, 126 mM NaCl, 5 mM KCl, and 1 mM $MgCl_2$. SPF-PCB was made up and stored at 4° C. On the day of use, SPF-PCB was supplemented with 1 mg/mL of D-glucose and 1 mM $CaCl_2$ and then split into two fractions. To one fraction, bovine serum albumin (BSA; fraction V, ICN) was added at 5 mg/mL (SPF-PCB+). This buffer was used for washing, loading and maintaining the cells. The BSA-free fraction was used for diluting the cells in the cuvette for measurements of fluorescence.

4. The pellet was resuspended in 10 mL of SPF-PCB+ containing 2.2:M fluo-3 (Molecular Probes) and incubated at room temperature for 35 minutes.

5. Following the incubation period, the cells were pelleted by centrifugation. The resulting pellet was washed with SPF-PCB+. After this washing, cells were resuspended in SPF-PCB+ at a density of 1–2×106 cells/mL.

6. For recording fluorescent signals, 300:L of cell suspension were diluted in 1.2 mL of SPF buffer containing 1 mM $CaCl_2$ and 1 mg/mL of D-glucose. Measurements of fluorescence were performed at 37° C. with constant stirring using a spectrofluorimeter. Excitation and emission wavelengths were measured at 485 and 535 nm, respectively. To calibrate fluorescence signals, digitonin (5 mg/mL in ethanol) was added to obtain $F_{max}$, and the apparent $F_{min}$ was determined by adding Tris-EGTA (2.5 M Tris-Base, 0.3 M EGTA). The concentration of intracellular calcium was calculated using the following equation:

$$\text{Intracellular calcium} = (F - F_{min}/F_{max}) \times Kd; \text{ where } Kd = 400 \text{ nM}.$$

7. To determine the potential calcilytic activity of test compounds, cells were incubated with test compound (or vehicle as a control) for 90 seconds before increasing the concentration of extracellular $Ca^{2+}$ from 1 to 2 mM. Calcilytic compounds were detected by their ability to block, in a concentration-dependent manner, increases in the concentration of intracellular $Ca^{2+}$ elicited by extracellular $Ca^{2+}$.

In general, those compounds having lower $IC_{50}$ values in the Calcium Receptor Inhibitor Assay are more preferred compounds. Compounds having an $IC_{50}$ greater than 50 $\mu$M were considered to be inactive. Preferred compounds are those having an $IC_{50}$ 10–50 $\mu$M, more preferred compounds have an $IC_{50}$ 1–10 $\mu$M, and most preferred compounds have an $IC_{50}$ less than 1 $\mu$M.

Examples of compounds having an $IC_{50}$ greater than 50 $\mu$M include compounds 22, 24, 34, 36, 52, 53, 54, 55, 58, 60, 62, 70, 84, 92, 99, and 102.

Example 2
Adrenergic Receptor Activity

Structure I α,α-disubstituted arylalkylamine derivatives include compounds which have both calcilytic activity and β-adrenergic receptor activity. If desired, β-adrenergic activity can be reduced using appropriate functional groups and structural modifications. Modifications which can be carried out to reduce β-adrenergic receptor activity include using alternative $R_2$ groups and using absolute stereochemistry opposite to that which occurs in active β-adrenergic receptor antagonists, which provides compounds corresponding to the R enantiomer when $R_2$ is OH. β-adrenergic receptor activity and binding to the β-adrenergic receptor can be measured using standard techniques. For example, see Riva et al., *Mol. Pharmacol.* 36:201–210, 1989.

In one embodiment of the present invention the calcilytic compounds have an $IC_{50} \geq 1.0$ nM, at the β-adrenergic receptor as measured using the "β-Adrenergic Receptor Binding Assay" described below. In other embodiments, using the β-Adrenergic Receptor Assay calcilytic compounds have an $IC_{50} \geq 1.0$ μM, and $IC_{50} \geq 10.0$ μM.

The "β-Adrenergic Receptor Binding Assay" is carried out as follows: Incubations are performed in polypropylene reaction tubes in a 37° C. water bath. To each tube 50 μL of test sample is added, followed by 300 μL of assay buffer (50 mM Tris-HCl, pH 7.5), and 50 μL of 20 nM [$^3$H]-dihydroalprenolol. The binding reaction is initiated by the addition of 100 μL of 3.75 mg/mL well-washed rat cortex membranes in assay buffer, and allowed to incubate at 37° C. for 30 minutes. Non-specific binding is determined in the presence of 10 μM alprenolol. The final concentration of reactants is: 2 nM [$^3$H]-dihydroalprenolol, and 75 mg/mL rat cortex membrane in a reaction volume of 0.5 mL.

The binding reaction is terminated by rapid filtration with ice-cold assay buffer onto GF/C filters (Brandel, Gaithersburg, Md.) which have been soaked for 15 minutes in assay buffer. The reaction is first diluted with 3 mL of cold assay buffer (4° C.), then aspirated onto the filter followed by 3×3 mL washes. Filter disks are placed in 7-mL polypropylene scintillation vials with 5 mL of ScintiSafe 50% (Fisher Scientific, Pittsburgh, Pa.), and counted overnight.

Example 3
Stimulation of PTH Secretion

This example illustrates the ability of different calcilytic compounds to exert a biological effect on PTH secretion. PTH secretion was determined using dissociated bovine parathyroid cells as described below for Compounds 32, 33, and 38. Compounds 32, 33, and 38 all stimulated PTH secretion with an $EC_{50}$ of less than 10 μM.

Stimulation of PTH secretion was assayed as follows:
Preparation of Dissociated Bovine Parathyroid Cells Parathyroid cell buffer (PCB) contains (mM): NaCl, 126; KCl, 4; MgSO$_4$, 1; K$_2$HPO$_4$/KH$_2$PO$_4$, 0.7; Na-Hepes, pH 7.45, and variable amounts of CaCl$_2$ as specified (reagent grade). PCB was typically supplemented with bovine serum albumin (BSA fraction V; ICN Biomedicals, Inc., Costa Mesa, Calif. ; catalog #81–003) and 1 mg/mL of D-glucose (reagent grade) as indicated. Percoll purification buffer was prepared immediately before use by mixing 8 mL of Percoll (Pharmacia LKB, Alameda, Calif.; catalog #17–0891–01) and 7 mL of a twice-concentrated PCB solution without phosphate and containing 2 mM CaCl$_2$.

Parathyroid glands were obtained from calves within minutes of slaughter at an abattoir and shipped via overnight express on ice in PCB containing 1.25 mM CaCl$_2$. The glands were trimmed and minced in ice-cold PCB containing 1.25 mM CaCl$_2$, 1 mg/mL of D-glucose, and 2% BSA. Dissociated cells were obtained by collagenase digestion by vigorously shaking the minced tissue at 37° C. in PCB containing 0.5 to 1.0% Collagenase P (Boehringer Mannheim, Indianapolis, Ind.; catalog #1249 002), 2 to 5 units of deoxyribonuclease (Sigma, St. Louis, Mo.; catalog #D-0876), 1 mg/mL of D-glucose, and 1.25 mM CaCl$_2$ (reagent grade). The cell suspension was triturated at 30 minute intervals using 25- and 10-mL pipettes as the minced tissue was digested and the cells were dispersed.

Cells were pooled at 1-hour intervals by filtering the cell suspension through a 250-μm Nitex screen into 15-mL polystyrene centrifuge tubes and spinning at 100×g for 5 minutes at 22° C. The pooled cell pellet was resuspended in Percoll purification buffer and purified by centrifugation at 14,500×g for 20 minutes at 4° C. Dissociated parathyroid cells equilibrated within a buoyant density of 1.048–1.062 above a dense band of red blood cells and below a diffuse band that contains adipocytes, strands of collagen, and damaged cells.

The dissociated parathyroid cells were removed with a sterile pipette and washed 3 to 4 times under sterile conditions in a 1:1 mixture of Ham's F-12 and Dulbecco's modified Eagle's medium (F-12/DMEM, Sigma, St. Louis, Mo.; catalog #D 8900) supplemented with 0.5% BSA, 100 U/mL of penicillin, 100 μg/mL of streptomycin (Gibco BRL, Grand Island, N.Y.; catalog #15140–031), and 20 μg/mL of gentamicin (Sigma, St. Louis, Mo.; catalog #G 1397).

The cells were finally resuspended in F-12/DMEM supplemented with lower antibiotic concentrations (10 U/mL of penicillin, 10 μg/mL of streptomycin, and 4 μg/mL of gentamicin). This latter medium lacks serum and contained ITS$^+$ (insulin, transferrin, selenous acid, BSA, and linoleic acid; Collaborative Biomedical Products, Bedford, Ma.; catalog #40352).

Cells were incubated in T-75 flasks at 37° C. in a humid atmosphere of 5% CO$_2$ in air. Parathyroid cells were collected for use by decanting the flasks after 18 to 24 hours in primary culture. The concentrations of gentamicin and streptomycin used here are considerably below the $EC_{50}$ for mobilization of intracellular calcium (150 and 600 μM, respectively).

Measurement of Parathyroid Hormone (PTH) Secretion

Sulfate, phosphate-free parathyroid cell buffer (SPF-PCB) contains (mM): NaCl, 126; KCl, 5; MgCl$_2$, 1; Na-Hepes, pH 7.45, and variable amounts of CaCl$_2$ as specified (reagent grade). SPF-PCB was typically supplemented with bovine serum albumin (BSA fraction V; ICN Biomedicals, Inc., Costa Mesa, Calif.; catalog #81–003) and 1 mg/mL of D-glucose (reagent grade) as indicated.

Incubations were performed in triplicate in 12×75 mm polypropylene or polystyrene tubes to which were added 2.5 μL of test compound. The tubes were kept on ice until the drug additions were completed, then were transferred to a water bath at 37° C., and the reactions were initiated by the addition of 0.2 mL of a suspension of dissociated cells at a density of 1 to 2 million cells/mL in SPF-PCB containing 0.5 mM Ca$^{2+}$, 1 mg/mL of D-glucose, and 0.1% BSA. Incubation was for 30 minutes and the reaction was terminated by placing the tubes on ice. Cells were pelleted by gentle centrifugation (500×g for 10 minutes at 4° C.) and 0.1 mL of supernatant was removed and stored at −20° C.

Amino-terminal bovine PTH was measured by radioimmunoassay (RIA) using goat anti-hPTH antiserum H$_2$, HPLC-purified $^{125}$I-hPTH (1-34) and bovine PTH (1-84) standards. Serial dilutions of bPTH standards (1,000 pg/25 μL to 3.8 pg/25 μL) were done in 50 mM Tris, pH 7.4, containing 0.5 mM Na azide and 2% bovine serum albumin (diluent). Standards and samples were incubated for 2–3 days at 4° C. in the presence of antiserum after which 1,500–2,000 cpm label/tube was added. After an additional incubation for 1 to 2 days at 4° C., dextran-coated charcoal was added to separate bound vs. free label. The contents of each tube were mixed and the charcoal was pelleted by centrifugation. The supernatants were decanted into 12×75 mm polystyrene tubes and counted in a Packard Cobra gamma counter.

Example 4

General Procedures for the Preparation of Calcilytic Compounds

The calcilytic compounds described by the present invention can be prepared using standard techniques. For example, an overall strategy for preparing preferred compounds described herein can be carried out as described in this section. The examples which follow illustrate the synthesis of specific compounds. Using the protocols described herein as a model, one of ordinary skill in the art can readily produce other Structure I compounds.

All reagents and solvents were obtained from commercial vendors. Starting materials (e.g., amines and epoxides) were synthesized using standard techniques and procedures. GC/EI-MS (Gas Chromatographic/Electron-Impact Mass Spectrometric) analyses were performed on HP-5890 Series II gas chromato-graphs equipped with HP-Ultra-2 or HP-5MS columns (30 mm×0.25 mm ID) and HP-5971 or HP-5972 Mass Selective Spectrometric Detectors (MSD's) were used. MPLC (Medium-Pressure Liquid Chromatography) separations were carried out on silica gel (400 mesh) using an FMI pump, ISCO UV-6 detector (254 nm) and FOXY 200 fraction collector. HPLC (High Performance Liquid Chromatography) was performed using RAININ HP-XL pumps and Dynamix UV-1 detectors (254 mm).

Examples of specific separation conditions and details are given in the individual experimental descriptions provided in the examples below. Chiral HPLC separations were carried out using a Beckman System Gold HPLC and UV detector (254 nm) on Diacel® ChiralCel OD columns (Chiral Technologies, Inc., Exton, Pa. 19341).

NMR (Nuclear Magnetic Resonance) spectroscopy was performed on a Varian Gemini 300 spectrometer. Proton and carbon spectra were taken at 300 MHz and 75 MHz, respectively. NMR resonances are reported in ppm relative to tetramethylsilane (TMS) with the following descriptors for the observed multiplicities: s (singlet), d (doublet), t (triplet), q (quartet), dd (doublet of doublets) and m (multiplet). $J_{AB}$ coupling constants are reported in Hz. Elemental analyses were performed and FT-IR data were acquired by Oneida Research Services, Inc., Whitesboro, N.Y. 13492.

A general procedure used to synthesize many of the compounds was carried out as follows: A solution of glycidyl ether (i.e., 1,2-epoxy-3-phenoxypropane, 1 mmol) and excess amine (typically 1,1-dimethyl-2-(4-methoxyphenyl) ethylamine, 1.5 mmol) in absolute ethanol (2 mL) is stirred overnight at 50–60° C. The product is purified by one of three general methods: (1) conversion to the hydrochloride salt, followed by Reversed-Phase High-Performance Liquid Chromatography (RP-HPLC, 0.1% HCl/acetonitrile); (2) conversion to the hydrochloride salt, followed by recrystallization from water-methanol or acetonitrile; and (3) purification by normal-phase chromatography (column chromatography or preparative, thin-layer chromatography (TLC)). Hydrochloride salts were also prepared by treatment of the corresponding free base in diethyl ether with 1M HCl (in diethyl ether).

Example 5

Preparation of N-[2-Hydroxy-3-(1-naphthoxy)propyl]-1,1-dimethyl-2-(4-fluorophenyl)ethylamine Hydrochloride, Compound 2

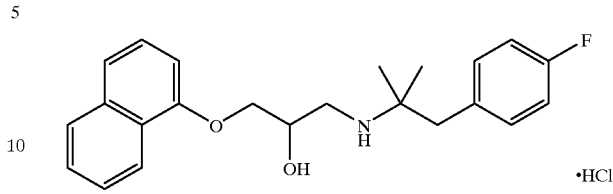

A stirred suspension of sodium hydride (4.0 g of 60% NaH in mineral oil, 100 mmol) in dimethylformamide (DMF, 100 ml) was treated with 1-naphthol (14.42 g, 100 mmol). After stirring for 1 hour at ambient temperature (room temperature), the reaction was treated with epichlorohydrin (10.18 g, 110 mmol) and stirred for 1 hour at 100° C. The reaction was diluted with water and transferred to a separatory funnel using diethyl ether (500 ml). The organic phase was washed with 10% aqueous $NaHCO_3$ (3×200 ml), dried over anhydrous sodium sulfate, filtered, and concentrated. Kugelrohr distillation (~100 microns) yielded 1-naphthyl glycidyl ether as a clear, colorless oil: GC/EI-MS, m/z (rel. int.) 200 ($M^+$, 61), 184 (1), 169 (5), 157 (12), 144 (79), 129 (16), 115 (100), 101 (3), 89 (16).

A stirred solution of 1-naphthyl glycidyl ether (400 mg, 2 mmol) and 1,1-dimethyl-2-(4-fluorophenyl)ethylamine (334 mg, 2 mmol) in absolute ethanol (2 mL) was heated at 50–60° C. for 16 hours. Chromatography of the resulting reaction mixture through silica (5×30 cm) using a gradient of chloroform to 5% methanol in chloroform afforded the free base of the title compound: GC/EI-MS, m/z (rel. int.) 368 ($M^+1$, 1), 352 (2), 258 (100), 183 (5), 157 (4), 127 (5), 115 (18), 109 (23), 71 (30).

The free base in diethyl ether was treated with excess 1M HCl (diethyl ether). The resulting solid was recrystallized from hot acetonitrile to afford 300 mg of the title compound as a crystalline solid: $^1$H-NMR (DMF-$D_7$) δ9.9 (1H, br s), 9.5 (1H, br s), 8.33 (1H, d, J=9), 7.91 (1H, d, J=9), 7.57–7.50 (3H, m), 7.48–7.41 (3H, m), 7.19 (2H, t, J=10), 7.03 (1H, d, J=7), 6.37 (1H, br d, J=5), 4.67 (1H, br s), 4.31 (2H, br t, J=6), 3.61 (1H, br t), 3.42 (1H, br t), 3.31 (2H, s), 1.47 (3H, s), 1.46 (3H, s); $^{13}$C-NMR (DMF-$D_7$) δ161.5, 158.2, 152.2, 132.5, 130.8, 130.7, 129.7, 125.4, 124.4, 124.1, 124.5, 120.0, 118.3, 113.1, 112.8, 103.1, 68.1, 64.2, 57.9, 43.5, 40.3, 20.2.

Example 6

Preparation of N-(2-Hydroxy-3-phenoxypropyl)-1,1-dimethyl-2-(4-methoxyphenyl)ethylamine Hydrochloride, Compound 3

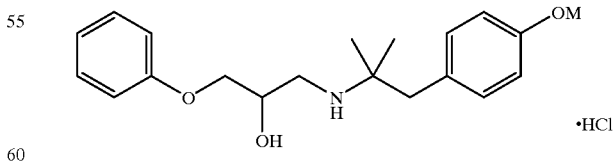

A cooled (−78° C.) solution of diisopropylamine (65 g, 642 mmol) in tetrahydrofuran (THF, 800 mL) was treated with 244 mL of 2.5 M n-butyl lithium (610 mmol) in hexane. The reaction was stirred for 30 minutes at room temperature, cooled to −78° C. and treated dropwise with isobutyric acid (26.8 g, 305 mmol) and hexamethylphosphoramide (HMPA, 54.7 g, 305 mmol). The reaction was stirred for 30 minutes at room temperature and treated with 4-methoxybenzyl chloride (43.4 g, 277 mmol). The reaction was stirred for 48 hours at room temperature and treated with 10% HCl (200 mL). The reaction was concentrated to 300 mL and diluted to 600 mL with water. The resulting solution was extracted with diethyl ether (2×300 mL) and the combined ether extracts were washed with 10% HCl (2×200 mL). The ether extract was then extracted with 1N NaOH (3×200 mL). The combined 1N NaOH washes were made acidic (pH 1) by the addition of concentrated HCl, and the resulting solution was extracted with diethyl ether (3×300 mL). The combined ether extracts were dried over anhydrous magnesium sulfate, filtered, and concentrated to afford 32.6 g of 2,2-dimethyl-3-(4-methoxyphenyl)propionic acid as an oil: GC/EI-MS, m/z (rel. int.) 208 (M+, 7), 121 (100), 91 (5), 77 (6).

Triethylamine (16.8 g, 166 mmol) and 2,2-dimethyl-3-(4-methoxyphenyl)propionic acid (32.6 g, 157 mmol) were dissolved in 30 mL of water and enough acetone to maintain solubility at 0° C. A solution of ethyl chloroformate (20.1 g, 185 mmol) in acetone (100 mL) was then added dropwise. An aqueous solution (95 mL) of sodium azide (12.9 g, 198 mmol) was then added dropwise and the resulting reaction mixture stirred 45 minutes at room temperature. The intermediate acyl azide was then extracted into toluene (200 mL). The organic extract was washed with water, dried over anhydrous magnesium sulfate, and heated at 100° C. until the evolution of nitrogen ceased (~45 min). The toluene was removed under vacuum and replaced with benzyl alcohol. The solution was then heated at 100° C. for 16 hours. The excess benzyl alcohol was removed under vacuum. The resulting benzyl carbamate was dissolved in absolute ethanol (200 mL) and reduced in the presence of palladium hydroxide (2 g) under 90 p.s.i. hydrogen for 4 hours at room temperature. The reaction was filtered and concentrated to a yellow oil. Vacuum distillation afforded 13.0 g of 1,1-dimethyl-2-(4-methoxyphenyl)ethylamine as a clear, colorless oil: GC/EI-MS, m/z (rel. int.) 180 (M+1, 1), 164 (5), 121 (25), 91 (5), 78 (19), 58 (100).

1,2-Epoxy-3-phenoxypropane (150 mg, 1 mmol) and 1,1-dimethyl-2-(4-methoxyphenyl)ethylamine (269 mg, 1.5 mmol) were used to prepare the free base of the title compound using the method of Example 5, supra. The hydrochloride salt was prepared by dilution of the reaction mixture with HCl (3 mmol) and water. Reversed-phase high-performance liquid chromatography (RP-HPLC, 0.1%/ HCl to acetonitrile) of the resulting solution yielded 35 mg of the title compound as a white solid: GC/EI-MS, m/z (rel. int.) 314 (M−15, 1), 209 (19), 208 (100), 163 (6), 120 (19), 114 (7), 106 (6), 77 (12), 70 (9), 69 (15), 58 (6).

Example 7

Resolution of the Enantiomers (R) or (S)-N-(2-Hydroxy-3-phenoxypropyl)-1,1-dimethyl-2-(4-methoxyphenyl) ethylamine Hydrochloride, Compounds 32 and 33

Compound 32

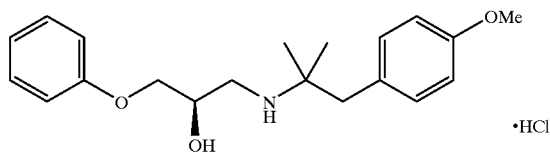

Compound 33

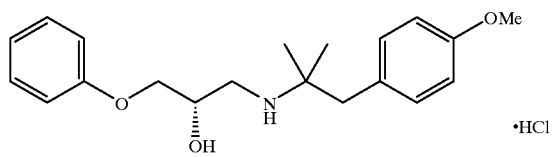

The enantiomers of (R) and (S)-N-(2-hydroxy-3-phenoxypropyl)-1,1-dimethyl-2-(4-methoxyphenyl) ethylamine hydrochloride (compounds 32 and 33) were obtained by chiral HPLC of the free base through ChiralCel OD (20×2.5 cm) using a combination of hexane-isopropanol containing 0.1% diethylamine (10 mL/min) measuring optical density at 260 nm. GC/EI-MS of each enantiomer gave m/z (rel. int.) 330 (M+1, 1), 314 (2), 208 (100), 183 (4), 163 (5), 121 (16), 77 (10), 70 (11). The hydrochloride of each enantiomer was prepared by treatment of the free base in diethyl ether with excess 1M HCl (diethyl ether). Evaporation of the solvent yielded the hydrochloride product as a solid.

Example 8

Preparation of N-[2-Hydroxy-3-(4-chlorophenoxy)propyl]-1,1-dimethyl-2-(4-methoxyphenyl)ethylamine Hydrochloride, Compound 5

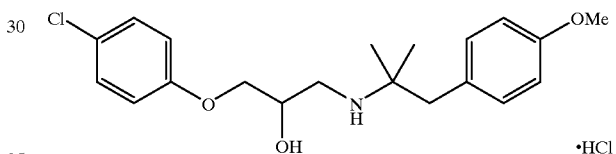

Using the method of Example 6, supra, 4-chlorophenyl glycidyl ether (185 mg, 1 mmol) and 1,1-dimethyl-2-(4-methoxyphenyl)ethylamine (269 mg, 1.5 mmol) were used to prepare 272 mg of the title compound as a white solid: GC/EI-MS, m/z (rel. int.) 348 (M−15, 1), 244 (35), 243 (15), 242 (100), 163 (9), 121 (24), 114 (7), 71 (24), 70 (26), 58 (15), 42 (7).

Example 9

Preparation of N-[2-Hydroxy-3-(4-t-butylphenoxy)propyl]-1,1-dimethyl-2-(4-methoxyphenyl)ethylamine Hydrochloride, Compound 6

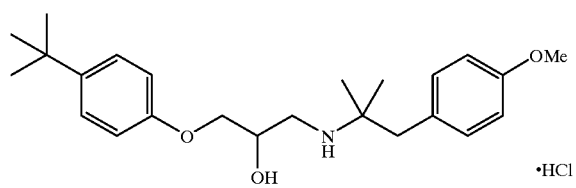

Using the method of Example 5, supra, 4-t-butylphenyl glycidyl ether (206 mg, 1 mmol) and 1,1-dimethyl-2-(4-methoxyphenyl)ethylamine (269 mg, 1.5 mmol) were used to prepare the free base of the title compound. The hydrochloride was prepared by dilution of the reaction mixture with HCl (3 mmol) and water, which caused the product to precipitate. The mixture was heated to effect solution and allowed to cool slowly to crystallize the product. The crystals were collected by filtration, washed with water/ MeOH, and dried under vacuum to give 106 mg of the title compound as a white solid: GC/EI-MS, m/z (rel. int.) 370 (M−15, 0.1), 265 (19), 264 (100), 163 (8), 121 (20), 114 (9), 91 (7), 71 (20), 70 (21), 58 (10), 57 (12).

Example 10

Resolution of the Enantiomers (R) and (S)-N-[2-Hydroxy-3-(4-t-butylphenoxy)propyl]-1,1-dimethyl-2-(4-methoxyphenyl)ethylamine Hydrochloride, Compounds 20 and 21

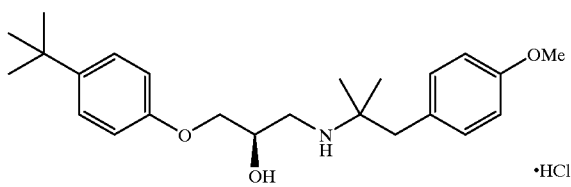

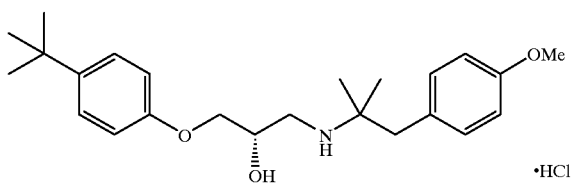

The enantiomers of (R) and (S)-N-[2-hydroxy-3-(4-t-butylphenoxy)propyl]-1,1-dimethyl-2-(4-methoxyphenyl)ethylamine hydrochloride were prepared using the method of Example 7, supra. GC/EI-MS of each enantiomer gave m/z (rel. int.) 386 (M+, 1), 370 (2), 264 (100), 163 (10), 135 (4), 121 (36), 91 (8), 70 (11). The hydrochloride salt of each enantiomer was prepared by treatment of the corresponding free base in diethyl ether with excess 1M HCl (diethyl ether). Evaporation of the solvent yielded the corresponding hydrochloride product as a solid.

Example 11

Preparation of N-[2-Hydroxy-3-(4-methoxyphenoxy)propyl]-1,1-dimethyl-2-(4-methoxyphenyl)ethylamine Hydrochloride, Compound 7

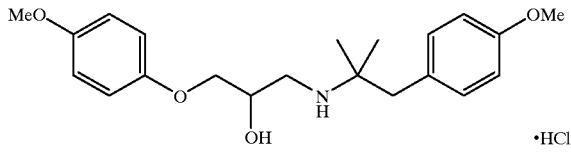

Using the method of Example 8, supra, 4-methoxyphenyl glycidyl ether (180 mg, 1 mmol) and 1,1-dimethyl-2-(4-methoxyphenyl)ethylamine (269 mg, 1.5 mmol) were used to prepare 231 mg of the title compound as a white solid: GC/EI-MS, m/z (rel. int.) 344 (M−15, 0.1), 239 (17), 238 (100), 163 (9), 123 (7), 120 (17), 114 (6), 77 (5), 70 (13), 70 (11), 58 (6).

Example 12

Preparation of N-[2-Hydroxy-3-(2-methylphenoxy)propyl]-1,1-dimethyl-2-(4-methoxyphenyl)ethylamine Hydrochloride, Compound 8

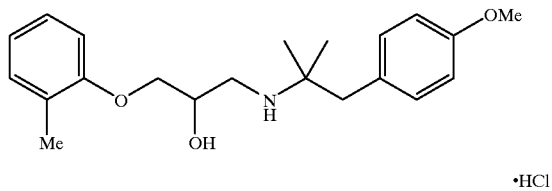

Using the method of Example 9, supra, 2-methylphenyl glycidyl ether (164 mg, 1 mmol) and 1,1-dimethyl-2-(4-methoxyphenyl)ethylamine (269 mg, 1.5 mmol) were used to prepare 257 mg of the title compound as a white solid: GC/EI-MS, m/z (rel. int.) 328 (M−15, 0.1), 223 (17), 222 (100), 163 (8), 121 (23), 114 (11), 91 (13), 77 (6), 71 (19), 70 (21), 58 (11).

Example 13

Preparation of N-[2-Hydroxy-3-(4-(2-carboxamido)indoloxy)propyl]-1,1-dimethyl-2-(4-methoxyphenyl)ethylamine Hydrochloride, Compound 9

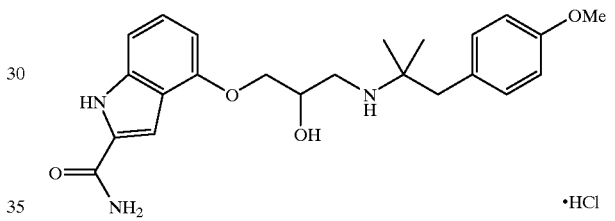

Using the method of Example 6, supra, 4-glycidyloxy-2-indolecarboxamide (232 mg, 1 mmol) and 1,1-dimethyl-2-(4-methoxyphenyl)ethylamine (269 mg, 1.5 mmol) were used to prepare 222 mg of the title compound as a white solid: GC/EI-MS, m/z (rel. int.) 396 (M−15, 0.1), 291 (17), 290 (100), 207 (10), 158 (7), 130 (7), 121 (28), 114 (19), 71 (18), 70 (15).

Example 14

Preparation of N-(3-Phenoxypropyl)-1,1-dimethyl-2-(4-methoxyphenyl)ethylamine Hydrochloride, Compound 17

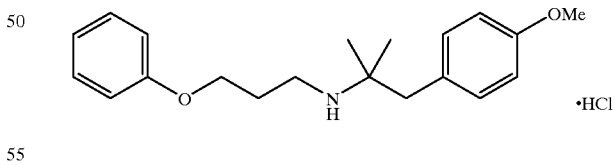

To a stirred suspension of 50% KF-Celite (0.35 g, 3 mmol) in anhydrous acetonitrile (10 mL) was added 1,1-dimethyl-2-(4-methoxyphenyl)ethylamine (0.27 g, 1.5 mmol) and 3-phenoxypropyl bromide (0.484 g, 2.25 mmol). The reaction mixture was refluxed under nitrogen for 6 hours, followed by stirring at room temperature for 62 hours. The mixture was filtered and the filtrate, was evaporated. The hydrochloride was prepared by dissolving the residue in HCl/methanol. The resulting solution was concentrated and dried on a lyophilizer. The residue was redissolved in dry methanol and diluted with diethyl ether, which caused precipitation of 210 mg of the title compound as a white solid: GC/EI-MS, m/z (rel. int.) 298 (M−15, 2), 193 (15), 192 (100), 120 (13), 107 (5), 98 (9), 77 (8), 72 (7), 71 (8), 70 (6), 41 (4).

Example 15

Preparation of N-[2-Hydroxy-3-(1-naphthoxy)propyl]-1,1-dimethyl-2-(4-methoxyphenyl)ethylamine Hydrochloride, Compound 19

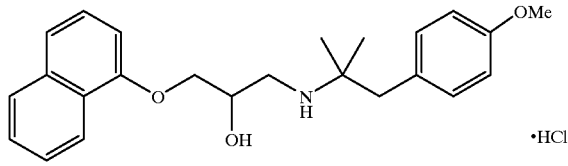

Using the method of Example 5, supra, 1-naphthyl glycidyl ether (1.0 g, 5 mmol) and 1,1-dimethyl-2-(4-methoxyphenyl)ethylamine (1.0 mg, 5.6 mmol) were used to prepare the free base of the title compound. Silica gel chromatography of the reaction mixture using 5% methanol in chloroform afforded 1.66 g (88%) of the purified product: GC/EI-MS, m/z (rel. int.) 364 (M−15, 1), 258 (100), 183 (3), 163 (4), 144 (4), 121 (23), 115 (18), 71 (19); $^1$H-NMR (C$_6$D$_6$) δ8.50 (1H, d, J=8.0), 7.65 (1H, d, J=7.2), 7.36–7.31 (3H, m), 7.21 (1H, t, J=7.9), 6.98 (2H, d, J=8.6), 6.71 (2H, d, J=8.6), 6.62 (1H, d, J=7.7), 4.08 (2H, m), 3.93 (1H, m), 3.32 (3H, s), 2.80 (1H, dd, J=11.6 and 3.7), 2.71 (1H, dd, J=11.4 and 6.4), 2.47 (2H, dd, J=13.3 and 6.2), 0.94 (3H, s), 0.92 (3H, s); $^{13}$C-NMR (CDCl$_3$) δ158.0, 154.3, 134.4, 131.2 (2 carbons), 129.9, 127.4, 126.3, 125.8, 125.2, 121.8, 120.5, 113.3 (2 carbons), 104.8, 70.4, 68.5, 55.0, 53.2, 46.4, 44.5, 26.9, 26.8. A portion of the free base in diethyl ether was treated with excess 1M HCl (diethyl ether). The resulting solid was recrystallized from hot acetonitrile to afford the title compound as a white solid.

Example 16

Preparation of N-(2-Hydroxy-3-t-butoxypropyl)-1,1-dimethyl-2-(4-methoxyphenyl)ethylamine, Compound 25

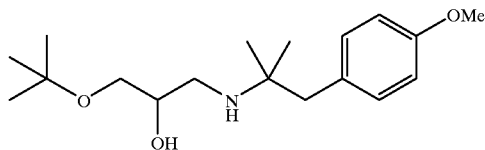

Using the method of Example 15, supra, t-butylglycidyl ether (142 mg, 1.0 mmol) and 1,1-dimethyl-2-(4-methoxyphenyl)ethylamine (197 mg, 1.1 mmol) were used to prepare 106 mg of the title compound as a clear, colorless oil: GC/EI-MS, m/z (rel. int.) 310 (M+1. 0.3), 294 (0.5), 222 (1.8), 188 (67.9), 163 (14.6), 132 (100), 121 (19.1); $^1$H-NMR (CDCl$_3$) δ7.09 (2H, d, J=8.6), 6.82 (2H, d, J=8.6), 3.78 (3H, s), 3.68 (1H, m), 3.37 (2H, m), 2.27 (1H, dd, J=11.5 and 4.2), 2.63 (3H, m), 1.19 (9H, s), 1.05 (3H, s), 1.03 (3H, s); $^{13}$C-NMR (CDCl$_3$) δ156.0, 131.3, 130.3, 113.3, 72.9, 69.7, 64.5, 55.1, 52.9, 46.6, 44.7, 27.9, 26.9, 26.8.

Example 17

Preparation of N-(2-Hydroxy-3-butoxypropyl)-1,1-dimethyl-2-(4-methoxyphenyl)ethylamine, Compound 26

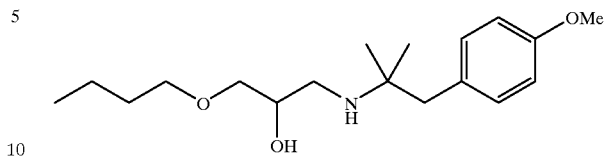

Using the method of Example 15, supra, n-butyl glycidyl ether (143 μL, 1.0 mmol) and 1,1-dimethyl-2-(4-methoxyphenyl)ethylamine (197 mg, 1.1 mmol) were used to prepare 81 mg of the title compound as a clear, colorless oil: GC/EI-MS, m/z (rel. int.) 310 (M+1, 0.01), 174 (100), 163 (19), 132(18), 121(31), 70(20); $^1$H-NMR (CDCl$_3$) δ7.03 (2H, d, J=8.6), 6.87 (2H, d, J=8.6), 3.74 (1H, m), 3.72 (3H, s), 3.40 (4H, m), 2.73 (3H, m), 2.59 (3H, m), 1.50 (2H, m), 1.30 (2H, m), 1.01 (3H, s), 0.99 (3H, s), 0.87 (3H, t, J=7.4); $^{13}$C-NMR (CDCl$_3$) δ157.9, 131.2, 129.9, 113.2, 73.5, 71.2, 69.0, 54.9, 53.1, 46.2, 44.5, 31.5, 26.6, 26.4, 19.1, 13.8.

Example 18

Preparation of N-(2-Hydroxy-3-isopropoxypropyl)-1,1-dimethyl-2-(4-methoxyphenyl)ethylamine, Compound 27

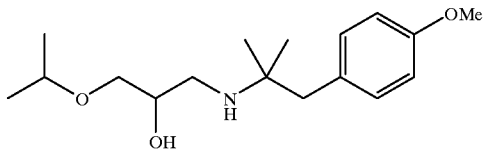

Using the method of Example 15, supra, isopropylglycidyl ether (126 μL, 1.0 mmol) and 1,1-dimethyl-2-(4-methoxyphenyl)ethylamine (197 mg, 1.1 mmol) were used to prepare 53 mg of the title compound as a clear, colorless oil; GC/EI-MS, m/z (rel. int.) 296 (M+1, 0.2), 280 (1.4), 222 (1.5), 174 (100), 132 (12), 121(24); $^1$H-NMR (CDCl$_3$) δ7.03 (2H, d, J=8.4), 6.77 (2H, d, J=8.4), 3.72 (3H, s), 3.70 (1H, m), 3.53 (1H, m), 3.38 (2H, m), 2.80 (1H, broad s), 2.73 (2H, m), 2.58 (4H, m) 1.09 (6H, m), 1.01 (3H, s), 0.99 (3H, s); $^{13}$C-NMR (CDCl$_3$) δ157.9, 131.2, 129.9, 113.2, 73.4, 71.2, 69.0, 54.9, 53.1, 46.2, 44.5, 31.5, 26.6, 26.4, 19.1, 13.8.

Example 19

Preparation of N-[2-Hydroxy-3-(2-ethyl)hexanoxypropyl]-1,1-dimethyl-2-(4-methoxyphenyl)ethylamine, Compound 28

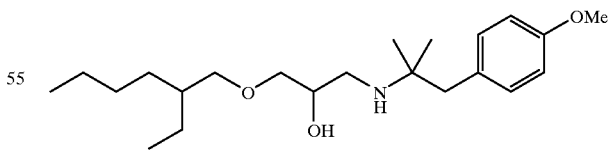

Using the method of Example 15, supra, 2-ethylhexyl glycidyl ether (209 μL, 1.0 mmol) and 1,1-dimethyl-2-(4-methoxyphenyl)ethylamine (197 mg, 1.1 mmol) were used to prepare 55 mg of the title compound as a clear, colorless oil: GC/EI-MS, m/z (rel. int.) 366 (M+1. 0.2), 350 (1.1), 244 (100), 222 (2.5), 163 (8.7), 121 (15); $^1$H-NMR (CDCl$_3$) δ7.06 (2H, d, J=8.5), 6.80 (2H, d, J=8.6), 3.75 (3H, s), 3.4 (2H, d, J=5.3), 3.31 (2H, d, J=6.0), 2.88 (1H, broad), 2.78

(1H dd, J=11.6 and 4.0), 2.62 (2H, m), 1.46 (1H, q, J=5.7), 1.24 (6H, m), 1.03 (4H, m), 0.84 (4H, m); $^{13}$C-NMR (CDCl$_3$) δ158.0, 131.3, 130.0, 113.3, 74.4, 73.7, 69.0, 55.1, 53.3, 46.3, 44.6, 39.5, 30.5, 29.0, 26.6, 26.4, 23.8, 23.0, 14.0, 11.0; Anal. calculated for C$_{22}$H$_{39}$NO$_3$: C, 72.3, H, 10.8, N, 3.8. Found: C, 72.2, H, 9.9, N, 3.6.

Example 20

Resolution of the Enantiomers (R) and (S)-N-[2-Hydroxy-3-(2-ethyl)hexanoxypropyl]-1,1-dimethyl-2-(4-methoxyphenyl)ethylamine Hydrochloride, Compounds 63 and 64

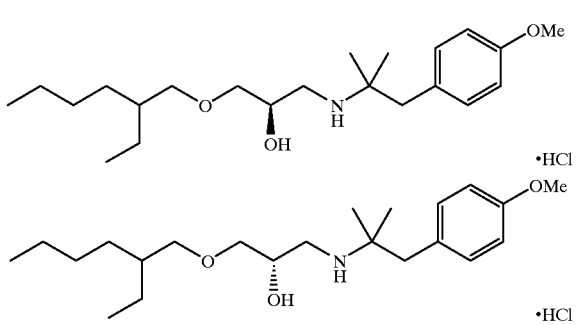

The enantiomers (R) and (S)-N-[2-hydroxy-3-(2-ethyl)hexanoxypropyl]-1,1-dimethyl-2-(4-methoxyphenyl)ethylamine hydrochloride were prepared using the method of Example 7, supra. GC/EI-MS of each enantiomer gave m/z (rel. int.) 366 (M+1, 1), 350 (2), 244 (100), 222 (3), 163 (12), 133 (9), 121 (21), 115 (11), 100 (4), 71 (21). The hydrochloride salt of each enantiomer was prepared by treatment of the free amine in diethyl ether with excess 1M HCl (diethyl ether). Evaporation of the solvent yielded the hydrochloride product as a solid.

Example 21

Preparation of N-(2-Hydroxy-3-allyloxypropyl)-1,1-dimethyl-2-(4-methoxyphenyl)ethylamine, Compound 29

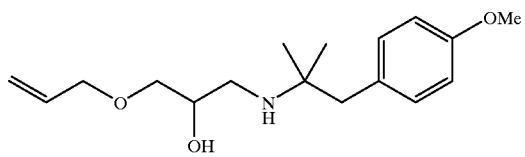

Using the method of Example 15, supra, allyl glycidyl ether (119 μL, 1.0 mmol) and 1,1-dimethyl-2-(4-methoxyphenyl)ethylamine (197 mg, 1.1 mmol) were used to prepare 79 mg of the title compound as a clear, colorless oil: GC/EI-MS, m/z (rel. int.) 294 (M+1, 0.1), 278 (0.9), 222 (1.5), 172 (100), 163 (11), 121 (20); $^1$H-NMR (CDCl$_3$) δ7.04 2H, di J=8.6), 6.79 (2H, d, J=8.6), 5.85 (1H, ddd, J=22.2, 10.5 and 5.7), 5.23 (1H, dd, J=17.3 and 1.5), 5.14 (1H, dd, J=10.3 and 1.5), 3.96 (2H, d, J=5.7), 3.74 (4H, m), 3.43 (2H, d, J=5.7), 2.83 (1H, broad s), 2.77 (1H, dd, J=11.7 and 4.1), 2.62 (5H, m), 1.02 (3H, s), 1.01 (3H, s); $^{13}$C-NMR (CDCl$_3$) δ158.0, 134.5, 131.3, 129.9, 117.0, 113.3, 72.8, 72.2, 69.0, 55.0, 53.3, 46.3, 44.5, 26.6, 26.4.

Example 22

Preparation of N-[2-Hydroxy-3-(2-naphthoxy)propyl]-1,1-dimethyl-2-(4-methoxyphenyl)ethylamine Hydrochloride, Compound 35

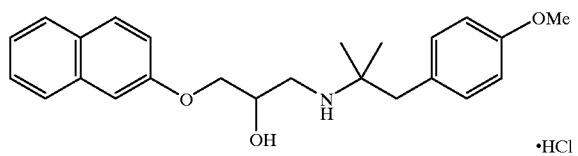

Using the method of Example 4, supra, 2-naphthyl glycidyl ether (400 mg, 2 mmol) and 1,1-dimethyl-2-(4-methoxyphenyl)ethylamine (358 mg, 2 mmol) were used to prepare the free base of the title compound : GC/EI-MS, m/z (rel. int.) 364 (M−15, 1), 258 (100), 183 (2), 163 (3), 144 (4), 127 (10), 121 (22), 115 (20), 71 (11). The free base in diethyl ether was treated with excess 1M HCl (Diethyl ether). The resulting solid was recrystallized from hot acetonitrile to afford 456 mg of the hydrochloride product as a white solid.

Example 23

Preparation of N-(2-Hydroxy-3-phenylpropyl)-1,1-dimethyl-2-(4-methoxyphenyl)ethylamine Hydrochloride, Compound 37

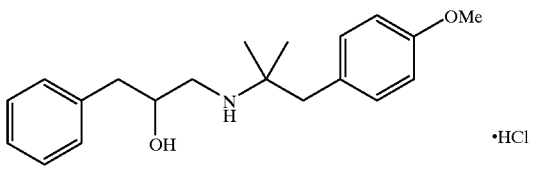

Using the method of Example 6, supra, 2,3-epoxypropylbenzene (1 mmol) and 1,1-dimethyl-2-(4-methoxyphenyl)ethylamine (1.25 mmol) yielded 179 mg of the title compound as a white solid: GC/EI-MS, m/z (rel. int.) 289 (M−15, 1), 193 (16), 192 (100), 163 (7), 121 (18), 117 (12), 91 (32), 77 (5), 70 (16), 58 (9).

Example 24

Preparation of N-[2-Hydroxy-3-(3-methoxyphenoxy)propyl]-1,1-dimethyl-2-(4-methoxyphenyl)ethylamine Hydrochloride, Compound 38

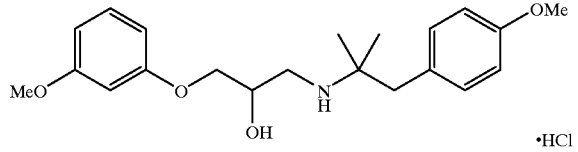

Using the method of Example 6, supra, 3-methoxyphenyl glycidyl ether (1.5 mmol) and 1,1-dimethyl-2-(4-methoxyphenyl)ehtylamine (1.9 mmol) yielded 403 mg of the title compound as a white solid: GC/EI-MS, m/z (rel. int.) 344 (M−15, 1), 239 (21), 238 (100), 163 (10), 121 (16), 114 (9), 106 (3), 77 (5), 71), 70 (10), 58 (4).

Example 25
Preparation of N-[2-Hydroxy-3-(3-fluorophenoxy)propyl]-1,1-dimethyl-2-(4-methoxyphenyl)-ethylamine Hydrochloride, Compound 39

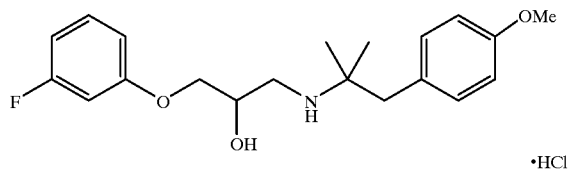

A solution of 3-fluorophenol (1.8 g, 16.1 mmol) in acetone (100 mL) was treated with potassium carbonate (6.65 g, 48.2 mmol) and refluxed under nitrogen for 15 minutes. Epibromohydrin (4.4 g, 32.1 mmol) was then added by syringe, and the mixture was refluxed 3 hours. The mixture was cooled and filtered, and the filtrate evaporated to dryness. The residue was partitioned between ether/water, and the layers separated. The ether layer was washed with saturated NaCl, dried over sodium sulfate and evaporated. The resulting oil was distilled under vacuum to give 1.2 g of 3-fluorophenyl glycidyl ether.

Using the method of Example 6, supra, 3-fluorophenyl glycidyl ether (1.5 mmol) and 1,1-dimethyl-2-(4-methoxyphenyl)ethylamine (1.9 mmol) yielded 398 mg of the title compound as a white solid: GC/EI-MS, m/z (rel. int.) 332 (M−15, 1), 227 (22), 226 (100), 163 (7), 151 (6), 120 (22), 114 (6), 94 (7), 71 (11), 70 (16), 57 (8).

Example 26
Preparation of N-[2-Hydroxy-3-(2-chlorophenoxy)propyl]-1,1-dimethyl-2-(4-methoxyphenyl)-ethylamine Hydrochloride, Compound 40

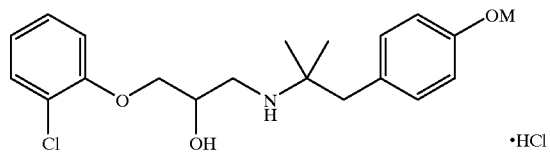

Using the method of Example 25, supra, 2-chlorophenyl glycidyl ether (1.0 mmol) and 1,1-dimethyl-2-(4-methoxyphenyl)ethylamine (1.25 mmol) yielded 279 mg of the title compound as a white solid: GC/EI-MS, m/z (rel. int.) 348 (M−15, 5), 245 (21), 244 (100), 242 (100), 163 (29), 121 (82), 114 (24), 77 (21), 71 (44), 70 (56), 58 (24).

Example 27
Preparation of N-[2-Hydroxy-3-(2-fluorophenoxy)propyl]-1,1-dimethyl-2-(4-methoxyphenyl)-ethylamine Hydrochloride, Compound 41

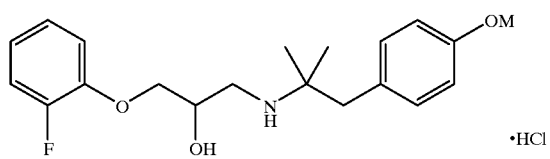

Using the method of Example 25, supra, 2-fluorophenyl glycidyl ether (1.5 mmol) and 1,1-dimethyl-2-(4-methoxyphenyl)ethylamine (1.9 mmol) yielded 385 mg of the title compound as a white solid: GC/EI-MS, m/z (rel. int.) 332 (M−15, 2), 227 (20), 226 (100), 163 (4), 125 (3), 121 (15), 78 (4), 77 (4), 71 (7), 70 (9), 58 (3).

Example 28
Preparation of N-[2-Hydroxy-3-(3-chlorophenoxy)propyl]-1,1-dimethyl-2-(4-methoxyphenyl)ethylamine Hydrochloride, Compound 43

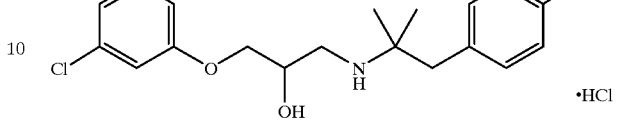

Using the method of Example 25, supra, 3-chlorophenyl glycidyl ether (1.0 mmol) and 1,1-dimethyl-2-(4-methoxyphenyl)ethylamine (1.25 mmol) yielded 168 mg of the title compound as a white solid: GC/EI-MS, m/z (rel. int.) 348 (M−15, 0.9), 245 (7), 244 (35), 243 (25), 242 (100), 163 (7), 121 (22), 71 (11), 70 (16).

Example 29
Preparation of N-[2-Hydroxy-3-(4-fluorophenoxy)propyl]-1,1-dimethyl-2-(4-methoxyphenyl)ethylamine Hydrochloride, Compound 44

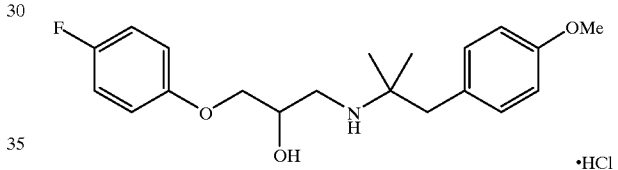

Using the method of Example 25, supra, 4-fluorophenyl glycidyl ether (1.5 mmol) and 1,1-dimethyl-2-(4-methoxyphenyl)ethylamine (1.9 mmol) yielded 398 mg of the title compound as a white solid: GC/EI-MS, m/z (rel. int.) 332 (M−15, 1), 227 (20), 226 (100), 163 (5), 125 (4), 121 (15), 114 (3), 95 (4), 71 (8), 70 (10), 58 (5).

Example 30
Preparation of N-[2-Hydroxy-3-(3-methylphenoxy)propyl]-1,1-dimethyl-2-(4-methoxyphenyl)ethylamine Hydrochloride, Compound 45

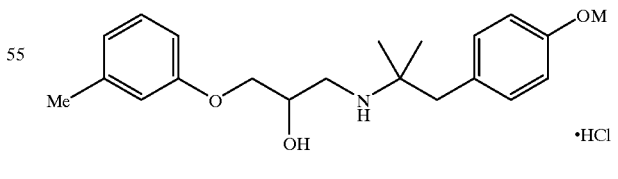

Using the method of Example 25, supra, 3-methylphenyl glycidyl ether (2.0 mmol) and 1,1-dimethyl-2-(4-methoxyphenyl)ethylamine (2.5 mmol) yielded 400 mg of the title compound as a white solid: GC/EI-MS, m/z (rel. int.) 328 (M−15,1), 223 (16), 222 (100), 163 (5), 147 (5), 121 (18), 114 (6), 91 (8), 76 (4), 71 (6), 70 (11).

Example 31

Preparation of N-[2-Hydroxy-3-(3-trifluoromethylphenoxy) propyl]-1,1-dimethyl-2-(4-methoxyphenyl)ethylamine Hydrochloride, Compound 46

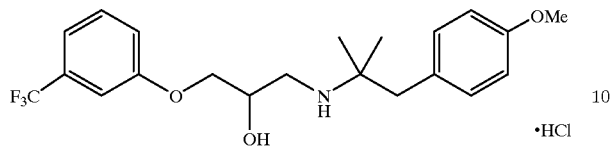

Using the method of Example 25, supra, 3-trifluoromethylphenyl glycidyl ether (2.0 mmol) and 1,1-dimethyl-2-(4-methoxyphenyl)ethylamine (2.5 mmol) yielded 600 mg of the title compound as a white solid: GC/EI-MS, m/z (rel. int.) 382 (M–15, 1), 277 (16), 276 (100), 163 (7), 126 (4), 121 (18), 114 (5), 96 (6), 71 (8), 70 (15), 57 (4).

Example 32

Preparation of N-[2-Hydroxy-3-(2-trifluoromethylphenoxy) propyl]-1,1-dimethyl-2-(4-methoxyphenyl)ethylamine Hydrochloride, Compound 47

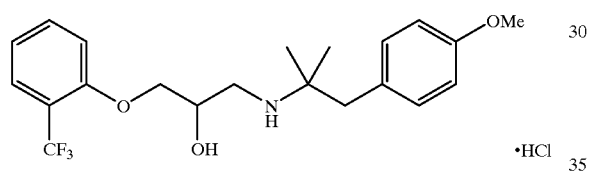

Using the method of Example 25, supra, 2-trifluoromethylphenyl glycidyl ether (2.0 mmol) and 1,1-dimethyl-2-(4-methoxyphenyl)ethylamine (2.5 mmol) yielded 690 mg of the title compound as a white solid: GC/EI-MS, m/z (rel. int.) 382 (M–15, 1), 277 (16), 276 (100), 163 (10), 121 (22), 114 (8), 96 (11), 71 (17), 70 (33), 58 (9), 42 (6).

Example 33

Preparation of N-[2-Hydroxy-3-(2-t-butylphenoxy)propyl]-1,1-dimethyl-2-(4-methoxyphenyl)ethylamine Hydrochloride, Compound 48

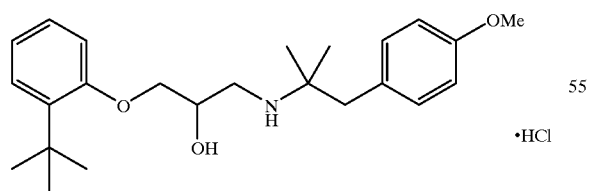

Using the method of Example 25, supra, 2-t-butylphenyl glycidyl ether (2.0 mmol) and 1,1-dimethyl-2-(4-methoxyphenyl)ethylamine (2.5 mmol) yielded 540 mg of the title compound as a white solid: GC/EI-MS, m/z (rel. int.) 370 (M–15, 1), 265 (19), 264 (100), 163 (5), 121 (17), 114 (6), 91 (8), 77 (3), 71 (9), 70 (8), 58 (3).

Example 34

Preparation N-[2-Hydroxy-3-(2-methoxyphenoxy)propyl]-1,1-dimethyl-2-(4-methoxyphenyl)ethylamine Hydrochloride, Compound 49

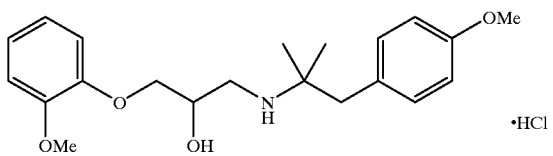

Using the method of Example 25, supra, 2-methoxyphenyl glycidyl ether (2.0 mmol) and 1,1-dimethyl-2-(4-methoxyphenyl)ethylamine (2.5 mmol) yielded 60 mg of the title compound as a white solid: GC/EI-MS, m/z (rel. int.) 344 (M–15, 0.1), 239 (15), 238 (100), 163 (9), 122 (7), 121 (20), 114 (13), 77 (10), 71 (19), 70 (21), 58 (7).

Example 35

Preparation of N-[2-Hydroxy-3-(3-t-butylphenoxy)propyl]-1,1-dimethyl-2-(4-methoxyphenyl)ethylamine Hydrochloride, Compound 50

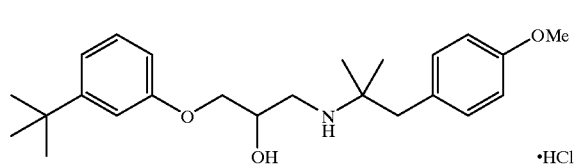

Using the method of Example 25, supra, 3-t-butylphenyl glycidyl ether (2.0 mmol) and 1,1-dimethyl-2-(4-methoxyphenyl)ethylamine (2.5 mmol) yielded 400 mg of the title compound as a white solid: GC/EI-MS, m/z (rel. int.) 370 (M–15, 1), 265 (19), 264 (100), 163 (5), 121 (15), 114 (5), 110 (3), 91 (4), 71 (6), 70 (9), 57 (3).

Example 36

Preparation of N-[2-Hydroxy-3-(4-trifluoromethylphenoxy) propyl]-1,1-dimethyl-2-(4-methoxyphenyl)ethylamine Hydrochloride, Compound 51

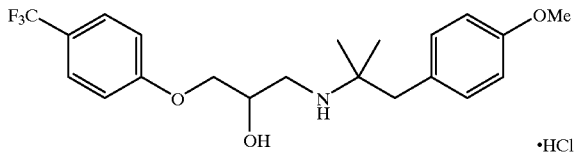

Using the method of Example 25, supra, 4-trifluoromethylphenyl glycidyl ether (1.43 mmol) and 1,1-dimethyl-2-(4-methoxyphenyl)ethylamine (1.8 mmol) yielded 270 mg of the title compound as a white solid: GC/EI-MS, m/z (rel. int.) 382 (M–15, 3), 277 (35), 276 (100), 175 (8), 163 (8), 145 (16), 121 (34), 78 (9), 71 (15), 70 (19), 58 (8).

Example 37
Preparation of N-(2-Hydroxy-3-phenoxypropyl)-1,1-dimethyl-2-phenylethylamine Hydrochloride, Compound 56

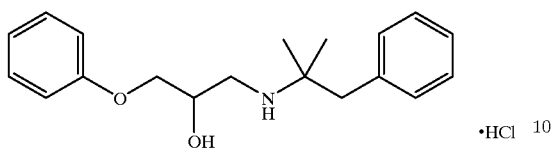

Using the method of Example 5, supra, 1,2-epoxy-3-phenoxypropane (600 mg, 4 mmol) and 1,1-dimethyl-2-phenylethylamine (596 mg, 4 mmol) yielded the title compound: GC/EI-MS, m/z (rel. int.) 284 (M+1, 1), 208 (100), 162 (1), 133 (7), 91 (27), 77 (15), 70 (22). The free base in diethyl ether was treated with excess 1M HCl (diethyl ether). The resulting solid was recrystallized from hot acetonitrile to afford 596 mg of the hydrochloride product as a white solid.

Example 38
Preparation of N-(2-Methoxy-3-phenoxypropyl)-1,1-dimethyl-2-(4-methoxyphenyl)ethylamine Hydrochloride, Compound 59

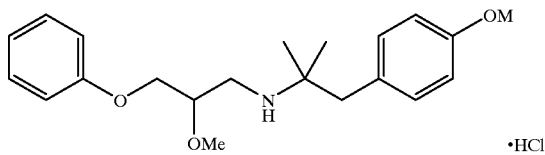

Allyl phenyl ether (1.34 g, 10 mmol) and N-bromosuccinimide (1.78 g, 10 mmol) were dissolved in 50 mL of methanol and stirred at room temperature for two days. The product, a 1:1 mixture of 2-bromo-1-methoxy-3-phenoxypropane and 1-bromo-2-methoxy-3-phenoxypropane, was isolated by evaporating the methanol and dissolving the residue in heptane/ether/water. The organic layer was washed first with water, then brine, dried over sodium sulfate, and evaporated to dryness. The crude mixture (1.47 g, 6 mmol) was dissolved in 6 mL of acetonitrile, to which was added 50% KF-Celite (0.7 g, 12 mmol) and 1,1-dimethyl-2-(4-methoxyphenyl)ethylamine (0.54 g, 3 mmole). The mixture was refluxed under nitrogen for 48 hours, and then cooled and filtered. The filtrate was evaporated to dryness, and the residue was taken up in water and ether. The ether layer was dried over sodium sulfate and concentrated to dryness. The residue was dissolved in 10 mL of diethyl ether and precipitated as the HCl salt by the addition of 10 mL of 1M HCl (diethyl ether). The collected solid was purified by RP-HPLC to yield 330 mg of the title compound as a white solid: GC/EI-MS, m/z (rel. int.) 328 (M-15, 5), 223 (43), 222 (100), 163 (9), 133 (13), 121 (42), 107 (13), 78 (11), 77 (23), 71 (12), 70 (32).

Example 39
Preparation of N-(2-Hydroxy-3-octanoxypropyl)-1,1-dimethyl-2-(4-methoxyphenyl)ethylamine, Compound 65

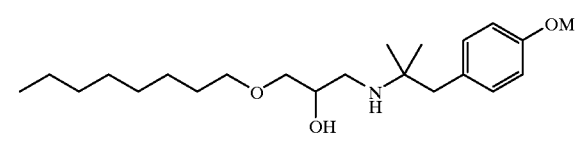

Using the method of Example 5, supra, 1-octyl glycidyl ether (187 mg, 1.0 mmol) and 1,1-dimethyl-2-(4-methoxyphenyl)ethylamine (197 mg, 1.1 mmol) were used to prepare 105 mg of the title compound as a clear, colorless oil: GC/EI-MS, m/z (rel. int.) 366 (M+1, 0.08), 350 (0.08), 244 (100), 222 (5.8), 163 (12), 121 (18): $^1$H-NMR (CDCl$_3$) δ7.08 (2H, d, J=8.6), 6.82 (2H, d, J=8.6), 3.79 (1H, m), 3.77 (3H, s), 3.45 (4H, m), 2.92 (1H, broad s), 2.79 (1H, dd, J=11.6 and 4.1), 2.65 (2H, m), 2.55 (2H, m), 1.27 (8H, m), 1.06 (3H, s), 1.04 (3H, s), 0.88 (3H, t, J=6.7); $^{13}$C-NMR (CDCl$_3$) δ158.0, 131.2, 129.9, 113.2, 73.4, 71.6, 68.9, 55.0, 53.3, 46.2, 44.6, 31.7, 29.5, 29.3, 29.1, 26.5, 26.4, 26.0, 22.5, 14.0; FT-IR (film) cm$^{-1}$ 3409 (broad), 1611, 1512, 1245, 1120.

Example 40
Preparation of N-(2-Hydroxy-3-hexanoxypropyl)-1,1-dimethyl-2-(4-methoxyphenyl)ethylamine, Compound 66

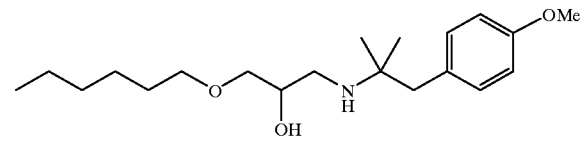

Using the method of Example 5, supra, 1-hexyl glycidyl ether (175 mg, 1.0 mmol) and 1,1-dimethyl-2-(4-methoxyphenyl)ethylamine (197 mg, 1.1 mmol) were used to prepare 95 mg of the title compound as a clear, colorless oil: GC/EI-MS, m/z (rel. int.) 216 (M−121), 163 (11), 121 (22), 114 (14); $^1$H-NMR (CDCl$_3$) δ7.05 (2H, d, J=8.7), 6.79 (2H, d, J=8.7), 3.77 (1H, m), 3.75 (3H, s), 3.41 (4H, m), 2.97 (2H, broad), 2.79 (1H, dd, J=11.7 and 4.1), 2.64 (3H, m), 1.52 (2H, m), 1.26 (6H, m), 1.04 (3H, s), 1.03 (3H, s), 0.85 (3H, t, J=6.7); $^{13}$C-NMR (CDCl$_3$) δ158.1, 131.3, 129.9, 113.4, 73.4, 71.7, 68.9, 55.1, 53.6, 46.3, 44.6, 31.6, 29.5, 26.5, 26.4, 25.7, 22.6, 14.0; FT-IR, cm$^{-1}$ 3405 (broad), 1611, 1512, 1245, 1116, 824.

Example 41
Preparation of N-(2-Hydroxy-3-decanoxypropyl)-1,1-dimethyl-2-(4-methoxyphenyl)ethylamine, Compound 67

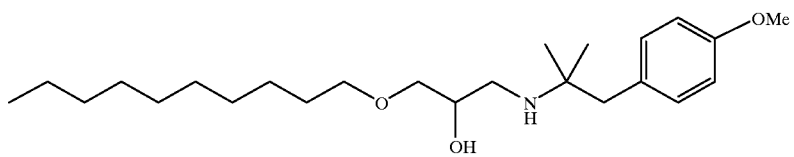

Using the method of Example 5, supra, 1-decyl glycidyl ether (235 mg, 1.0 mmol) and 1,1-dimethyl-2-(4-methoxyphenyl)ethylamine (197 mg, 1.1 mmol) were used to prepare 175 mg of the title compound as a clear, colorless oil: GC/EI-MS, m/z (rel. int.) 394 (M+1, 1), 378 (6), 273 (97), 272 (100), 222 (9), 163 (37), 121 (61); $^1$H-NMR (CDCl$_3$) δ7.49 (2H, d, J=8.5), 6.82 (2H, d, J=8.5 Hz), 3.78 (3H, s), 3.75 (1H, m), 3.45 (4H, m), 2.80 (1H, dd, J=11.7 and 4.0), 2.77 (1H, broad s), 2.64 (4H, m), 1.56 (2H, m), 1.26 (16H, m), 1.06 (3H, s), 1.05 (3H, s), 0.88 (3H, t, J=6.1); $^{13}$C-NMR (CDCl$_3$) δ158.1, 131.3, 130.0, 113.4, 73.5, 71.7, 69.1, 55.1, 53.3, 46.4, 44.6, 31.8, 29.6, 29.5, 29.4, 29.3, 26.7, 26.6, 26.1, 22.6, 14.1; FT-IR (film) cm$^{-1}$ 3115 (broad s), 1612, 1512, 1245, 1121, 824.

Example 42
Preparation of N-(2-Hydroxy-3-thiophenylpropyl)-1,1-dimethyl-2-(4-methoxyphenyl)ethylamine, Compound 68

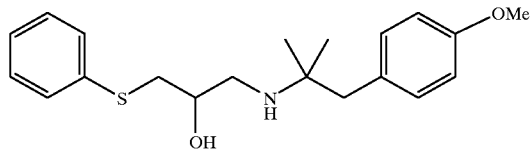

Using the method of Example 25, supra, phenyl glycidyl sulfide (3.9 mmol) and 1,1-dimethyl-2-(4-methoxyphenyl)-ethylamine (4.9 mmol) yielded 194 mg of the title compound as a white solid: GC/EI-MS, m/z (rel. int.) 330 (M−15, 4), 226 (21), 225 (58), 224 (100), 163 (25), 149 (25), 123 (100), 121 (75), 77 (18), 71 (22), 70 (26).

Example 43
Preparation of N-(2-Hydroxydecanyl)-1,1-dimethyl-2-(4-methoxyphenyl)ethylamine, Compound 69

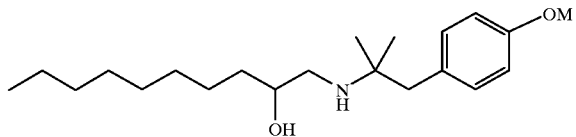

Using the method of Example 5, supra, 1,2-epoxydecane (204 mg, 1.0 mmol) and 1,1-dimethyl-2-(4-methoxyphenyl)ethylamine (197 mg, 1.1 mmol) were used to prepare 73 mg of the title compound as a clear, colorless oil: GC/EI-MS, m/z (rel. int.) 214 (M−121, 100), 196 (27.8), 163 (10), 121 (2.2); $^1$H-NMR (CDCl$_3$) δ7.08 (2H, d, J=8.6), 6.83 (2H, d, J=8.6), 3.79 (3H, s), 3.53 (1H, m), 2.79 (1H, dd, J=11.7 and 2.9), 2.67 (2H, s), 2.42 (1H, dd, J=12.6 and 9.6), 1.26 (18H, m), 1.08 (3H, s), 0.88 (3H, t, J=6.6); $^{13}$C-NMR (CDCl$_3$) δ158.2, 131.4, 129.8, 113.5, 77.2, 69.8, 55.2, 53.8, 47.8, 46.5, 35.1, 31.9, 29.8, 29.7, 29.6, 29.3, 26.6, 26.4, 25.7, 22.7, 14.1; FT-IR (film) cm$^{-1}$ 3399 (broad s), 1612, 1512, 1246, 1039, 823.

Example 44
Preparation of N-(2-Hydroxydodecanyl)-1,1-dimethyl-2-(4-methoxyphenyl)ethylamine, Compound 70

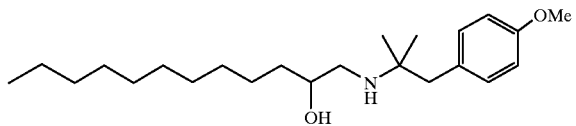

Using the method of Example 5, supra, 1,2-epoxydodecane (240 μL, 1.0 mmol) and 1,1-dimethyl-2-(4-methoxyphenyl)ethylamine (197 mg, 1.1 mmol) were used to prepare 68 mg of the title compound as a clear, colorless oil: GC/EI-MS, m/z (rel. int.) 363 (M+1, 0.2), 348 (2), 242 (100), 224 (8), 163 (7), 121 (20); $^1$H-NMR (CDCl$_3$) δ7.08 (2H, d, J=8.4), 6.83 (2H, d, J=8.4), 3.79 (3H, s), 3.50 (1H, m), 2.78 (1H, dd, J=11.8 and 3.1), 2.66 (2H, s), 2.41 (1H, dd, J=11.5 and 9.3), 1.26 (18H, m), 1.07 (6H, s), 0.88 (3H, t, J=6.5); $^{13}$C-NMR (CDCl$_3$) δ158.2, 131.4, 129.9, 113.4, 76.9, 70.0, 55.2, 53.6, 47.8, 46.6, 35.1, 31.9, 29.7, 29.6, 29.3, 26.7, 26.5, 25.7, 22.7, 14.1; FT-IR (film) cm$^{-1}$ 3386, 1612, 1512, 1246, 1039, 824.

Example 45
Preparation of N-(2-Hydroxydec-9-enyl)-1,1-dimethyl-2-(4-methoxyphenyl)ethylamine, Compound 71

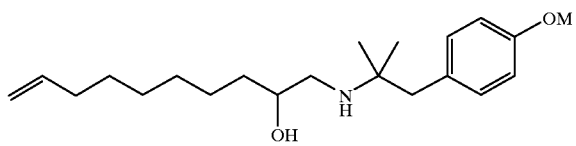

Using the method of Example 5, supra, 1,2-epoxy-9-decene (202 mg, 1.0 mmol) and 1,1-dimethyl-2-(4-methoxyphenyl)ethylamine (197 mg, 1.1 mmol) were used to prepare 80 mg of the title compound as a clear, colorless oil: GC/EI-MS, m/z (rel. int.) 334 (M+1, 0.02), 318 (0.7), 212 (100), 194 (13), 163 (11), 121 (23); $^1$H-NMR (CDCl$_3$) δ7.06 (2H, d, J=8.6), 6.80 (2H, d, J=8.6), 5.79 (1H, dddd, J=23.1, 10.2, 6.6 and 6.6), 4.95 (2H, m), 3.77 (3H, s), 3.52 (1H, m), 2.76 (1H, dd, J=11.7 and 3.0), 2.64 (1H, s), 2.39 (1H, dd, J=11.6 and 9.4), 2.03 (2H, m), 1.33 (10H, m), 1.05 (6H, s): $^{13}$C-NMR (CDCl$_3$) δ158.1, 139.1, 131.4, 129.8, 114.1, 113.4, 69.8, 55.2, 53.7, 47.8, 46.5, 35.1, 33.8, 29.6, 29.0, 28.8, 26.6, 26.4, 25.7; FT-IR (film) cm$^{-1}$ 3387 (broad, s), 1612, 1512, 1246, 1038, 910, 760.

Example 46
Preparation of N-(3-Dodecanoxy-2-hydroxypropyl)-1,1-dimethyl-2-(4-methoxyphenyl)ethylamine, Compound 72

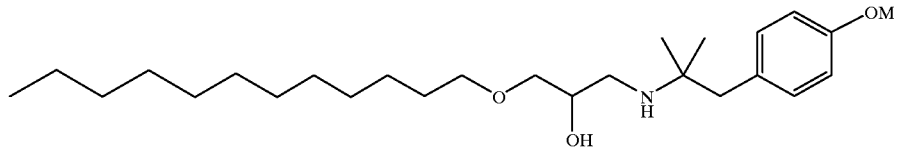

Using the method of Example 5, supra, dodecyl glycidyl ether (242 mg, 1.0 mmol) and 1,1-dimethyl-2-(4-methoxyphenyl)ethylamine (197 mg, 1.1 mmol) were used to prepare 121 mg of the title compound as a clear, colorless oil: GC/EI-MS, m/z (rel. int.) 422 (M+1, 1), 406 (4), 300 (100), 222 (11), 163 (23), 121 (34); $^1$H-NMR (CDCl$_3$) δ7.09 (2H, d, J=8.6), 6.83 (2H, d, J=8.6), 3.79 (3H, s), 3.76 (1H, m), 3.45 (4H, m), 2.81 (1H, dd, J=7.6 and 4.0), 2.65 (4H, m), 1.53 (2H, m), 1.26 (20H, m), 1.06 (3H, s), 1.05 (3H, s), 0.88 (3H, t, J=6.4); $^{13}$C-NMR (CDCl$_3$) δ158.1, 131.3, 130.0, 113.4, 73.5, 71.7, 69.0, 55.1, 53.4, 46.4, 44.6, 31.9, 29.6, 29.4, 29.3, 26.7, 26.6, 26.1, 22.7, 14.1; FT-IR (film) cm$^{-1}$ 3415 (broad, s), 1612, 1512, 1246, 1121, 825.

Example 47

Preparation of N-[2-Hydroxy-3-(1-adamantylmethoxy)propyl]-1,1-dimethyl-2-(4-methoxyphenyl)ethylamine Hydrochloride, Compound 74

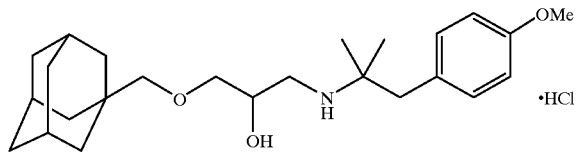

Using the method of Example 9, supra, 1,2-epoxy-3-(1-adamantylmethoxy)propane (410 mg, 1.8 mmol) and 1,1-dimethyl-2-(4-methoxyphenyl)ethylamine (403 mg, 2.25 mmol) were used to prepare 625 mg of the title compound as a white solid: GC/EI-MS, m/z (rel. int.) 386 (M–15, 5), 281 (97), 280 (100), 163 (26), 149 (77), 135 (23), 121 (63), 107 (18), 93 (29), 79 (20), 71 (26).

Example 48

Preparation of N-(2-Hydroxy-3-cyclohexylmethoxypropyl)-1,1-dimethyl-2-(4-methoxyphenyl)ethylamine Hydrochloride, Compound 75

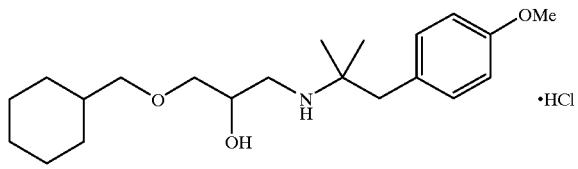

Using the method of Example 6, supra, 1,2-epoxy-3-cyclohexylmethoxypropane (212 mg, 1.2 mmol) and 1,1-dimethyl-2-(4-methoxyphenyl)ethylamine (279 mg, 1.6 mmol) were used to prepare 200 mg of the title compound as a white solid: GC/EI-MS, m/z (rel. int.) 334 (M–15, 0.1), 229 (15), 228 (100), 163 (9), 132 (5), 121 (16), 114 (9), 97 (7), 71 (8), 70 (9), 55 (16).

Example 49

Preparation of N-(2-Hydroxy-4-phenylbutyl)-1,1-dimethyl-2-(4-methoxyphenyl)ethylamine Hydrochloride, Compound 79

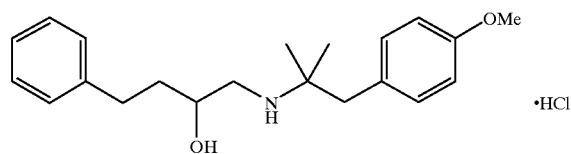

A solution of m-chloroperbenzoic acid (43.5 g, 151 mmol) in chloroform (250 ml) was treated with 4-phenyl-1-butene (20 g, 151 mmol). The reaction was stirred for 1 hour at room temperature and washed with sodium bicarbonate, sodium sulfite, and saturated sodium chloride. The solution was dried over sodium sulfate and evaporated to dryness to afford 3,4-epoxybutylbenzene (100%).

Using the method of Example 6, supra, 3,4-epoxybutylbenzene (1.4 mmol) and 1,1-dimethyl-2-(4-methoxyphenyl)ethylamine (1.7 mmol) were used to prepare 235 mg of the title compound as a white solid: GC/EI-MS, m/z (rel. int.) 312 (M–15, 0.1), 207 (16), 206 (100), 163 (7), 131 (28), 121 (19), 91 (28), 77 (7), 71 (7), 70 (10), 58 (10).

Example 50

Preparation of N-(2-Hydroxy-3-phenoxypropyl)-1,1-dimethyl-3-(4-methoxyphenyl)propylamine Hydrochloride, Compound 90

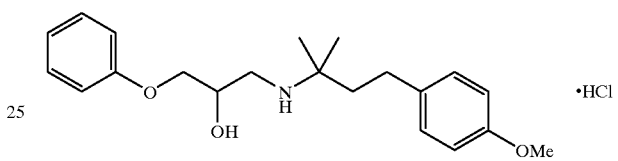

4-Methoxycinnamonitrile was hydrogenated in ethanol with palladium hydroxide on carbon to give 3-(4-methoxyphenyl)propionitrile. A mixture of anhydrous cerium (III) chloride (1.99 g, 8.1 mmol) in dry THF (12 mL) was stirred for 3 hours at room temperature, cooled to –78° C., and treated with MeLi (5.8 mL, 8.1 mmol). After stirring for 1 hour at –78° C. the reaction mixture was treated with 3-(4-methoxyphenyl)propionitrile (0.45 g, 2.8 mmol). The reaction mixture was stirred for 5 hours at –78° C. and then quenched with ammonium hydroxide. After warming to room temperature, the mixture was filtered, and the filtrate diluted with water and extracted with diethyl ether. The diethyl ether layer was dried over sodium sulfate and evaporated. The crude oil was purified by normal-phase chromatography to give 150 mg of 1,1-dimethyl-2-(4-methoxyphenyl)ethylamine as a light yellow oil.

Using the method of Example 6, supra, 1,2-epoxy-3-phenoxypropane (0.62 mmol) and 1,1-dimethyl-2-(4-methoxyphenyl)ethylamine (0.78 mmol) were used to prepare 105 mg of the title compound as a white solid: GC/EI-MS, m/z (rel. int.) 343 (M+, 4), 209 (14), 208 (99), 161 (13), 122 (9), 121 (100), 77 (17), 72 (25), 71 (12), 70 (18), 58 (13).

Example 51

Preparation of N-[2-Hydroxy-3-(1-adamantanoxy)propyl]-1,1-dimethyl-2-(4-methoxyphenyl)ethylamine, Compound 96

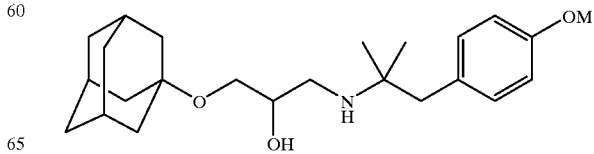

Using the method of Example 16, supra, 1-adamantyl glycidyl ether (350 mg, 1.0 mmol) and 1,1-dimethyl-2-(4-methoxyphenyl)ethylamine (197 mg, 1.1 mmol) were used to prepare 207 mg of the title compound as a clear, colorless oil: GC/EI-MS, m/z (rel. int.) 338 (M+1, 0.1), 372 (0.3), 266 (65), 163 (1), 135 (100), 121 (16); $^1$H-NMR (CDCl$_3$) δ7.02 (2H, d, J=8.3), 6.74 (2H, d, J=8.6), 3.70 (3H, s), 3.64 (1H, m), 3.38 (4H, m), 2.71 (1H, dd, J=11.5 and 4.0), 2.57 (3H, m), 2.06 (3H, broad s), 1.64 (6H, broad s), 1.53 (6H, m), 1.13 (4H, apparent t, J=6.9), 0.98 (3H, s), 0.97 (3H, s); $^{13}$C-NMR (CDCl$_3$) δ157.8, 131.2, 130.0, 113.1, 77.8, 70.5, 69.4, 54.9, 52.8, 46.3, 44.6, 32.0, 26.7, 26.6, 25.6, 23.9.

Example 52
Preparation of N-(2-Hydroxy-3-phenoxypropyl)-1,1-dimethyl-2-(4-methylphenyl)ethylamine Hydrochloride, Compound 98

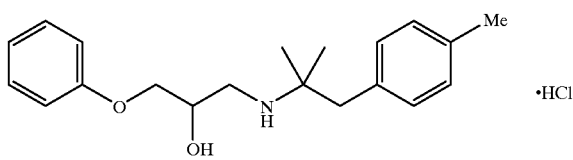

A solution of 2,4,6-triphenylpyrylium tetrafluoroborate (2.97 g, 7.5 mmol) in ethanol (15 mL) was treated with 4-methylbenzylamine (1 g, 8.25 mmol). The reaction was stirred overnight at room temperature and diluted with diethyl ether to precipitate the product. The product was recrystallized from ethanol/diethyl ether to give 3.15 g of N-(4-methylbenzyl)-2,4,6-triphenylpyridinium tetrafluoroborate as a tan solid.

Sodium hydride (0.92 g, 60% oil dispersion, 22.9 mmol) was added to methanol (10 mL) at 0° C., followed by the addition of 2-nitropropane (2.04 g, 22.9 mmol). The reaction mixture was stirred for 30 minutes at room temperature and the methanol was evaporated at reduced pressure. A solution of the N-(4-methylbenzyl)-2,4,6-triphenylpyridinium tetrafluoroborate (3.15 g, 7.6 mmol) in DMSO (25 mL) was then added to the dry sodium salt of 2-nitropropane. The mixture was stirred at 60° C. overnight under nitrogen. The reaction was diluted with water, and the product extracted into diethyl ether. The ether layer was washed with saturated NaCl and dried over sodium sulfate. The ether solution was treated with Amberlyst 15 ion-exchange resin to absorb the 2,4,6-triphenylpyridine. The resin was filtered and the filtrate evaporated to yield 1.3 g of pure 1-(4-methylphenyl)-2-methyl-2-nitropropane.

The 1-(4-methylphenyl)-2-methyl-2-nitropropane (1.3 g) was hydrogenated for 5 hours at 65 p.s.i. hydrogen in ethanol (30 mL) using 1.4 g of Raney nickel as catalyst. Removal of the catalyst by filtration and evaporation of the solvent yielded 1.15 g of 1,1-dimethyl-2-(4-methoxyphenyl) ethylamine as a clear oil.

Using the method of Example 6, supra, 1,2-epoxy-3-phenoxypropane (1.3 mmol) and 1,1-dimethyl-2-(4-methoxyphenyl)ethylamine (0.6 mmol) were used to prepare 85 mg of the title compound as a white solid: GC/EI-MS, m/z (rel. int.) 298 (M–15, 7), 209 (47), 208 (100), 114 (14), 107 (13), 105 (46), 79 (12), 77 (28), 71 (18), 70 (31), 58 (13).

Example 53
Preparation of N-(2-Hydroxy-3-phenoxypropyl)-1,1-dimethyl-2-(3-methoxyphenyl)ethylamine Hydrochloride, Compound 99

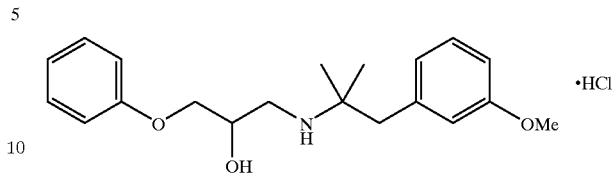

Using the method of Example 6, supra, 1,2-epoxy-3-phenoxypropane (200 mg, 1.3 mmol) and 1,1-dimethyl-2-(3-methoxyphenyl)ethylamine (263 mg, 1.5 mmol) were used to prepare 340 mg of the title compound as a white solid: GC/EI-MS, m/z (rel. int.) 209 (14), 208 (100), 206 (6), 121 (11), 114 (5), 107 (5), 91 (6), 77 (12), 71 (8), 70 (16).

Example 54
Preparation of N-(2-Hydroxy-2-methyl-3-phenoxypropyl)-1,1-dimethyl-2-(4-methoxyphenyl)ethylamine Hydrochloride, Compound 101

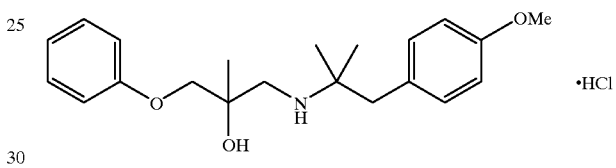

To a solution of 3-chloroperoxybenzoic acid (70% pure, 4.2 g, 17 mmol) in 40 mL of chloroform was added methallyl phenyl ether (2.5 g, 16.87 mmol). The mixture was stirred at room temperature for 5 hours then worked up by pouring into ether and sodium bicarbonate. The organic phase was washed with sodium bisulfite, sodium bicarbonate, and sodium chloride, dried over anhydrous sodium sulfate and evaporated to give 2.3 g of 1,2-epoxy-2-methyl-3-phenoxypropane.

Using the method of Example 6, supra, 1,2-epoxy-2-methyl-3-phenoxypropane (0.092 g, 0.56 mmol) and 1,1-dimethyl-2-(4-methoxyphenyl)ethylamine (0.10 g, 0.56 mmol) were used to prepare 120 mg of the title compound as a white solid: GC/EI-MS, m/z, (rel. int.) 328 (M–15,1), 223 (15), 222 (100), 163 (13), 147 (13), 121 (21), 107 (11), 91 (9), 77 (13) 71 (12), 70 (49).

Example 55
Preparation of N-(2-Hydroxy-3-phenoxypropyl)-1,1-dimethyl-2-(4-chlorophenyl)ethylamine Hydrochloride, Compound 103

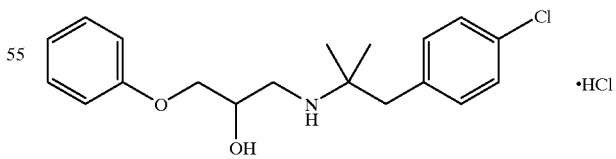

Using the method of Example 6, supra, 1,2-epoxy-3-phenoxypropane (950 mg, 6.3 mmol) and 1,1-dimethyl-2-(4-chlorophenyl)ethylamine (1.45 g, 7.9 mmol) were used to prepare 150 mg of the title compound as a white solid: GC/EI-MS, m/z (rel. int.) 318 (M–15, 7), 209 (47), 208 (100), 127 (11), 125 (33), 114 (13), 107 (12), 77 (23), 71 (16), 70 (29), 58 (13).

Example 56
Preparation of N-(2-Hydroxy-3-phenoxypropyl)-1,1-dimethyl-2-(3-chlorophenyl)ethylamine Hydrochloride, Compound 104

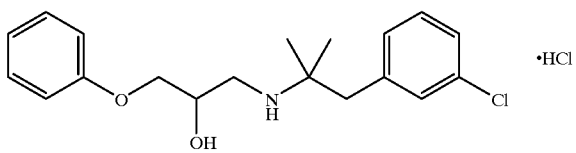

Using the method of Example 6, supra, 1,2-epoxy-3-phenoxypropane (1.3 g, 8.8 mmol) and 1,1-dimethyl-2-(4-chlorophenyl)ethylamine (2.0 g, 11 mmol) were used to prepare 338 mg of the title compound as a white solid: GC/EI-MS, m/z (rel. int.) 318 (M–15, 1), 209 (14), 208 (100), 133 (4), 125 (12), 114 (6), 107 (6), 77 (10), 71 (8), 70 (15), 58 (5).

Example 57
Resolution of the Enantiomers of (R)- and (S)-N-[2-Hydroxy-3-(1-naphthoxy)propyl]-1,1-dimethyl-2-(4-methoxyphenyl)ethylamine Hydrochloride, Compounds 105 and 106

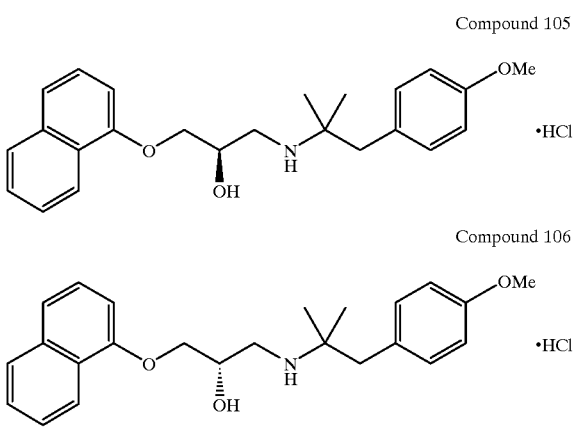

The free base (1.5 g) of compound 19 was chromatographed through ChiralCel OD (20×2.5 cm) using ethanol-hexane (1:4, plus 0.1% diethylamine) at 10 mL/min (270 nm). Chromatography of each enantiomer through Vydac C-18 (5×25 cm) using a gradient of 0.1% HCl to acetonitrile (50 mL/min., 264 nm) afforded the hydrochloride salt of compound 105 (464 mg) $[\alpha]_D^{26}$=15.3° (c=0.928, $CHCl_3$), m.p. 113–115° C. and compound 106 (463 mg) $[\alpha]_D^{26}$=–13.8° (c=0.926, $CHCl_3$).

Example 58
Preparation of N-[2-Hydroxy-3-(4-methoxy-(1-naphthoxy))propyl]-1,1-dimethyl-2-(4-methoxyphenyl)ethylamine Hydrochloride, Compound 107

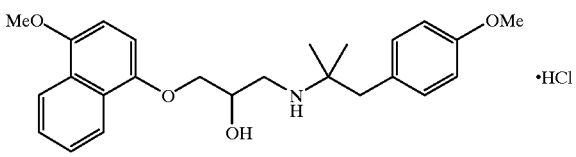

Using the method of Example 5, supra, 1,2-epoxy-3-[4-methoxy-(1-naphthoxy)]propane (462 mg, 2 mmol) and 1,1-dimethyl-2-(4-methoxyphenyl)ethylamine (120 mg, 0.67 mmol) yielded, after preparative TLC and RP-HPLC, 116 mg of the title compound as a white solid: GC/EI-MS, m/z (rel. int.) 394 (M–15,2), 288 (100), 731 (11), 121 (15), 71 (22).

Example 59
Preparation of N-[2-Hydroxy-3-(4-chloro-(1-naphthoxy))propyl]-1,1-dimethyl-2-(4-methoxyphenyl)ethylamine Hydrochloride, Compound 108

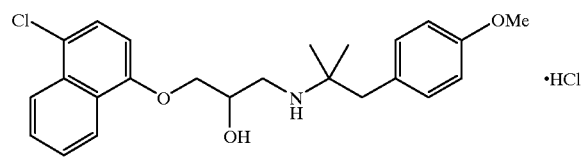

Using the method of Example 5, supra, 1,2-epoxy-3-[4-chloro-(1-naphthoxy)]propane (469 mg, 2 mmol) and 1,1-dimethyl-2-(4-methoxyphenyl)ethylamine (120 mg, 0.67 mmol) yielded, after preparative TLC and RP-HPLC, 131 mg of the title compound as a white solid: GC/EI-MS, m/z (rel. int.) 414 ($M^+$, 0.5), 398 (1), 292 (100), 121 (33), 71 (43).

Example 60
Preparation of (R)-N-[2-Hydroxy-3-(3-chloro-2-cyanophenoxy)propyl]-1,1-dimethyl-2-(4-methoxyphenyl)-ethylamine Hydrochloride, Compound 109

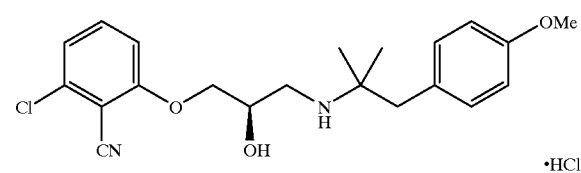

To a solution of 18-crown-6 (3.96 g, 15 mmol) in 30 mL of acetonitrile were added dry potassium acetate (1.47 g, 15 mmol) and 2-chloro-6-fluorobenzonitrile (1.56 g, 10 mmol). The reaction was refluxed under nitrogen for 25 hours, then cooled to room temperature. Sodium hydroxide (2 mL of a 10 M solution, 20 mmol) and water (5 mL) were added, and the reaction stirred at room temperature for two hours. The acetonitrile was removed on a rotary evaporator, and the residue was taken up in ether and water. The basic aqueous layer was washed three times with ether. The aqueous layer was then made acidic with HCl, and the product extracted into ether. The ether layer was dried over anhydrous sodium sulfate, filtered, and concentrated. The resulting solid was crystallized from water/methanol to yield 1.11 g of 3-chloro-2-cyanophenol.

3-Chloro-2-cyanophenol (0.55 g, 3.58 mmol) was dissolved in 10 mL of dimethylformamide, and the solution cooled to 0° C. Sodium hydride (0.158 g, 3.94 mmol 60% in oil), washed with hexane and dimethylformamide, was added to cooled solution over a period of one minute. After stirring for 10 minutes at room temperature, (2R)-(−)-glycidyl 3-nitrobenzenesulfonate was added and stirred 16 hours. The reaction was poured into ether and dilute sodium hydroxide. The ether layer was separated and the aqueous layer extracted once more with ether. The combined ether extracts were washed with water and saturated brine, dried over anhydrous sodium sulfate, filtered, and concentrated to give 0.7 g of (R)-3-chloro-2-cyanophenyl glycidyl ether.

Using the method of Example 6, supra, (R)-3-chloro-2-cyanophenyl glycidyl ether (0.7 g, 3.34 mmol) and 1,1-dimethyl-(4-methoxyphenyl)ethylamine (0.72 g, 4.0 mmol) were used to prepare 570 mg of the title compound as a white solid: $^1$H-NMR (CDCl$_3$) 9.65 (1H, br s), 8.2 (1H, br s), 7.4 (1H, t), 7.15 (2H, d), 7.03 (1H, d), 6.95 (1H, d), 6.8 (2H, d), 4.8 (1H, m), 4.3 (2H, d), 3.75 (3H, s), 3.4 (2H, m), 3.13 (2H, dd), 1.44 (3H, s), 1.40 (3H, s); $^{13}$C-NMR 161.9, 159.4, 138.2, 135.1, 132.4, 126.8, 122.8, 114.4, 114.2, 111.6, 104.0, 71.8, 66.0, 61.9, 55.8, 45.4, 43.9, 23.5, 23.3.

Example 61

Preparation of N-(2-Hydroxy-3-phenoxypropyl)-1,1-dimethyl-2-(4-ethylphenyl)ethylamine Hydrochloride, Compound 110

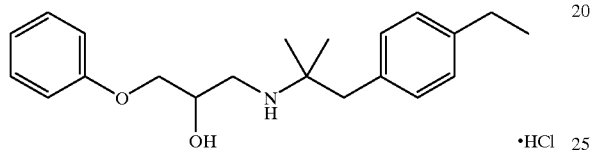

Using the method of Example 52, supra, 4-ethylbenzylamine (4.0 g, 29.6 mmol) was used to prepare 3.6 g of 1,1-dimethyl-2-(4-ethylphenyl)ethylamine. Using the method of Example 6, supra, 1,2-epoxy-3-phenoxypropane (0.43 g, 2.9 mmol) and 1,1-dimethyl-2-(4-ethylphenyl)ethylamine (0.5 g, 2.8 mmol) were used to prepare 600 mg of the title compound as a white solid: GC/EI-MS, m/z, (rel. int.) 313 (M−15,0.1), 209 (23), 208 (100), 133 (5), 119 (12), 114 (6), 107 (5), 104 (7), 91 (6), 77 (10), 71 (8), 70 (12).

Example 62

Preparation of N-(2-Hydroxy-3-phenoxypropyl)-1,1-dimethyl-2-(4-trifluoromethoxyphenyl)ethylamine Hydrochloride, Compound 111

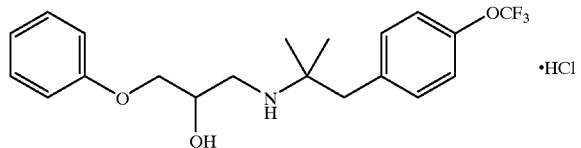

Using the method of Example 52, supra, 4-trifluoromethoxybenzylamine (2.0 g, 10.5 mmol) was used to prepare 2.2 g of 1,1-dimethyl-2-(4-trifluoromethoxyphenyl)ethylamine.

Using the method of Example 6, supra, 1,2-epoxy-3-phenoxypropane (0.12 g, 0.8 mmol) and 1,1-dimethyl-2-(4-trifluoromethoxyphenyl)ethylamine (0.175 g, 0.8 mmol) were used to prepare 15 mg of the title compound as a white solid: GC/EI-MS, m/z, (rel. int.) 368 (M−15,2), 209 (39), 208 (100), 175 (20), 133 (5), 114 (5), 107 (6), 77 (11), 71 (7), 70 (12), 58 (5).

Example 63

Preparation of N-(2-Hydroxy-3-phenoxypropyl)-1,1-dimethyl-2-(4-isopropylphenyl)ethylamine Hydrochloride, Compound 112

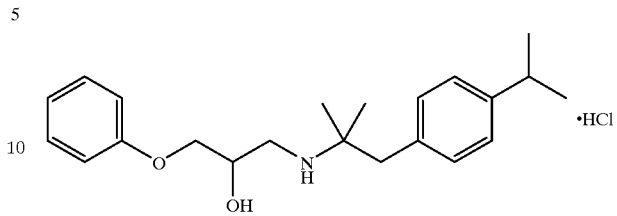

Using the method of Example 52, supra, 4-isopropylbenzylamine (4.89 g, 32.8 mmol) was used to prepare 4.1 g of 1,1-dimethyl-2-(4-isopropylphenyl)ethylamine. Using the method of Example 6, supra, 1,2-epoxy-3-phenoxypropane (0.173 g, 1.15 mmol) and 1,1-dimethyl-2-(4-isopropylphenyl)ethylamine (0.275 g, 1.44 mmol) were used to prepare 89 mg of the title compound as a white solid: GC/EI-MS, m/z, (rel. int.) 326 (M−15,1), 209 (14), 208 (100), 133 (9), 117 (5), 114 (5), 105 (5), 91 (6), 77 (8), 71 (8), 70 (13), 58 (5).

Example 64

Preparation of N-(2-Hydroxy-3-phenoxypropyl)-1-ethyl-1-methyl-2-(4-methoxyphenyl)ethylamine Hydrochloride, Compound 113

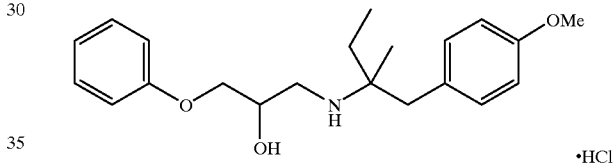

4-Hydroxybenzyl alcohol (0.35 g, 2.82 mmol) and tetrabutylammonium fluoride (0.147 g, 0.56 mmol) were dissolved in 3 mL of 2-nitrobutane and heated to 130–145° C. under nitrogen for 20 hours. The reaction mixture was cooled and partitioned between water and ether. The ether layer was separated, washed with saturated brine, dried over anhydrous sodium sulfate, and concentrated. The crude material was purified by preparative TLC using ethyl acetate/hexane as the elutant. The yield of 1-ethyl-1-methyl-2-(4-hydroxyphenyl)nitroethane was 0.21 grams.

To a suspension of 40% (wt/wt) potassium fluoride on alumina (0.73 g, 5 mmol) in 3 mL of acetonitrile were added 1-ethyl-1-methyl-2-(4-hydroxyphenyl)nitroethane (0.21 g, 1.0 mmol) and iodomethane (0.21 g, 1.5 mmol). The reaction was stirred at room temperature for 4 days and then filtered and rinsed with acetonitrile. The acetonitrile was removed on a rotary evaporator, and the residue was partitioned between ether and water. The ether layer was separated, washed with sodium bisulfite, sodium carbonate, and saturated brine, then dried over anhydrous sodium sulfate and concentrated. The yield of 1-ethyl-1-methyl-2-(4-methoxyphenyl)nitroethane was 0.183 g.

Nickel chloride monohydrate (0.107 g, 0.404 mmol) was dissolved in 5 mL of methanol, followed by the addition of sodium borohydride (0.05 g, 1.2 mmol). After stirring for 5 minutes, 1-ethyl-1-methyl-2-(4-methoxyphenyl)nitroethane (0.18 g, 0.807 mmol) in 3 mL of methanol was added, and stirred for 5 minutes. Sodium borohydride (0.11 g, 2.83 mmol) was then added in portions over 5 minutes. The reaction was then stirred overnight under a hydrogen balloon. The reaction mixture was filtered, and the methanol was removed on a rotary evaporator. The residue was taken up in ether and dilute sodium hydroxide. The ether layer was separated, washed with saturated brine, dried over anhydrous sodium sulfate, and concentrated. The yield of 1-ethyl-1-methyl-2-(4-methoxy-phenyl)ethylamine was 0.127 grams.

Using the method of Example 6, supra, 1,2-epoxy-3-phenoxypropane (0.086 g, 0.57 mmol) and 1-ethyl-1-methyl-2-(4-methoxyphenyl)ethylamine (0.11 g, 0.57 mmol) were used to prepare 90 mg of the title compound as a white solid: GC/EI-MS, m/z, (rel. int.) 314 (M−29,2), 223 (15), 222 (100), 128 (6), 121 (20), 107 (5), 84 (10), 78 (5), 77 (12), 72 (5), 56 (7).

Example 65

Preparation of N-(2-Hydroxy-3-phenoxypropyl)-1,1-diethyl-2-(4-methoxyphenyl)ethylamine Hydrochloride, Compound 114

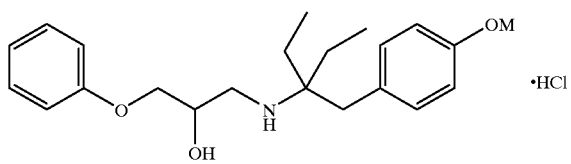

Anhydrous cerium (III) chloride (13.6 g, 55.2 mmol) was suspended in 80 mL of dry terahydrofuran, and stirred under nitrogen for 16 hours. This suspension was cooled in an ice bath, and ethylmagnesium chloride (27.6 mL, 55.18 mmol, 2 M solution in tetrahydrofuran) was added over 5 minutes. After stirring for 1 hour, methyl 4-methoxyphenylacetate (3.98 g, 22.07 mmol) was added to the suspension and stirred for another 2 hours. The reaction was then partitioned between ether and saturated ammonium chloride. The ether layer was separated, washed with dilute HCl, water, and saturated brine, dried over anhydrous sodium sulfate, and concentrated. The yield of 1,1-diethyl-2-(4-methoxyphenyl) ethanol was 4.65 g.

Powdered sodium cyanide (1.18 g, 24 mmol) was placed in a flask and covered with 5.5 mL of acetic acid. A mixture of sulfuric acid (3 mL) and acetic acid (2.75 mL) was cooled to 0° C. and then added to the cyanide suspension over a period of 3 minutes. The mixture was stirred for 30 minutes at room temperature, followed by the addition of 1,1-diethyl-2-(4-methoxyphenyl)ethanol (4.6 g, 22 mmol). The mixture was stirred overnight then poured into ice and sodium hydroxide. The product was extracted with ether, and the ether layer dried over anhydrous sodium sulfate, and concentrated. The residue was suspended in 20% sodium hydroxide and refluxed overnight under nitrogen. The reaction was cooled, diluted with water, and extracted with ether. The ether layer was separated, washed with saturated brine, dried over anhydrous sodium sulfate, and concentrated. The residue was purified by reversed-phase HPLC (C-18 using 0.1% HCl/acetonitrile as the elutant) to give 1.91 g of 1,1-diethyl-2-(4-methoxyphenyl)ethylamine.

Using the method of Example 6, supra, 1,2-epoxy-3-phenoxypropane (0.15 g, 1.0 mmol) and 1,1-diethyl-2-(4-methoxyphenyl)ethylamine (0.249 g, 1.2 mmol) were used to prepare 244 mg of the title compound as a white solid: GC/EI-MS, m/z, (rel. int.) 328 (M−29,6), 237 (17), 236 (100), 121 (22), 106 (5), 98 (7), 78 (5), 77 (11), 70 (7), 56 (5).

Example 66

Preparation of (R)-N-[2-Hydroxy-3-(2,3-dichlorophenoxy)propyl]-1,1-dimethyl-2-(4-methoxyphenyl)ethylamine Hydrochloride, Compound 115

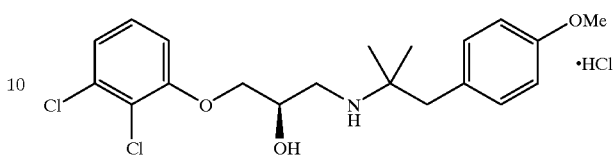

2,3-Dichlorophenol (0.69 g, 4.24 mmol) was dissolved in 15 mL of acetone, followed by the addition of powdered potassium carbonate (1.6 g, 11.57 mmol). This mixture was stirred for 2 hours then (2R)-(−)-glycidyl 3-nitrobenzenesulfonate was added and stirred overnight. The reaction was worked up by pouring into water and ether. The ether layer was separated, washed with saturated brine, dried over anhydrous sodium sulfate, and concentrated. The yield of (R)-2,3-dichlorophenyl glycidyl ether was 0.837 g.

Using the method of Example 6, supra, (R)-2,3-dichlorophenyl glycidyl ether (0.837 g, 3.82 mmol) and 1,1-dimethyl-2-(4-methoxyphenyl)ethylamine (0.75 g, 4.18 mmol) were used to prepare 860 mg of the title compound as a white solid: GC/EI-MS, m/z, (rel. int.) 382 (M−15,0.1), 280 (11), 278 (64), 277 (16), 276 (100), 163 (10), 121 (35), 77 (10), 71 (24), 70 (27), 58 (12).

Example 67

Preparation of (S)-N-[2-Hydroxy-3-(2,3-dichlorophenoxy)propyl]-1,1-dimethyl-2-(4-methoxyphenyl)ethylamine Hydrochloride, Compound 116

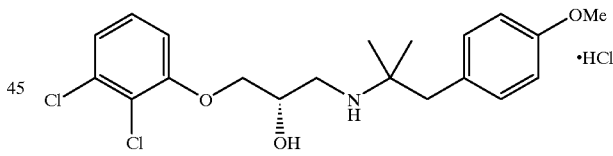

2,3-Dichlorophenol (0.69 g, 4.24 mmol) was dissolved in 15 mL of acetone, followed by the addition of powdered potassium carbonate (1.6 g, 11.57 mmol). This mixture was stirred for 2 hours then (2S)-(+)-glycidyl 3-nitrobenzenesulfonate was added and stirred overnight. The reaction was worked up by pouring into water and ether. The ether layer was separated, washed with saturated brine, dried over anhydrous sodium sulfate, and concentrated. The yield of (S)-2,3-dichlorophenyl glycidyl ether was 0.84 g.

Using the method of Example 6, supra, (S)-2,3-dichlorophenyl glycidyl ether (0.84 g, 3.82 mmol) and 1,1-dimethyl-2-(4-methoxyphenyl)ethylamine (0.75 g, 4.18 mmol) were used to prepare 860 mg of the title compound as a white solid: GC/EI-MS, m/z, (rel. int.) 382 (M−15,0.1), 280 (10), 279 (9), 278 (63), 276 (100), 163 (11), 121 (28), 77 (7), 71 (21), 70 (23), 58 (10).

Example 68
Preparation of N-(2-Hydroxy-3-phenoxypropyl)-1,1-dimethyl-2-(4-methoxy-3-methylphenyl)ethylamine Hydrochloride, Compound 117

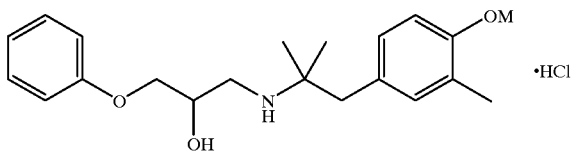

Using the method of Example 64, supra, 4-hydroxy-3-methylbenzyl alcohol (1.0 g, 7.25 mmol), 2-nitropropane (5 mL), and tetrabutylammonium fluoride (0.38 g, 0.145 mmol) were used to prepare 0.8 g of 1,1-dimethyl-2-(4-methoxy-3-methylphenyl)ethylamine.

Using the method of Example 6, supra, 1,2-epoxy-3-phenoxypropane (0.151 g, 1.0 mmol) and 1,1-dimethyl-2-(4-methoxy-3-methylphenyl)ethylamine (0.2 g, 1.0 mmol) were used to prepare 130 mg of the title compound as a white solid: GC/EI-MS, m/z, (rel. int.) 328 (M–15,0.1), 209 (14), 208 (100), 177 (5), 135 (14), 114 (5), 91 (6), 76 (9), 71 (8), 70 (13), 58 (5).

Example 69
Preparation of N-[2-Hydroxy-3-(2-cyano-3-methoxyphenoxy)propyl]-1,1-dimethyl-2-(4-methoxyphenyl)ethylamine Hydrochloride, Compound 118

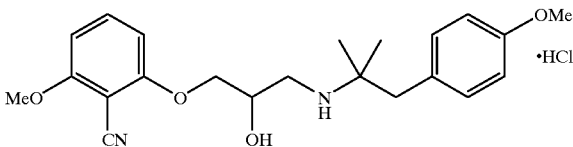

Powdered sodium cyanide (9.0 g, 184 mmol) and 2,6-dimethoxybenzonitrile were added to 50 mL of dimethylsulfoxide and heated to 145° C. for 110 min under nitrogen. The reaction was cooled and poured into ether and dilute HCl. The ether layer was separated, washed twice with dilute acid, once with saturated brine, dried over anhydrous sodium sulfate, and concentrated. The yield of 2-cyano-3-methoxyphenol was 8.1 g.

2-Cyano-3-methoxyphenol (1 g, 6.7 mmol) and powdered potassium carbonate (2.78 g, 20.1 mmol) were stirred in 15 mL of acetone for 5 minutes, followed by addition of epibromohydrin (1.38 g, 10.1 mmol). The mixture was stirred for 72 hours then poured into water/ether. The ether layer was separated, washed with sodium carbonate and saturated brine, dried over anhydrous sodium sulfate, and concentrated. The resulting crude solid was triturated with ether/hexane, filtered, and dried under vacuum to give 0.44 g of 2-cyano-3-methoxyphenyl glcidyl ether.

Using the method of Example 6, supra, 2-cyano-3-methoxyphenyl glcidyl ether (0.205 g, 1.0 mmol) and 1,1-dimethyl-2-(4-methoxyphenyl)ethylamine (0.215 g, 1.2 mmol) were used to prepare 265 mg of the title compound as a white solid: $^1$H-NMR (CDCl$_3$) δ9.6 (1H, br s), 8.2 (1H, br s), 7.4 (1H, t), 7.15 (2H, d), 6.8 (2H, d), 6.6 (1H, d), 6.53 (1H, d), 4.75 (1H, m), 4.25 (2H, m), 3.87 (3H, s), 3.77 (3H, s), 3.43 (2H, m), 3.12 (2H, dd), 1.45 (3H, s), 1.41 (3H, s). $^{13}$C-NMR δ162.9, 162, 159.3, 135.5, 132.4, 127, 114.7, 114.4, 105.6, 104.6, 92.2, 71.4, 66.1, 61.9, 56.8, 55.8, 45.4, 43.8, 23.5, 23.3.

Example 70
Preparation of N-[2-Hydroxy-3-(3-chloro-2-cyanophenoxy)propyl]-1,1-dimethyl-2-(4-methoxyphenyl)ethylamine Hydrochloride, Compound 119

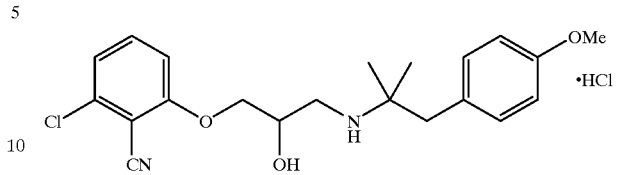

Using the method of Example 69, supra, 3-chloro-2-cyanophenol (made using the method of Example 60, supra) (0.48 g, 3.13 mmol), potassium carbonate (1.3 g, 9.38 mmol), and epibromohydrin (0.86 g, 6.25 mmol) were used to prepare 93 mg of 3-chloro-2-cyanophenyl glycidyl ether.

Using the method of Example 6, supra, 3-chloro-2-cyanophenyl glycidyl ether (0.093 g, 0.44 mmol) and 1,1-dimethyl-(4-methoxyphenyl)ethylamine (0.095 g, 0.53 mmol) were used to prepare 134 mg of the title compound as a white solid: $^1$H-NMR (CDCl$_3$) δ9.68 (1H, br s), 8.2 (1H, br s), 7.4 (1H, t), 7.15 (2H, d), 7.03 (1H, d), 6.95 (1H, d), 6.8 (2H, d), 5.7 (1H, br s), 4.8 (1H, m), 4.3 (2H, d), 3.75 (3H, s), 3.4 (2H, m), 3.13 (2H, dd), 1.44 (3H, s), 1.40 (3H, s).

Example 71
Preparation of N-(2-Hydroxy-3-phenoxypropyl)-1,1-dimethyl-2-(2-naphthyl)ethylamine Hydrochloride, Compound 120

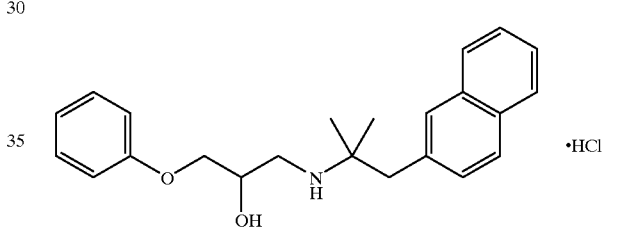

Using the method of Example 52, supra, 2-aminomethylnaphthalene (2.51 g, 16 mmol) was used to prepare 1.9 g of 1,1-dimethyl-2-(2-naphthyl)ethylamine.

Using the method of Example 6, supra, 1,2-epoxy-3-phenoxypropane (0.163 g, 1.1 mmol) and 1,1-dimethyl-2-(2-naphthyl)ethylamine (0.26 g, 1.3 mmol) were used to prepare 243 mg of the title compound as a white solid: GC/EI-MS, m/z, (rel. int.) 334 (M–15,0.1), 209 (14), 208 (100), 141 (16), 115 (7), 76 (5), 70 (7).

Example 72
Preparation of N-(2-Hydroxy-3-phenoxy)propyl)-1,1-dimethyl-2-(3,4-dimethylphenyl) ethylamine Hydrochloride, Compound 121

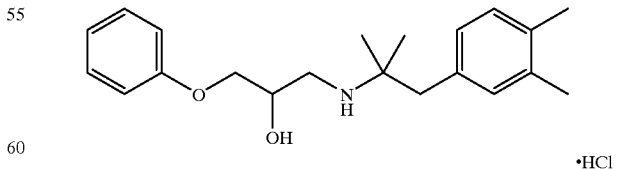

Using the method of Example 52, supra, 3,4-dimethylbenzylamine (5 g, 37 mmol) was used to prepare 2.29 g of 1,1-dimethyl-2-(3,4-dimethylphenyl)ethylamine.

Using the method of Example 6, supra, 1,2-epoxy-3-phenoxypropane (0.165 g, 1.1 mmol) and 1,1-dimethyl-2-

(3,4-dimethylphenyl)ethylamine (0.22 g, 1.2 mmol) were used to prepare 268 mg of the title compound as a white solid: GC/EI-MS, m/z, (rel. int.) 312 (M–15,1), 209 (14), 208 (100), 133 (5), 119 (13), 114 (5), 107 (5), 91 (5), 76 (10), 71 (8), 70 (14), 58 (6).

Example 73

Preparation of (R)-N-[2-Hydroxy-3-(2-cyanophenoxy) propyl]-1,1-dimethyl-2-(4-methoxyphenyl)ethylamine Hydrochloride, Compound 122

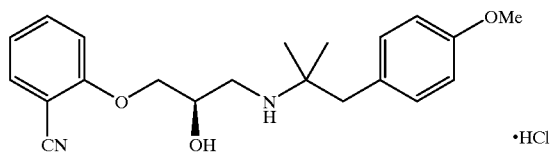

Using the method of Example 60, supra, 2-cyanophenol (0.54 g, 4.5 mmol), sodium hydride (0.188 g, 4.7 mmol), and (2R)-(–)-glycidyl 3-nitrobenzenesulfonate (1.06 g, 4.1 mmol) were used to prepare 350 mg of (R)-2-cyanophenyl glycidyl ether.

Using the method of Example 6, supra, (R)-2-cyanophenyl glycidyl ether (0.35 g, 2.0 mmol) and 1,1-dimethyl-(4-methoxyphenyl)ethylamine (0.35 g, 1.96 mmol) were used to prepare 600 mg of the title compound as a white solid: $^1$H-NMR (CDCl$_3$) δ9.7 (1H, br s), 8.2 (1H, br s), 7.5 (2H, m), 7.15 (2H, d), 7.0 (2H, m), 6.8 (2H, d), 4.8 (1H, br m), 4.25 (2H, m), 3.75 (3H, s), 3.45 (2H, m), 3.12 (2H, dd), 1.45 (3H, s), 1.41 (3H, s).

Example 74

Preparation of N-(2,10-Dihydroxydecyl)-1,1-dimethyl-2-(4-methoxyphenyl)ethylamine Hydrochloride, Compound 123

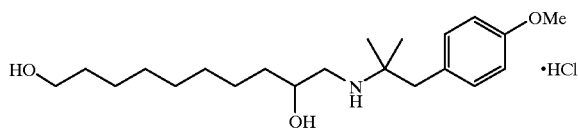

Using the method of Example 9, supra, 1,2-epoxy-10-hydroxydecane (172 mg, 1 mmol) and 1,1-dimethyl-2-(4-methoxyphenyl)ethylamine (230 mg, 1.5 mmol) were used to prepare the hydrochloride salt of the title compound. MPLC of the free amine (silica gel, 1% MeOH/CHCl$_3$), followed by treatment with an excess of 1 M HCl/ether, yielded 130 mg of the title compound as a white powder: GC/EI-MS, m/z (rel. int.) 336 (M$^+$–15, 0.1), 231 (14), 230 (100), 212 (9), 163 (10), 122 (5), 121 (42), 91 (8), 78 (6), 77 (5), 71 (13), 70 (11), 58 (8), 55 (8), 41 (6).

Example 75

Preparation of N-[2-hydroxy-3-(3,4-methylene-dioxyphenyl)propyl]-1,1-dimethyl-2-(4-methoxyphenyl)-ethylamine Hydrochloride, Compound 124

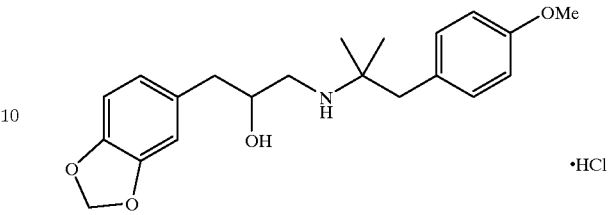

Safrole oxide was prepared by stirring a solution of safrole (1.48 mL, 10 mmol) and m-chloroperoxybenzoic acid (2.70 g, 11 mmol) in methylene dichloride (25 mL) overnight. The reaction was quenched by pouring into water (50 mL). The aqueous was extracted with ether (3×25 mL). The organic layers were combined and washed with 10% aqueous sodium sulfate (2×25 mL), saturated aqueous sodium bicarbonate (3×25 mL), and brine (25 mL). The organic phase was dried over magnesium sulfate and the solvents were removed in vacuo. The resulting yellow oil was used without further purification.

To a solution of safrole oxide (196 mg, 1.1 mmol) in acetonitrile (1.0 mL) was added lithium perchlorate (107 mg). The solution was stirred at ambient temperature to dissolve all of the solid lithium perchlorate. To this solution was added 1,1-dimethyl-2-(4-methoxyphenyl)ethylamine (180 mg, 1.0 mmol) and the reaction was stirred at 50° C. overnight. To the cooled reaction mixture was added water (5 mL) and was subsequently extracted with methylene dichloride (3×1 mL). The combined organic phases were washed with water (1 mL) and brine (1 mL) and dried over magnesium sulfate. The crude orange oil was purified (MPLC, silica gel, 1% MeOH/CHCl$_3$) and dissolved in methylene dichloride (5 mL). The hydrochloride salt was prepared by adding an excess of 1 M HCl/ether. The solvents were removed in vacuo to yield 139 mg of thick oil: GC/EI-MS, m/z (rel. int.) 342 (M$^+$, 0.1), 237 (15), 236 (100), 163 (5), 136 (6), 135 (61), 121 (23), 78 (7), 77 (13), 70 (15), 58 (7).

Example 76

Preparation of N-[2-hydroxy-3-(3,4-methylene-dioxyphenoxy)propyl]-1,1-dimethyl-2-(4-methoxyphenyl)-ethylamine Hydrochloride, Compound 125

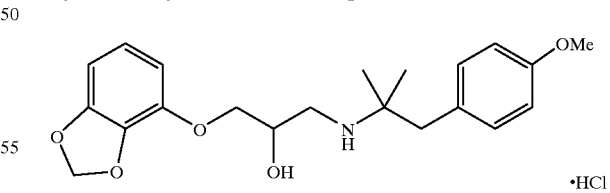

Using the method of Example 9, supra, 1,2-epoxy-3-(3,4-methylenedioxyphenoxy)propane (194 mg, 1 mmol) and 1,1-dimethyl-2-(4-methoxyphenyl)ethylamine (180 mg, 1 mmol) were used to prepare the hydrochloride salt of the title compound. MPLC of the free amine (silica gel, 1% MeOH/CHCl$_3$), followed by treatment with an excess of 1 M HCl/ether, yielded 88 mg of a white powder: GC/EI-MS, m/z (rel. int.) 374 (M$^+$, 0.0), 253 (15), 252 (100), 137 (8), 121 (16), 114 (8), 71 (12), 70 (8).

Example 77

Preparation of N-[2-hydroxy-3-(6-phenylhexanoxy)propyl]-1,1-dimethyl-2-(4-methoxyphenyl)ethylamine, Compound 126

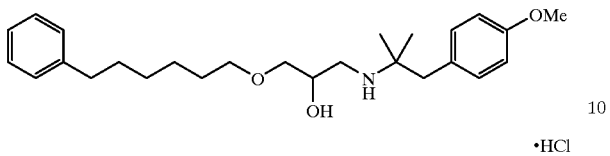

•HCl

Using the method of Example 9, supra, 6-phenylhexylglycidyl ether (337 mg, 1.44 mmol) and 1,1-dimethyl-2-(4-methoxyphenyl)ethylamine (180 mg, 1 mmol) were used to prepare the title compound. Preparative TLC (20 cm×20 cm×2 mm silica, eluted with 1%MeOH/CHCl$_3$) was used to purify the material and yielded 275 mg of free base: GC/EI-MS, m/z (rel. int.) 398 (M$^+$−15, 0.1), 293 (21), 292 (100), 163 (10), 121 (19), 114 (9), 91 (5), 90 (45), 71 (13), 70 (14), 58 (9).

Example 78

Preparation of N-[2-hydroxy-3-(4-phenylbutanoxy)propyl]-1,1-dimethyl-2-(4-methoxyphenyl)ethylamine, Compound 127

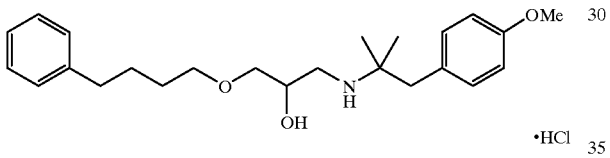

•HCl

Using the method of Example 9, supra, 4-phenylbutyl glycidyl ether (348 mg, 1.5 mmol) and 1,1-dimethyl-2-(4-methoxyphenyl)ethylamine (268 mg, 1.5 mmol) were used to prepare the title compound. Preparative TLC (20 cm×20 cm×2 mm silica, eluted with 5% MeOH/CHCl$_3$) was used to purify the material and yielded 275 mg of free base: GC/EI-MS, m/z (rel. int.) 370 (M$^+$−15, 0.1), 265 (19), 264 (100), 163 (11), 121 (19), 114 (9), 90 (43), 71 (10), 70 (12), 58 (7).

Example 79

Preparation of N-(2-hydroxy-3-phenoxypropyl)-1,1-dimethyl-2-(3-fluoro-4-methoxyphenyl)ethylamine, Compound 128

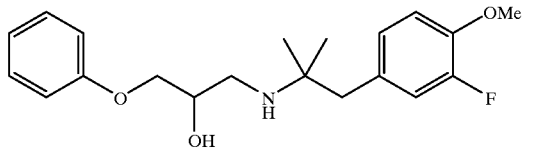

•HCl

Using the method of Example 6, supra, phenyl glycidyl ether (150 mg, 1.1 mmol) and 1,1-dimethyl-2-(3-fluoro-4-methoxyphenyl)ethylamine (197 mg, 1 mmol) were used to prepare the title compound. The title compound crystallized on standing to yield 169 mg of small crystals: GC/EI-MS, m/z (rel. int.) 332 (M$^+$−15, 0.1), 209 (16), 208 (100), 139 (13), 133 (5), 114 (7), 107 (6), 77 (11), 71 (12), 70 (20), 58 (9).

Example 80

Preparation of N-(2-hydroxy-3-phenoxypropyl)-1,1-dimethyl-2-(2-fluoro-4-methoxyphenyl)ethylamine Hydrochloride, Compound 129

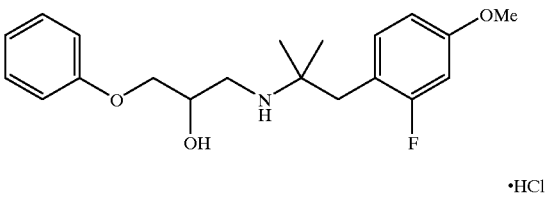

•HCl

Using the method of Example 6, supra, phenyl glycidyl ether (150 mg, 1.1 mmol) and 1,1-dimethyl-2-(2-fluoro-4-methoxyphenyl)ethylamine (197 mg, 1 mmol) were used to prepare the title compound. Preparative HPLC (C$_{18}$ reversed-phase, eluted with 1% HCl/CH$_3$CN gradient) was used to purify the compound, yielding 301 mg of a white powder: GC/EI-MS, m/z (rel. int.) 332 (M$^+$−15,1), 209 (15), 208 (100), 139 (14), 114 (5), 107 (5), 77 (6), 71 (7), 70 (13), 58 (5).

Example 81

Preparation of N-[2-hydroxy-3-(5-methoxy-1-napthoxy)propyl]-1,1-dimethyl-2-(4-methoxyphenyl)ethylamine Hydrochloride, Compound 130

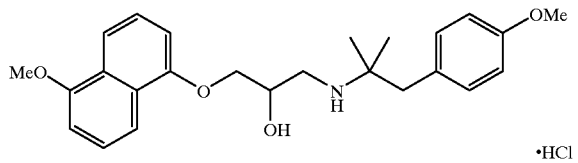

•HCl

Potassium carbonate (13 mmol) was added to a solution of 1,5-dihydroxy napthalene (6.2 mmol) in acetone in a sealed vacuum tube. The tube was heated to 70° C. for 30 minutes. Iodomethane (9.4 mmol) was added and the tube heated to 70° C. overnight.

The reaction mixture was partitioned between ether and 10% aqueous HCl. The ether layer was separated and extracted with 0.5 M KOH. The water layer was separated and acidified with 10% aqueous HCl and extracted into ether. The ether layer was separated and dried over magnesium sulfate and evaporated to a solid. The solid was purified using reverse phase HPLC using a acetonitrile/0.% HCl gradient yielding 179 mg 1-hydroxy-5-methoxy napthalene.

Sodium hydride (60% suspension in mineral oil, 1 mmol) was added to a solution of 1-hydroxy-5-methoxy napthalene (1 mmol) and stirred 10 minutes. Epichlorohydrin (1 mmol) was added and the reaction stirred at 70° C. for 72 hours. The reaction mixture was diluted with 1 liter of saturated sodium chloride solution and extracted into ether. The ether layer was then washed with water, separated and dried over anhydrous sodium sulfate and evaporated to give 5-methoxynapthalene glycidyl ether.

Using the method of Example 6, supra, 5-methoxynapthalene glycidyl ether (1 mmol) and 1,1-dimethyl-2-(4-methoxyphenyl)ethylamine (1 mmol) yielded 161 mg of the title compound as a white solid: GC/EI-MS, m/z (rel. int.) 360 (M+, 1), 289 (18), 288 (100), 173 (8), 121 (20), 71 (18), 70 (12).

Example 82
Preparation of N-[2-hydroxy-3-(2-cyanocyclohexyloxy) propyl]-1,1-dimethyl-2-(4-methoxyphenyl)ethylamine Hydrochloride, Compound 131

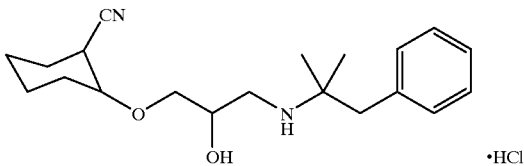

Sodium hydride (60% suspension in mineral oil, 60 mg, 1.59 mmol) was added to a solution of trans-2-cyanocyclohexanol in N,N-dimethylformamide (2.0 mL) and stirred for 10 minutes at room temperature. Epibromohydrin (0.22 g, 1.59 mmol) was then added and the reaction stirred for an additional 3 hours. The solution was partitioned between diethyl ether/water, and the layers separated. The ether layer was washed with water (3×100 mL) and dried over magnesium sulfate and evaporated to give 0.17 g of 2-cyanocyclohexyl glycidyl ether.

Using the method of Example 6, supra, 2-cyanocyclohexyl glycidyl ether (0.94 mmol) and 1,1-dimethyl-2-(4-methoxyphenyl)ethylamine (1.17 mmol) yielded 55 mg of the title compound as a white solid: GC/EI-MS, m/z (rel. int.) 360 (M+, 1), 239 (100), 121 (22), 240 (14), 70 (11)163 (8), 71 (8), 81 (7).

Example 83
Synthesis of (R/S)-1-[[2,2-dimethyl(4'methoxy)phenethyl]] amino-2-hydroxy-4(1'-naphthyl)-butane, Compound 162

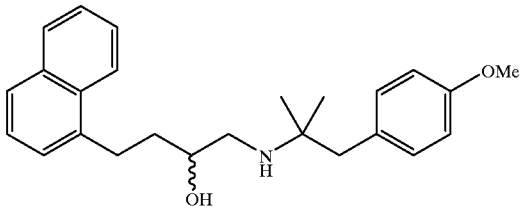

A solution of 1-chloromethylnaphthaline (750 uL, 5 mmol, Aldrich) in anhydrous ether (10 mL) was added dropwise to 25 mL of allyl magnesium bromide (1 M in ether) over 30 minutes. The resulting mixture was heated at reflux for 14 hours. After cooling the reaction to room temperature, it was quenched with 25 mL of saturated NH$_4$Cl (aqueous). The layers were separated and the organic layer was washed with brine, dried over Na$_2$SO$_4$, filtered and evaporated to give 1 g of 1-but-3-enyl-naphthalane that was carried without further purification.

1-But-3-enyl-naphthaline (1 g) from above was added to a solution of 50% mCPBA (2.1 g) in CH$_2$Cl$_2$ (50 mL) and the reaction stirred at room temperature for 48 hours. The material was diluted with CH$_2$Cl$_2$ and was extracted with sodium sulfite (aqueous) and NaHCO$_3$ (aqueous), dried over MgSO$_4$, filtered and evaporated to give 1-[(2-oxoaryl) ethyl]-naphthaline (1 g) that was carried without further purification.

A solution of 1-[(2-oxoaryl)ethyl]-naphthaline (1 g) and 1,1-dimethyl-2(4-methoxyphenyl) ethylamine (985 mg, 5.5 mmol) in ethanol (25 mL) was heated at reflux for 12 hours. The reaction was evaporated and the residue dissolved in 4 N HCl/dioxane. Upon addition of ether, crystals formed and were subsequently collected and dried in a vacuum oven to give 1.4 g of (R/S)-1-]]2,2-dimethyl-(4'methoxy) phenethyl]]amino-2-hydroxy-4(1'-naphthyl)-butane. ESMS [(M+H]$^+$=378, $^1$H NMR (CDCl$_3$, 360 MHz) @300° K δ8.06 (1H, d of d), 7.83 (1H, d of d), 7.78–7.61 (2H, m), 7.49–7.35 (3H, m), 7.09–7.02 (2H, m), 6.84–6.79 (2H, m), 3.76 (3H, s), 3.61 (1H,m), 3.33–3.09 (2H, m), 2.77–2.72 (1H, d of d), 2.62 (2H, s), 2.47–2.42 (1H, m), 1.85–1.82 (2H, m), 1.04 (6H, s).

Example 84
Synthesis of (R/S)-1-[[2,2-dimethyl-(4'methoxy)phenethyl]] amino-2-hydroxy-4[1'-2,3-dichlorophenyl)]-butane, Compound 163

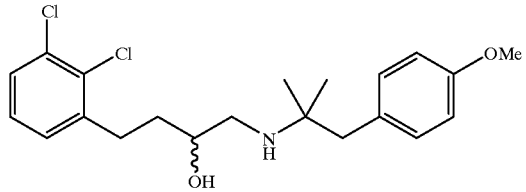

Starting from 2,3-dichlorobenzylchloride (1 g, 5 mmol) and following the three step procedure described in Example 83, 660 mg of (R/S)-1-[[2,2-dimethyl-(4'methoxy) phenethyl]]amino-2-hydroxy-4[1'-(2,3-dichlorophenyl)]-butane was synthesized and isolated as white crystals. ESMS [M+H]$^+$=396 $^1$H NMR (CDCl$_3$, 360 MHz) @300° K δ7.3 (1H, d of d), 7.18 (1H, d of d), 7.10–7.03 (3H, m), 6.82–6.80 (2H, m), 3.78 (3H, s), 3.47 (1H, m), 2.97–2.83 (2H, m), 2.74 (1H, m) 2.60 (2H, s), 2.43–2.37 (1H, m), 1.71 (2H, m), 1.04 (6H, s).

Example 85
Synthesis of (R/S)-1-nitro-5-hydroxy-6-[1,1-dimethyl-2-(4-methoxyphenyl)]hexane, Compound 164

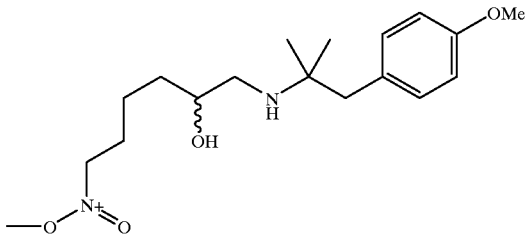

Starting from 6-nitro-1-hexene (1 g, 7.75 mmol) and following the two last steps described in Example 83, 1 g of (R/S)-1-nitro-5-hydroxy-6-[1,1-dimethyl-2(4-methoxyphenyl)]hexane was synthesized and isolated as tan crystals. ESMS [M+H]$^-$=325 $^1$H NMR (CDCl$_3$, 360 MHz) @ 300° K δ7.00 (4H, d of d), 4.37 (2H, t), 3.77 (3H, s), 3.49 (1H, m), 2.74 (1H, d of d), 2.61 (2H, s), 2.35 (1H, m) 2.03 (2H, m), 1.60–1.43 (4H, m) 1.08 (6H, s).

Example 86
N-[2(R)-Hydroxy-3-[(2,3-dichloro-4-dipropylsulfamoyl) phenoxy]-1-propyl]-N-[1,1-dimethyl-2-(4-methoxyphenyl) ethyl]amine Hydrochloride Salt Compound 165

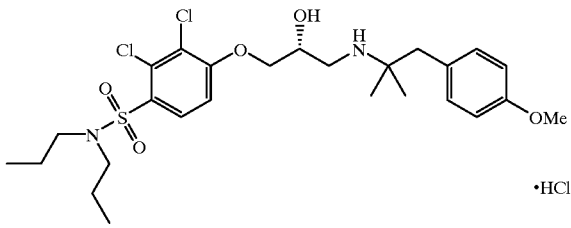

a) (2,3-Dichloro-4-methoxy)phenylsufonylchloride 2,3-dichloroanisole (Aldrich, 9.0 g, 50.8 mmol) was utilized in the method of H. Harada et al., *Chem Pharm Bull* (1987) 35(8) 3195–3214 to give the title compound as a white solid (13.3, 95%).

b) N,N-Dipropyl-(2,3-dichloro-4-methoxy) phenylsulfonamide.

The compound of Example 86a (8.0 g, 29.0 mmol) was dissolved in $CH_2Cl_2$ (200 mL) and dipropylamine (11.9 mL, 87.1 mmol) in EtOH (40 mL) was added at –20° C. The ice bath was removed and the mixture stirred 1.5 hours. The mixture was poured into $H_2O$ and extracted with $CH_2Cl_2$. The combined organic extracts were washed with $H_2O$ and brine, concentrated in vacuo and azeotroped with toluene to yield the title compound as a light brown-tinted oil (9.8 g, 100%). 1H NMR (400 MHz, $CDCl_3$) d 8.05 (d, J=10 Hz, 1H), 6.92 (d, J=10 Hz, 1H), 4.00 (s, 3H), 3.23 (t, J=8, 17 Hz, 4H), 1.52 (m, 4H), 0.83 (t, J=8, 13 Hz, 6H).

c) N,N-Dipropyl-2,3-dichloro-4-hydroxyphenylsulfonamide.

The compound from Example 86b (10.0 g, 29.4 mmol), $I_2$ (14.9 g, 58.8 mmol) and trimethylphenylsilane (15.1 mL, 88.2 mmol) were stirred together and heated to 110° C. for 18 hours. The mixture was poured into aqueous $Na_2S_2O_3$, extracted with EtOAc, dried ($MgSO_4$), concentrated to dryness in vacuo and purified by column chromatography (silica gel, 40% EtOAc in hexanes) to give a clear oil (9.2 g, 86%). 1H NMR (400 MHz, $CDCl_3$) d 7.98 (d, J=10 Hz, 1H), 7.05 (d, J=10 Hz, 1H), 6.29 (brs, 1H), 3.24(t, J=9, 18 Hz, 4H), 1.56 (m, 4H), 0.84 (t, J=8, 14 Hz, 6H).

d) [2,3-Dichloro-4-(N,N-dipropylsulfamoyl)]phenyl glycidyl ether.

The compound of Example 86c (5.0 g, 15.3 mmol), $K_2CO_3$ (6.4 g, 46.0 mmol), and (2R)-(–)-glycidyl 3-nitrobenzenesulfonate (5.6 g, 15.3 mmol) were heated in acetone (250 mL) to reflux 18 hours. The solvent was concentrated in vacuo to half volume, poured into $H_2O$, extracted with EtOAc, the combined organic extracts were dried ($MgSO_4$), evaporated and purified by column chromatography (silica gel, 40% EtOAc in hexanes) to give the title compound as a clear oil (4.9 g, 84%). 1H NMR (400 MHz, $CDCl_3$) d 8.04 (d, J=8 Hz, 1H), 6.94 (d, J=8 Hz, 1H), 4.45 (dd, J=1, 9 Hz, 1H), 4.11 (dd, J=7, 11 Hz, 1H), 3.44 (m, 1H), 3.24 (t, J=9, 18 Hz, 4H), 2.97 (m, 1H), 2.87(m, 1H), 1.52 (m, 4H), 0.84 (t, J=6,14 Hz, 6H)

e) N-[2(R)-Hydroxy-3-[(2,3-dichloro-4-dipropylsulfamoyl) phenoxy]-1-propyl]-N-[1,1-dimethyl-2-(4-methoxyphenyl) ethyl]amine hydrochloride salt.

The compound from Example 86d (1.6 g, 4.2 mmol), 1,1-dimethyl-2-(4-methoxyphenyl)ethylamine (0.75 g, 4.2 mmol) and $LiClO_4$ (0.89 g, 8.4 mmol) were dissolved in $CH_3CN$ (150 mL) and refluxed 18 hours. The mixture was concentrated in vacuo and purified by column chromatography (silica gel, 8% MeOH in $CH_2Cl_2$) to yield the title compound as a white solid (1.0 g, 44%). This was converted to the HCl salt by adding 1.7 mL of 1M HCl in MeOH, stirring 5 minutes, concentrating in vacuo, azeotroping with toluene then $CH_2Cl_2$. MS (ES) m/e 561.1[M+H+]; 1H NMR (400 MHz, $CDCl_3$) d 9.94 (bs, 1H), 8.02 (d, J=8 HZ, 1H), 7.14 (d, J=8 HZ, 2H), 6.96 (d, J=8 HZ, 1H), 6.86 (d, J=7 Hz, 1H), 4.78 (m, 1H), 4.30 (m, 1H), 4.20 (m, 1H), 3.80 (s, 3H), 3.68 (m, 2H), 3.43 (bs, 1H), 3.23 (t, J=7, 14 Hz, 4H), 3.12 (m, 2H), 1.50 (q, J=5, 13 Hz, 4H), 1.43 (s, 3H), 1.38 (s, 3H), 0.83 (t, J=8,13, 6H).

Example 87
Additional Compounds

Additional compounds were synthesized using techniques along lines as those described above. Examples of such compounds include the following:

Compound 1: N-[2-hydroxy-3-(2-hydroxybenzimidazol-4-oxyl)propyl]-1,1-dimethyl-2-4-methoxyphenyl) ethylamine.

Compound 14: (R)-N-[2-hydroxy-3-(1-naphthoxy) propyl]-1-methyl-3-methoxybenzylamine.

Compound 22: N-(3-phenylpropyl)-1,1-dimethyl-2(4-methoxyphenyl)ethylamine.

Compound 24: N-(4-phenylbutyl)-1,1-dimethyl-2-(4-methoxyphenyl)ethylamine.

Compound 34: N-(Benzyl)-1,1-dimethyl-2-(4-methoxyphenyl)ethylamine.

Compound 36: N-(4-phenoxybutyl)-1,1-dimethyl-2-(4-methoxyphenyl)ethylamine.

Compound 42: N-(3-(1-napthoxy)propyl)-1,1-dimethyl-2-(4-methoxyphenyl).

Compound 52: N-[2-hydroxy-3-(2-acetamidophenoxy) propyl]-1,1-dimethyl-2(4-methoxyphenyl)ethylamine.

Compound 53: N-(2-phenoxyethyl)-1,1-dimethyl-2-(4-methoxyphenyl)ethylamine.

Compound 54: N-2-hydroxy-3-(4-tert-butylphenoxy) propyl]-1,1-dimethyl-2-phenylethylamine.

Compound 55: N-[2-hydroxy-3-(1-naphthoxy)propyl]-1, 1-dimethyl-2-phenylethylamine.

Compound 58: N-[2-hydroxy-3-(4-acetamidophenoxy) propyl]-1,1-dimethyl-2-(4-methoxyphenyl)ethylamine.

Compound 60: N-[2-hydroxy-3-(2-phenylphenoxy) propyl]-1,1-dimethyl-2-(4-methoxyphenyl)ethylamine.

Compound 61: N-[2-hydroxy-3-(3-phenylphenoxy) propyl]-1,1-dimethyl-2-(4-methoxyphenyl)ethylamine.

Compound 62: N-[2-Hydroxy-3-(4-phenylphenoxy) propyl]-1,1-dimethyl-2-(4-methoxyphenyl)ethylamine.

Compound 84: N-(2-Phenylethyl)-1,1-dimethyl-2-(4-methoxyphenyl)ethylamine.

Compound 92: N-(2-hydroxy-3-phenoxypropyl)-1,1-dimethyl-2-(1-naphthyl)ethylamine.

Compound 93: N-(2-hydroxy-3-cyclohexoxypropyl)-1,1-dimethyl-2-(4-methoxyphenyl)ethylamine.

Compound 102: N-(2-hydroxy-3-phenoxypropyl)-1,1-dimethyl-2-(4-ethoxyphenyl)ethylamine.

Compound 132: N-[2-hydroxy-3-(3,4-dimethoxyphenoxy)propyl]-1,1-dimethyl-2-(4-methoxyphenyl) ethylamine Hydrochloride; GC/EI-MS, m/z (rel. int.) 390 (M+, 0.0), 269 (17), 268 (100), 163 (6), 153 (5), 121 (21), 114 (17), 77 (5), 71 (19), 70 (17), 58 (7).

Compound 133: N-[2-hydroxy-3-(3,5-dimethoxyphenoxy)propyl]-1,1-dimethyl-2-(4-methoxyphenyl)ethylamine Hydrochloride; GC/EI-MS, m/z (rel. int.) 390 (M+, 0.0), 269 (16), 268 (100), 193 (9), 163 (8), 154 (7), 121 (24), 114 (46), 76 (6), 71 (11), 70 (18).

Compound 134: N-[2-hydroxy-3-(2-carbomethoxyphenoxy)propyl]-1,1-dimethyl-2-(4- methoxyphenyl)ethylamine Hydrochloride; $^1$H NMR (CDCl$_3$) δ1.42 (s, 3H), 1.44 (s, 3H), 3.2 (dd, 2H), 3.3–3.6 (bm, 2H), 3.7 (s, 3H), 3.8 (s, 3H), 4.1–4.4 (m, 3H), 4.7 (m, 1H), 6.8 (d, 2H), 7.0 (m, 2H), 7.2 (d, 2H), 7.5 (t, 1H), 7.8 (d, 1H), 8.8 (m, 1H), 9.3 (m, 1H).

Compound 135: N-[2-hydroxy-3-(4-methylphenoxy)propyl]-1,1-dimethyl-2-(4-methoxyphenyl)ethylamine Hydrochloride; GC/EI-MS, m/z (rel. int.) 328 (M−15,0.1), 223 (15), 222 (100), 163 (6), 147 (6), 121 (23), 114 (9).

Compound 136: N-[2-hydroxy-3-(2,3-dichlorophenoxy)-propyl]-1,1-dimethyl-2-(4-methoxyphenyl)ethylamine Hydrochloride; GC/EI-MS, m/z (rel. int.) 382 (M−15,0.1), 280 (10), 279 (9), 278 (62), 276 (100), 163 (11), 121 (28).

Compound 137: N-[2-hydroxy-3-(3,5-dichlorophenoxy)propyl]-1,1-dimethyl-2-(4-methoxyphenyl)ethylamine Hydrochloride; GC/EI-MS, m/z (rel. int.) 382 (M−15,1), 280 (11), 279 (9), 278 (65), 277 (16), 276 (100), 163 (8), 146 (5), 144 (5).

Compound 138: N-[2-hydroxy-3-(2,4-dichlorophenoxy)propyl]-1,1-dimethyl-2-(4-methoxyphenyl)ethylamine Hydrochloride; GC/EI-MS, m/z (rel. int.) 382 (M−15,1), 280 (11), 279 (9), 278 (65), 277 (5), 276 (100), 163 (10), 161 (6), 132 (5).

Compound 139: N-[2-hydroxy-3-(3,4-dichlorophenoxy)propyl]-1,1-dimethyl-2-(4-methoxyphenyl)ethylamine Hydrochloride; GC/EI-MS, m/z (rel. int.) 382 (M−15,0.1), 279 (10), 279 (9), 278 (63), 276 (100), 163 (9), 146 (5), 121 (29).

Compound 140: N-[2-hydroxy-3-(2,5-dichlorophenoxy)propyl]-1,1-dimethyl-2-(4-methoxyphenyl)ethylamine Hydrochloride; GC/EI-MS, m/z (rel. int.) 382 (M−15,0.1), 280 (11), 279 (9), 278 (64), 276 (100), 163 (9), 161 (5), 121 (29), 113 (8).

Compound 141: N-[2-hydroxy-3-(4-ethylphenoxy)propyl]-1,1-dimethyl-2-(4-methoxyphenyl)ethylamine Hydrochloride; GC/EI-MS, m/z (rel. int.) 342 (M−15,0.1), 237 (15), 236 (100), 163 (5), 121 (19), 114 (7).

Compound 142: N-[2-hydroxy-3-(2-cyanophenoxy)propyl]-1,1-dimethyl-2-(4-methoxyphenyl)ethylamine Hydrochloride; GC/EI-MS, m/z (rel. int.) 339 (M−15,1), 234 (15), 233 (100), 163 (5), 121 (14).

Compound 143: N-[2-hydroxy-3-(3-nitrophenoxy)propyl]-1,1-dimethyl-2-(4-methoxyphenyl)ethylamine Hydrochloride; GC/EI-MS, m/z (rel. int.) 359 (M−15,0.1), 254 (15), 253 (100), 163 (5), 121 (15).

Compound 144: N-[2-hydroxy-3-(4-ethoxyphenoxy)propyl]-1,1-dimethyl-2-(4-methoxyphenyl)ethylamine Hydrochloride; GC/EI-MS, m/z (rel. int.) 358 (M−15,0.1), 253 (17), 252 (100), 163 (6), 121 (21), 114 (8), 108 (8).

Compound 145: N-[2-hydroxy-3-(4-iso-propylphenoxy)propyl]-1,1-dimethyl-2-(4-methoxyphenyl)ethylamine Hydrochloride; GC/EI-MS, m/z (rel. int.) 356 (M−15,0.1), 251 (18), 250 (100), 163 (7), 121 (23), 117 (7), 114 (8).

Compound 146: N-[2-hydroxy-3-(3-iso-propylphenoxy)propyl]-1,1-dimethyl-2-(4-methoxyphenyl)ethylamine Hydrochloride; GC/EI-MS, m/z (rel. int.) 356 (M−15,0.1), 251 (18), 250 (100), 163 (6), 121 (21), 117 (5), 114 (10), 91 (9).

Compound 147: N-[2-hydroxy-3-(3-ethoxyphenoxy)propyl]-1,1-dimethyl-2-(4-methoxyphenyl)ethylamine Hydrochloride; GC/EI-MS, m/z (rel. int.) 358 (M−15,1), 253(16), 252 (100), 163 (5), 121 (20), 114 (12), 77 (5).

Compound 148: N-[2-hydroxy-3-(2-n-propylphenoxy)propyl]-1,1-dimethyl-2-(4-methoxyphenyl)ethylamine Hydrochloride; GC/EI-MS, m/z (rel. int.) 356 (M−15,1), 251(17), 250 (100), 163 (6), 121 (34), 114 (9), 107 (6), 90 (17), 78 (9), 77 (10), 71 (17).

Compound 149: N-[2-hydroxy-3-(4-n-propylphenoxy)propyl]-1,1-dimethyl-2-(4-methoxyphenyl)ethylamine Hydrochloride; GC/EI-MS, m/z (rel. int.) 356 (M−15,0.8), 251(18), 250 (100), 163 (5), 121 (19), 114 (7), 110 (5), 107 (7), 91 (6).

Compound 150: N-[2-Hydroxy-3-(3-ethylphenoxy)propyl]-1,1-dimethyl-2-(4-methoxyphenyl)ethylamine Hydrochloride; GC/EI-MS, m/z (rel. int.) 342 (M−15,0.6), 237(16), 236 (100), 163 (5), 121 (21), 114 (6), 105 (5), 90 (6).

Compound 151: N-[2-Hydroxy-3-(2-ethylphenoxy)propyl]-1,1-dimethyl-2-(4-methoxyphenyl)ethylamine Hydrochloride; GC/EI-MS, m/z (rel. int.) 342 (M−15,1), 237 (16), 236 (100), 163 (5), 121 (17), 114 (7), 91 (6), 77 (7).

Compound 152: N-[2-hydroxy-3-(4-trifluoromethoxyphenoxy)propyl]-1,1-dimethyl-2-(4-methoxyphenyl)ethylamine Hydrochloride; GC/EI-MS, m/z (rel. int.) 398 (M−15,2), 293(15), 292 (100), 121 (20), 77 (5).

Compound 153: N-[2-hydroxy-3-(2-iso-propylphenoxy)propyl]-1,1-dimethyl-2-(4-methoxyphenyl)ethylamine Hydrochloride; GC/EI-MS, m/z (rel. int.) 356 (M−15,1), 251 (19), 250 (100), 163 (5), 122 (5), 121 (53), 114 (8), 104 (6),103 (6), 91 (24), 77 (14).

Compound 154: N-[2-hydroxy-3-(3-trifluoromethoxyphenoxy)propyl]-1,1-dimethyl-2-(4-methoxyphenyl)ethylamine Hydrochloride; GC/EI-MS, m/z (rel. int.) 398 (M−15,0.1), 293 (15), 292 (100), 163 (7), 121 (18).

Compound 155: N-[2-hydroxy-3-(2,6-dichlorophenoxy)propyl]-1,1-dimethyl-2-(4-methoxyphenyl)ethylamine Hydrochloride; GC/EI-MS, m/z (rel. int.) 382 (M−15,1), 279 (11), 279 (9), 277 (64), 275 (100), 163 (11), 163 (5), 161 (6), 121 (33), 114 (12).

Compound 156: N-[2-hydroxy-3-(3,5-bistrifluoromethylphenoxy)propyl]-1,1-dimethyl-2-(4-methoxyphenyl)ethylamine Hydrochloride; GC/EI-MS, m/z (rel. int.) 450 (M−15,0.1), 345 (16), 344 (100), 213 (5), 163 (8), 121 (20).

Compound 157: N-[2-hydroxy-3-(3-chloro-5-methoxyphenoxy)propyl]-1,1-dimethyl-2-(4-methoxyphenyl)ethylamine Hydrochloride; GC/EI-MS, m/z (rel. int.) 378 (M−15,0.1), 275 (5), 274 (34), 273 (16), 272 (100), 163 (5), 121 (17), 114 (8).

Compound 158: N-[2-hydroxy-3-(4-nitrophenoxy)propyl]-1,1-dimethyl-2-(4-methoxyphenyl)ethylamine Hydrochloride; GC/EI-MS, m/z (rel. int.) 359 (M−15,1), 254 (14), 253 (100), 121 (12).

Compound 159: N-[2-hydroxy-3-(2-nitrophenoxy)propyl]-1,1-dimethyl-2-(4-methoxyphenyl)ethylamine Hydrochloride; GC/EI-MS, m/z (rel. int.) 359 (M−15,0.1), 254 (15), 253 (100), 163 (6), 121 (17), 114 (10), 96 (5), 78 (5).

Compound 160: N-[2-hydroxy-3-(3-cyanophenoxy)propyl]-1,1-dimethyl-2-(4-methoxyphenyl)ethylamine Hydrochloride; GC/EI-MS, m/z (rel. int.) 339 (M−15,0.1), 234 (15), 233 (100), 121 (21), 102 (7), 90 (6).

Compound 161: N-[2-hydroxy-3-(4-cyanophenoxy)propyl]-1,1-dimethyl-2-(4-methoxyphenyl)ethylamine Hydrochloride; GC/EI-MS, m/z (rel. int.) 339 (M−15,1), 234 (16), 233 (100), 163 (5), 121 (15), 102 (5).

Compound 166: N-[2R-Hydroxy-3-[(2-cyanobenzthien-3-yloxy)propyl]-1,1-dimethyl-2-(3,4,dichlorophenyl)ethylamine. Prepared as a hydrochloride salt, MS (ES) m/e 449 [M+H]$^+$ Compound 167: R-1-[1,1 Dimethyl-2-(4-methoxyphenyl)ethylaminol-3-(2'-carbazoloxy)pran-2-ol. Prepared as a trifluoroacetate salt, MS (ES) m/e 419.2 [M+H]$^+$.

Compound 168: N-[2R-Hydroxy-3-[(2-bromopyridinyloxy)propyl]-1,1-dimethyl-2-(4-methoxy)ethylamine. Prepared as a hydrochloride salt, MS (ES) m/e 411,409 [M+H]$^+$.

Compound 169: N-(2-hydroxy-3-(3-N,N-dimethylphenoxy) propyl)-1,1-dimethyl-2-(-4-methoxyphenyl)ethylamine, GC/MS 251(100), 176(9), 163(5), 138(11), 137(6),(8), 125(10), 121(23), 114(46), 108(6), 77(6), 76(7),(10), 70(14), 42(8).

Compound 170: N-(2-hydroxy-3-(3-phenylphenoxy)propyl)-1,1-dimethyl-2-(-4-methoxyphenyl)ethylamine. GC/MS (mt, 0.1), 284(100), 121(28), 285 (27), 152(13), 70(13), 71(11), 153(10).

Other embodiments are within the following claims. Thus, while several embodiments have been shown and described, various modifications may be made, without departing from the spirit and scope of the present invention.

What is claimed is:

1. A method for identifying a calcilytic compound that optimally inhibits one or more calcium receptor activities in a particular cell type, the method comprising:

contacting a particular type of calcium receptor-bearing cell with a calcilytic compound having the formula:

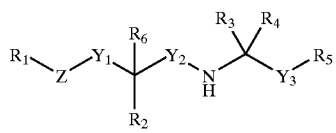

wherein $R_1$ is selected from the group consisting of: aryl, longer-length alk, and cyclo-alk;

$R_2$ is selected from the group consisting of: lower alk, cyclo-alk, alkoxy, H, OH, =O, C(O)OH, C(O)O-lower alk, C(O)NH-lower alk, C(O)N(lower alk)$_2$, SH, S-lower alk, NH$_2$, NH-lower alk, and N(lower alk)$_2$;

$R_3$ and $R_4$ are each independently lower alk or, together with the carbon to which they are attached, are cyclopropyl;

$R_5$ is aryl;

$R_6$ if present is either hydrogen, lower alkyl or optionally substituted lower alkenyl, wherein $R_6$ is not present if $R_2$ is =O;

$Y_1$ is either a covalent bond, alkylene, or alkenylene;

$Y_2$ is alkylene;

$Y_3$ is alkylene;

Z is selected from the group consisting of: a covalent bond, O, S, NH, N-lower alk, alkylene, alkenylene, and alkynylene, provided that if Z is either O, S, NH, or N-lower alk, then $Y_1$ is not a covalent bond; further provided that $Y_1$ and Z may together be a covalent bond, or a pharmaceutically acceptable salt or complex thereof; and determining the effect of said compound on a calcium receptor activity of said particular type of calcium receptor-bearing cell, wherein said calcilytic compound is identified by the inhibition of said calcium receptor activity.

2. The method of claim 1, wherein said method is carried out under conditions wherein influx of extracellular Ca$^{2+}$ into said one or more cells is inhibited.

3. The method of claim 1, wherein said one or more cells are contacted with said compound in vitro.

4. The method of claim 1, wherein said one or more cells are contacted with said compound in vivo.

5. The method of claim 1, wherein the effect of said compound on a calcium receptor activity is determined by measuring a serum hormone level.

6. The method of claim 5, wherein said serum hormone level is selected from the group consisting of parathyroid hormone level and calcitonin level.

7. The method of claim 1, wherein the effect of said compound on a calcium receptor activity is determined by measuring a serum calcium ion concentration.

8. The method of claim 1, wherein the effect of said compound on a calcium receptor activity is determined by measuring an intracellular calcium ion concentration.

9. The method of claim 1, wherein the effect of said compound on a calcium receptor activity is determined by measuring secretion of a hormone.

* * * * *